United States Patent
Zhang

(10) Patent No.: US 10,626,105 B2
(45) Date of Patent: Apr. 21, 2020

(54) DEUTERIUM-SUBSTITUTED PYRIDIN- AND PYRIMIDIN-2-YL-METHYLAMINE COMPOUNDS

(71) Applicant: Auspex Pharmaceuticals, Inc., Frazer, PA (US)

(72) Inventor: Chengzhi Zhang, San Diego, CA (US)

(73) Assignee: AUSPEX PHARMACEUTICALS, INC., North Wales, PA (US)

( * ) Notice: Subject to any disclaimer, the term of this patent is extended or adjusted under 35 U.S.C. 154(b) by 0 days.

(21) Appl. No.: 15/709,828

(22) Filed: Sep. 20, 2017

(65) Prior Publication Data

US 2018/0079742 A1  Mar. 22, 2018

Related U.S. Application Data

(60) Provisional application No. 62/398,239, filed on Sep. 22, 2016.

(51) Int. Cl.
*A61K 31/519* (2006.01)
*C07D 401/12* (2006.01)

(52) U.S. Cl.
CPC ........ *C07D 401/12* (2013.01); *C07B 2200/05* (2013.01)

(58) Field of Classification Search
CPC .............. A61K 31/519; A61K 31/4704; C07D 401/04; C07D 471/04
USPC .............. 514/264.11, 310; 544/279; 546/143
See application file for complete search history.

(56) References Cited

U.S. PATENT DOCUMENTS 6,020,345 A  2/2000 Vacher et al.
7,208,603 B2  4/2007 Maurel et al.

FOREIGN PATENT DOCUMENTS

| EP | 1539738 | | 6/2005 | |
|---|---|---|---|---|
| WO | WO 98/22459 | * | 11/1998 | ........... C07D 401/12 |
| WO | 2003/106449 A1 | | 12/2003 | |
| WO | WO 03/106449 | * | 12/2003 | ........... C07D 401/12 |
| WO | 2016/005527 A1 | | 1/2016 | |

OTHER PUBLICATIONS

Weyler et al., Purification and properties of mitochondrial monoamine oxidase type A from human placenta, J. Biol. Chem., 1985, 260, 13199-13207.

Ko et al., In vitro inhibition of the cytochrome P450 (CYP450) system by the antiplatelet drug ticlopidine: potent effect on CYP2C19 and CYP2D6, British Journal of Clinical Pharmacology, 2000, 49, 343-351.

Foster, Deuterium isotope effects in the metabolism of drugs and xenobiotics: implications for drug design, Advances in Drug Resea, Academic Press, London, GB, vol. 14, Jan. 1, 1985, pp. 1-40, XP009086953, ISSN: 0065-2490.

Bardin et al., Dual, Hyperalgesic, and Analgesic Effects of the High-Efficacy 5-Hydroxytryptamine 1A (5-HT-1A) Agonist F 13640 [3-Chloro-4-fluoro-phenyl)-[4-fluoro-4-{[5-methyl-pyridin-2-ylmethyl)-amino]-methyl}piperidin-1-yl] methanone, Fumaric Acid Salt]: Relationship with 5-HT 1A Receptor Occupancy and Kinetic parameters, The Journal of Pharmacology and Experimental Therapeutics, 2005, vol. 312 No. 3, 1034-1042.

Uebelhack et al., Inhibition of platelet MAO-B by kava pyrone-enriched extract from Piper methysticum Forster (kava-kava), Pharmacopsychiatry, 1998, 31, 187-192.

Shao, Derivatives of Tramadol for Increased Duration of Effect, Bioorganic & Medicinal Chemistry Letters, 16, 691-94, 2006.

Miwa, Kinetic Isotope Effects and 'Metabolic Switching' in cytochrome P450-Catalyzed Reactions, BioEssays, 7, 5, pp. 215-219, Nov. 1987.

Harbeson, Deuterium in Drug Discovery and Development, Annual Reports in Medicinal Chemistry, 46, Chapter 4, pp. 403-417, 2011.

Foster, Trends in Pharmacological Sciences, 1984, vol. 5, pp. 524-427.

Fisher, The Complexities Inherent in Attempts to Decrease Drug Clearance by Blocking Sites of CYP-Mediated Metabolism, Current Opinion in Drug Discovery & Development, 9, 1, 101-109, 2006.

* cited by examiner

*Primary Examiner* — Jeffrey H Murray
(74) *Attorney, Agent, or Firm* — BakerHostetler

(57) ABSTRACT

Described are deuterium-substituted pyridin- and pyrimidin-2-yl-methylamine compounds of structural Formula (I), which are agonists of 5-hydroxytryptamine receptors. Also described are pharmaceutical compositions comprising the deuterium-substituted pyridin- and pyrimidin-2-yl-methylamine compounds, and methods of use thereof.

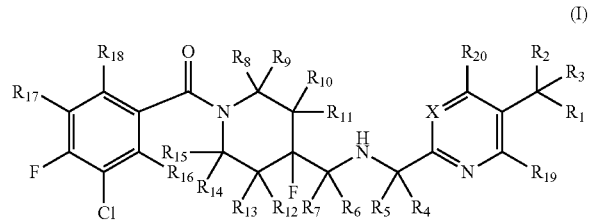

11 Claims, No Drawings

DEUTERIUM-SUBSTITUTED PYRIDIN- AND PYRIMIDIN-2-YL-METHYLAMINE COMPOUNDS

CROSS-REFERENCE TO RELATED APPLICATIONS

This application claims the benefit of priority of U.S. Provisional Patent Application No. 62/398,239, filed Sep. 22, 2016, the disclosure of which is hereby incorporated by reference, as if written herein, in its entirety.

TECHNICAL FIELD

The present invention relates generally to the field of pharmaceuticals and to methods of treating disorders. More particularly, provided herein are novel compounds which are agonists of 5-hydroxytryptamine receptors and are useful in treating or preventing disorders such as anxiety, depression, and movement disorders.

BACKGROUND

The serotonin receptors, also known as 5-hydroxytryptamine (5-HT) receptors are a group of G protein-coupled receptors (GPCRs) and ligand-gated channels found in the central and peripheral nervous system. The serotonin receptors are activated by serotonin, which is a neurotransmitter and a neuromodulator of the central nervous system. The 5-HT receptors have been grouped into several main classes. Among these main classes, the 5-HT$_1$ class comprises receptors characterized by a high affinity for serotonin. The 5-HT$_1$ class is itself divided into a subclass of receptors whose pharmacological characteristics and regional distributions in the central nervous system are distinct.

The 5-HT$_{1A}$ receptor is the most widespread of all the 5-HT$_1$ receptors. In the central nervous system, 5-HT$_{1A}$ receptors exist in the cerebral cortex, hippocampus, septum, amygdala, and raphe nucleus in high densities, while low amounts also exist in the basal ganglia and thalamus. 5-HT$_{1A}$ receptor agonists are involved in neuromodulation, decreasing blood pressure and heart rate via a central mechanism, by inducing peripheral vasodilation, and by stimulating the vagus nerve. Activation of central 5-HT$_{1A}$ receptors triggers the release or inhibition of norepinephrine. 5-HT$_{1A}$ receptor agonists show efficacy in relieving anxiety and depression.

Befiradol [(3-Chloro-4-fluoro-phenyl)-[4-fluoro-4-{[(5-methyl-pyridin-2-ylmethyl)-amino]-5 methyl}piperidin-1-yl]methanone; CAS #208110-64-9] is a selective and high efficacy serotonin 5-HT$_{1A}$ receptor agonist (U.S. Pat. Nos. 6,020,345; 7,208,603).

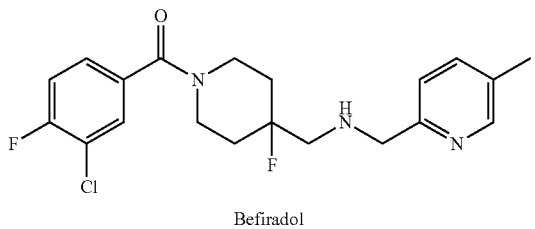

Befiradol

Befiradol has been suggested as a treatment for depression, anxiety, and pain. More recently, befiradol has been under investigation in the treatment of movement disorders including Parkinson's disease, Huntington's disease, Tourette's syndrome, dystonia, L-DOPA-induced dyskinesia, and tardive dyskinesia (WO 2016/005527).

Befiradol, however, is metabolized in the liver and is likely subject to extensive cytochrome P$_{450}$-mediated oxidative metabolism. Befiradol is likely metabolized predominantly by N-dealkylation.

Adverse effects associated with befiradol may include dizziness, light-headedness, headache, nausea, somnolence, insomnia, tachycardia, dry mouth, diarrhea, rash, and the like. Additionally, some metabolites of befiradol may have undesirable side effects.

Accordingly, there is a need for 5-HT$_{1A}$ receptor agonists with improved pharmacokinetic properties.

SUMMARY

Provided are deuterium-substituted pyridin- and pyrimidin-2-yl-methylamine compounds, which are 5-HT$_{1A}$ receptor agonists. Also provided are pharmaceutical compositions comprising the deuterium-substituted pyridin- and pyrimidin-2-yl-methylamine compounds, and methods of use thereof, including methods for treatment or prevention of 5-HT$_{1A}$ receptor-mediated disorders by administering, to a patient, the deuterium-substituted pyridin- and pyrimidin-2-yl-methylamine compounds or pharmaceutical compositions comprising the deuterium-substituted pyridin- and pyrimidin-2-yl-methylamine compounds. Further provided are methods of synthesizing the deuterium-substituted pyridin- and pyrimidin-2-yl-methylamine compounds.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

Deuterium Kinetic Isotope Effect

In order to eliminate foreign substances such as therapeutic agents, the animal body expresses various enzymes, such as the cytochrome P$_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k = Ae^{-E_{act}/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1H$), a C-D bond is stronger than the corresponding C-$^1H$ bond. If a C-$^1H$ bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C-$^1H$ bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects Deuterium ($^2H$ or D) is a stable and non-radioactive isotope of hydrogen which has approximately twice the mass of protium ($^1H$), the most common isotope of hydrogen. Deuterium oxide ($D_2O$ or "heavy water") looks and tastes like $H_2O$, but has different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Befiradol is a 5-$HT_{1A}$ receptor agonist. The carbon-hydrogen bonds of befiradol contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Deuterium Kinetic Isotope Effect (DKIE) that could affect the pharmacokinetic, pharmacologic and/or toxicologic profiles of such befiradol in comparison with the compound having naturally occurring levels of deuterium.

Befiradol is likely metabolized in humans by oxidation of hydrocarbons and N-dealkylations. The approach described herein has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a pharmaceutical with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the potential to slow the metabolism of befiradol and attenuate interpatient variability.

Deuterium-substituted pyridin- and pyrimidin-2-yl-methylamine compounds and pharmaceutical compositions employing such compounds, certain of which have been found to modulate the activity of 5-$HT_{1A}$ receptors have been discovered, together with methods of synthesizing and using the compounds, including methods for the treatment or prevention of 5-$HT_{1A}$ receptor-mediated disorders in a mammal by administering the compounds as disclosed herein.

In certain embodiments of the present invention, the deuterium-substituted pyridin- and pyrimidin-2-yl-methylamine compounds have a structure corresponding to Formula (I):

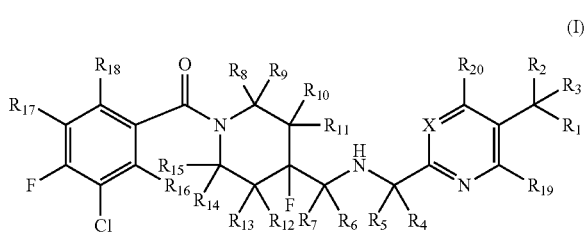

(I)

or a pharmaceutically acceptable salt, ester, prodrug, co-crystal, or solvate thereof, wherein:

X is selected from N or C—$R_{21}$; $R_1$-$R_{21}$ are independently selected from hydrogen and deuterium; and at least one of $R_1$-$R_{21}$ is deuterium.

In further embodiments, at least two of $R_1$-$R_{21}$ are deuterium, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$. In some embodiments, all of $R_1$-$R_{21}$ are deuterium.

In further embodiments, said pharmaceutically acceptable salt is selected from a hydrochloride, a hydrobromide, a sulfate, a formate, an acetate, a trifluoroacetate, a propionate, a succinate, a fumarate, a citrate, a tartrate, a glutamate, a benzoate, a salicylate, a stearate, a lactate, a mesylate, a tosylate, a besylate, a phosphate, a maleate, and the like.

In specific embodiments, said pharmaceutically acceptable salt is selected from a sulfate and a fumarate.

In certain embodiments, $R_1$-$R_3$ are deuterium.
In certain embodiments, $R_4$-$R_5$ are deuterium.
In certain embodiments, $R_6$-$R_7$ are deuterium.
In certain embodiments, $R_1$-$R_3$ and $R_4$-$R_5$ are deuterium.
In certain embodiments, $R_1$-$R_3$ and $R_6$-$R_7$ are deuterium.
In certain embodiments, $R_1$-$R_3$, $R_4$-$R_5$, and $R_6$-$R_7$ are deuterium.
In certain embodiments, $R_1$ is deuterium.
In certain embodiments, $R_2$ is deuterium.
In certain embodiments, $R_3$ is deuterium.
In certain embodiments, $R_4$ is deuterium.
In certain embodiments, $R_5$ is deuterium.
In certain embodiments, $R_6$ is deuterium.
In certain embodiments, $R_7$ is deuterium.
In certain embodiments, $R_8$ is deuterium.
In certain embodiments, $R_9$ is deuterium.
In certain embodiments, $R_{10}$ is deuterium.
In certain embodiments, $R_{11}$ is deuterium.
In certain embodiments, $R_{12}$ is deuterium.
In certain embodiments, $R_{13}$ is deuterium.
In certain embodiments, $R_{14}$ is deuterium.
In certain embodiments, $R_{15}$ is deuterium.
In certain embodiments, $R_{16}$ is deuterium.
In certain embodiments, $R_{17}$ is deuterium.
In certain embodiments, $R_{18}$ is deuterium.
In certain embodiments, $R_{19}$ is deuterium.
In certain embodiments, $R_{20}$ is deuterium.

Also provided herein are embodiments according to each of the embodiments above, wherein X is C—$R_{21}$.
In certain embodiments, $R_{21}$ is deuterium.
Also provided herein are embodiments according to each of the embodiments above, wherein X is N.

Also provided herein are embodiments according to each of the embodiments above, wherein at least one of $R_8$-$R_{21}$ are deuterium.

Also provided herein are embodiments according to each of the embodiments above, wherein all of $R_8$-$R_{21}$ are deuterium.

Also provided herein are embodiments according to each of the embodiments above, wherein every other substituent among $R_1$-$R_{21}$ not specified as deuterium is hydrogen.

Without intending to be bound by theory, it is understood that while compounds of Formula I containing the moiety

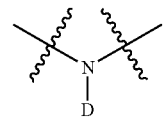

can be synthesized, it is believed that it is unlikely that the deuterium atom on these moieties will be retained after the compound is administered to a subject. When administered to a subject, it is thought that the deuterium in the moiety

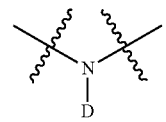

will be exchanged with a hydrogen atom to produce the moiety

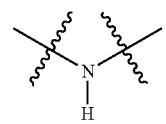 [SMILES: *N*]

due to the large amount of water present in a subject's body. Accordingly, embodiments of the invention encompass compounds comprising one or more

moieties in addition to one or more

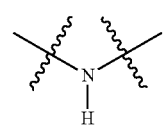 [SMILES: *N*]

moieties.

In certain embodiments are provided compounds as disclosed herein, wherein at least one of $R_1$-$R_{21}$ independently has deuterium enrichment of no less than about 1%. In further embodiments, at least two of $R_1$-$R_{21}$ have deuterium enrichment of no less than about 1%, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$ have deuterium enrichment of no less than about 1%. In some embodiments all of $R_1$-$R_{21}$ have deuterium enrichment of no less than about 1%.

In certain embodiments are provided compounds as disclosed herein, wherein at least one of $R_1$-$R_{21}$ independently has deuterium enrichment of no less than about 10%. In further embodiments, at least two of $R_1$-$R_{21}$ have deuterium enrichment of no less than about 10%, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$ have deuterium enrichment of no less than about 10%. In some embodiments all of $R_1$-$R_{21}$ have deuterium enrichment of no less than about 10%.

In certain embodiments are provided compounds as disclosed herein, wherein at least one of $R_1$-$R_{21}$ independently has deuterium enrichment of no less than about 50%, including about 55%, about 60%, about 65%, about 70%, about 75%, about 80%, about 85%, about 90%, about 95%, and about 100%. In further embodiments, at least two of $R_1$-$R_{21}$ have deuterium enrichment of no less than about 50%, including about 55%, about 60%, about 65%, about 70%, about 75%, about 80%, about 85%, about 90%, about 95%, and about 100%, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$. In some embodiments all of $R_1$-$R_{21}$ have deuterium enrichment of no less than about 50%, including about 55%, about 60%, about 65%, about 70%, about 75%, about 80%, about 85%, about 90%, about 95%, and about 100%.

In certain embodiments are provided compounds as disclosed herein, wherein at least one of $R_1$-$R_{21}$ independently has deuterium enrichment of no less than about 90%, including about 92%, about 94%, about 96%, about 98%, and about 100%. In further embodiments, at least two of $R_1$-$R_{21}$ have deuterium enrichment of no less than about 90%, including about 92%, about 94%, about 96%, about 98%, and about 100%, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$. In some embodiments all of $R_1$-$R_{21}$ have deuterium enrichment of no less than about 90%, including about 92%, about 94%, about 96%, about 98%, and about 100%.

In certain embodiments are provided compounds as disclosed herein, wherein at least one of $R_1$-$R_{21}$ independently has deuterium enrichment of no less than about 95%, including about 96%, about 97%, about 98%, about 99%, and about 100%. In further embodiments, at least two of $R_1$-$R_{21}$ have deuterium enrichment of no less than about 95%, including about 96%, about 97%, about 98%, about 99%, and about 100%, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$. In some embodiments all of $R_1$-$R_{21}$ have deuterium enrichment of no less than about 95%, including about 96%, about 97%, about 98%, about 99%, and about 100%.

In certain embodiments are provided compounds as disclosed herein, wherein at least one of $R_1$-$R_{21}$ independently has deuterium enrichment of no less than about 98%, including about 99%, and about 100%. In further embodiments, at least two of $R_1$-$R_{21}$ have deuterium enrichment of no less than about 98%, including about 99%, and about 100%, including at least three of $R_1$-$R_{21}$, at least four of $R_1$-$R_{21}$, at least five of $R_1$-$R_{21}$, at least six of $R_1$-$R_{21}$, at least seven of $R_1$-$R_{21}$, at least eight of $R_1$-$R_{21}$, at least nine of $R_1$-$R_{21}$, at least ten of $R_1$-$R_{21}$, at least eleven of $R_1$-$R_{21}$, at least twelve of $R_1$-$R_{21}$, at least thirteen of $R_1$-$R_{21}$, at least fourteen of $R_1$-$R_{21}$, at least fifteen of $R_1$-$R_{21}$, at least sixteen of $R_1$-$R_{21}$, at least seventeen of $R_1$-$R_{21}$, at least eighteen of $R_1$-$R_{21}$, at least nineteen of $R_1$-$R_{21}$, and at least twenty of $R_1$-$R_{21}$. In some embodiments all of $R_1$-$R_{21}$ have deuterium enrichment of no less than about 98%, including about 99%, and about 100%.

In other embodiments, provided is a compound of intermediate of Formula (II):

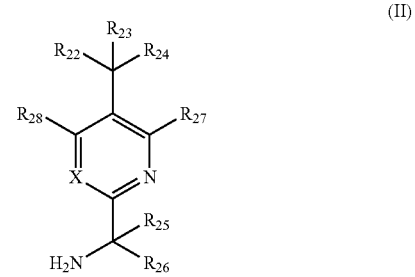

or a pharmaceutically acceptable salt, ester, prodrug, co-crystal, or solvate thereof, wherein:

X is selected from N or C—$R_{29}$; $R_{22}$-$R_{29}$ are independently selected from hydrogen and deuterium; and at least one of $R_{22}$-$R_{29}$ is deuterium.

In certain embodiments, $R_{22}$-$R_{24}$ are deuterium.
In certain embodiments, $R_{25}$-$R_{26}$ are deuterium.
In certain embodiments, $R_{22}$ is deuterium.
In certain embodiments, $R_{23}$ is deuterium.
In certain embodiments, $R_{24}$ is deuterium.
In certain embodiments, $R_{25}$ is deuterium.
In certain embodiments, $R_{26}$ is deuterium.
In certain embodiments, $R_{27}$ is deuterium.
In certain embodiments, $R_{28}$ is deuterium.
In certain embodiments, $R_{29}$ is deuterium.

Also provided herein are embodiments according to each of the embodiments above, wherein at least one of $R_{27}$-$R_{29}$ are deuterium.

Also provided herein are embodiments according to each of the embodiments above, wherein every other substituent among $R_{22}$-$R_{29}$ not specified as deuterium is hydrogen.

In specific embodiments, the compound or intermediate of Formula II is selected from:

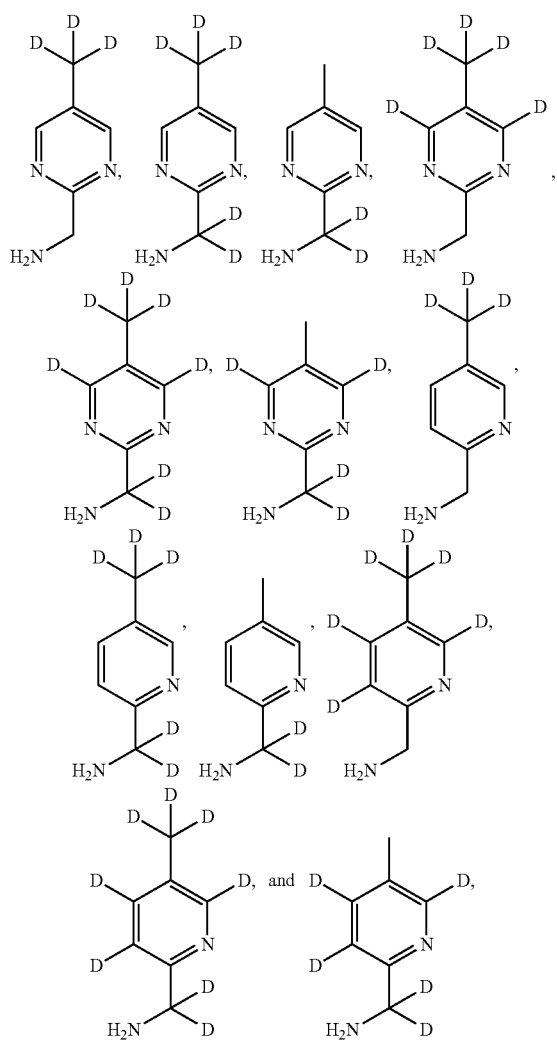

or pharmaceutically acceptable salts, esters, prodrugs, co-crystals, or solvates thereof.

Certain compounds disclosed herein may possess useful 5-$HT_{1A}$ receptor agonist activity, and may be used in the treatment or prophylaxis of a disorder in which 5-$HT_{1A}$ receptor agonist activity plays an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for modulating the activity of 5-$HT_{1A}$ receptors. Other embodiments provide methods for treating a 5-$HT_{1A}$ receptor-mediated disorder in a mammal and/or patient in need of such treatment, comprising administering to said patient a therapeutically effective amount of a compound or composition (of Formula I) according to the present invention. Also provided is the use of certain compounds disclosed herein for use in the manufacture of a medicament for the prevention or treatment of a disorder ameliorated by modulating the activity of one or more 5-$HT_{1A}$ receptors.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments, said compound of Formula I is selected from the group consisting of:

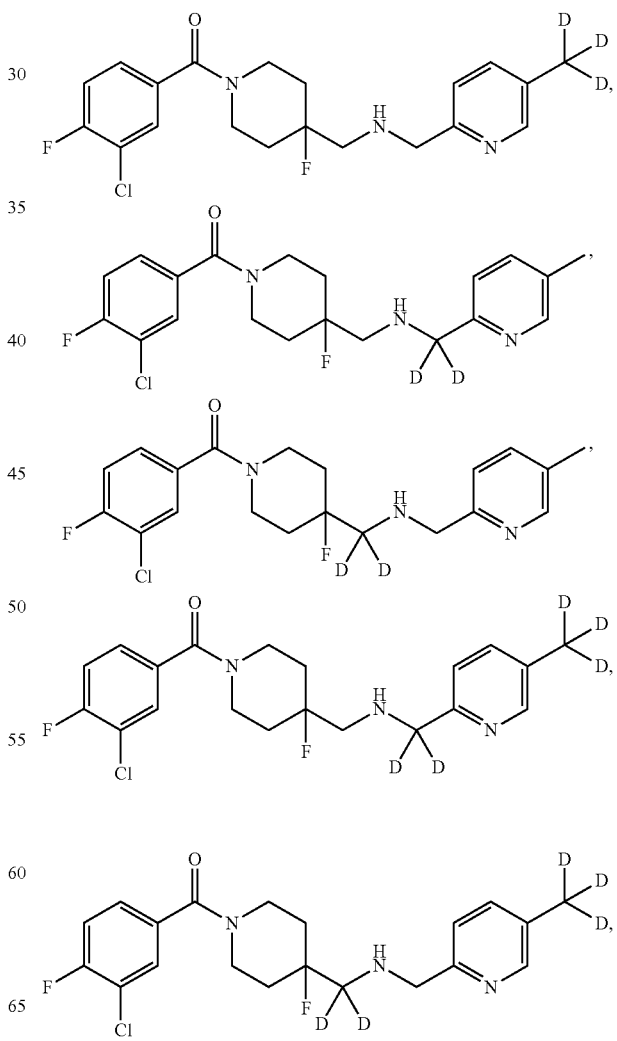

It is noted that in any of the above enumerated compounds of Formula I, the aromatic rings (i.e. the pyridine ring, the pyrimidine ring, and/or the phenyl ring) may also contain one or more deuterium.

In other embodiments, the compound of Formula I is selected from:

-continued

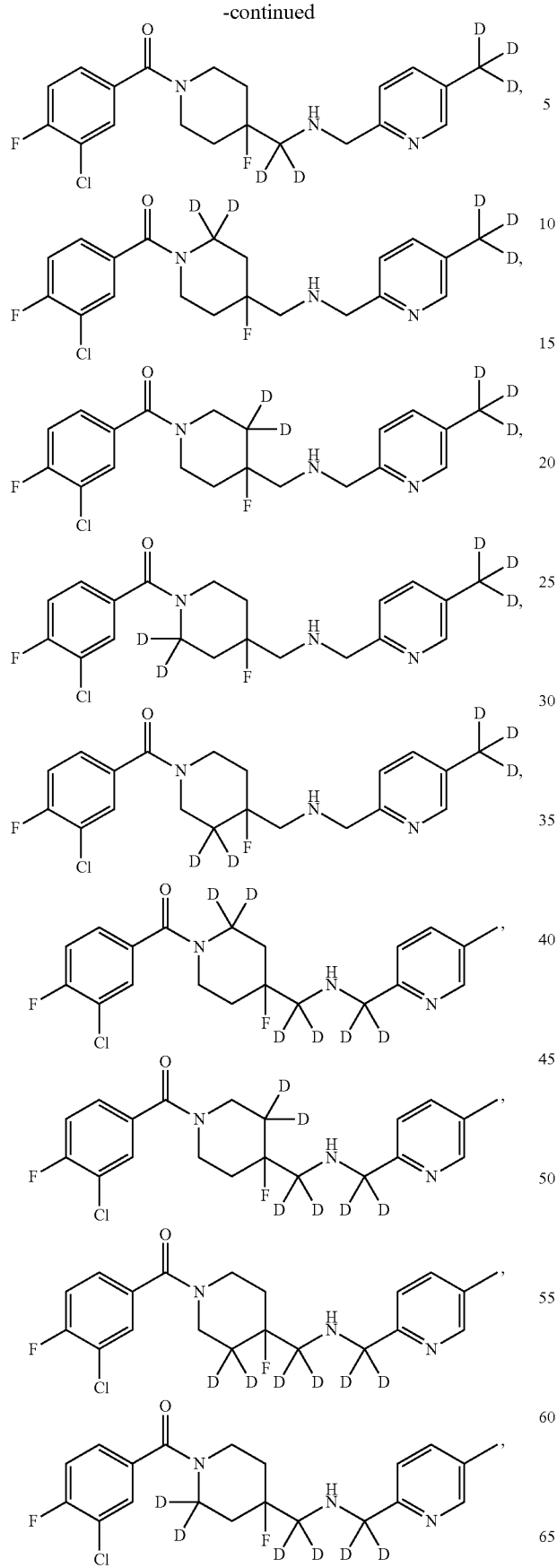
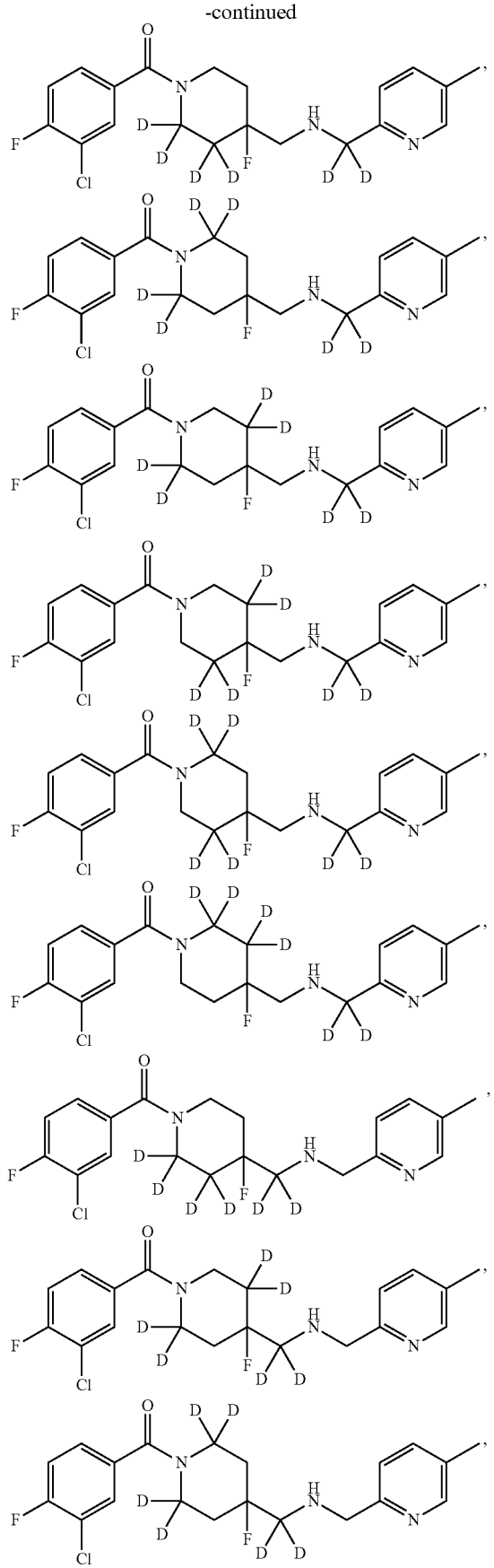

-continued
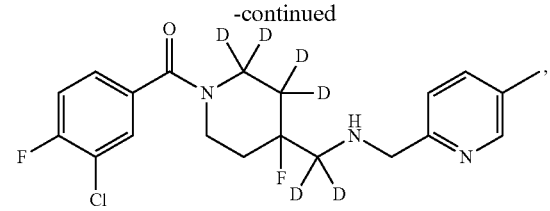
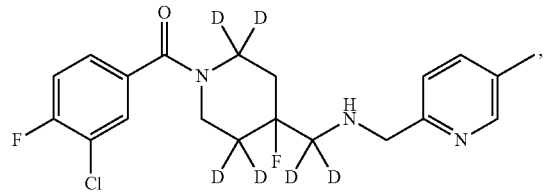
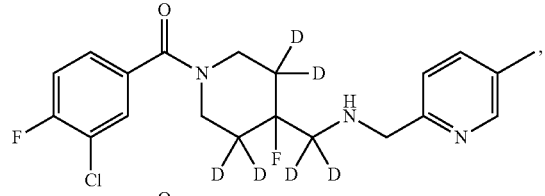
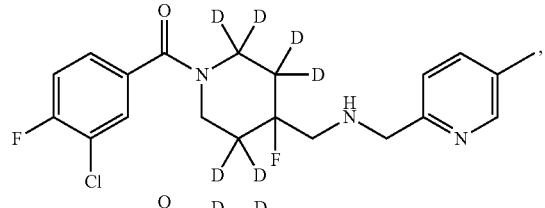
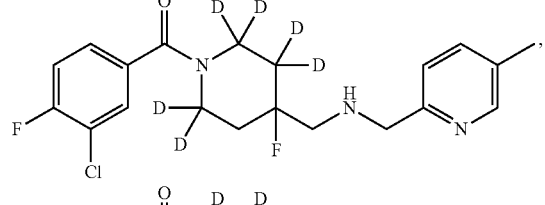
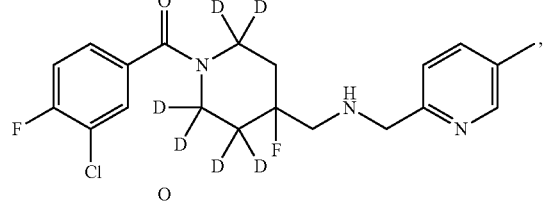
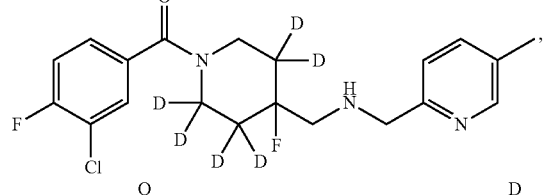
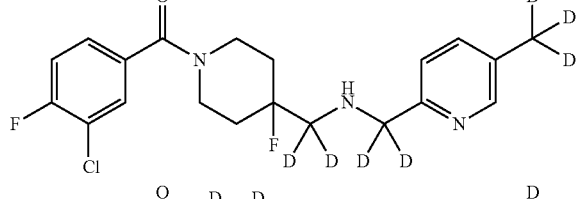
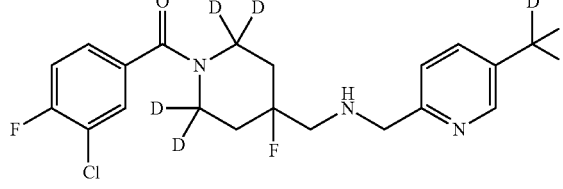
-continued
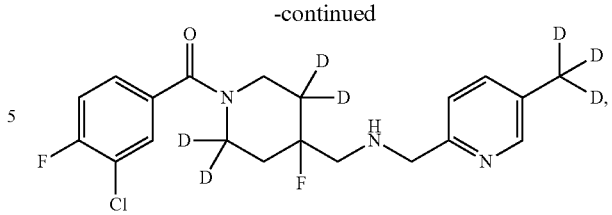
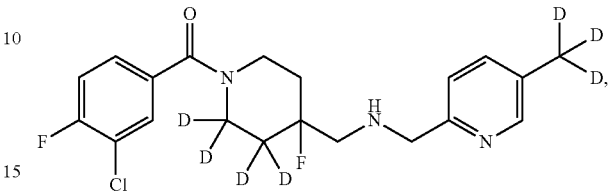
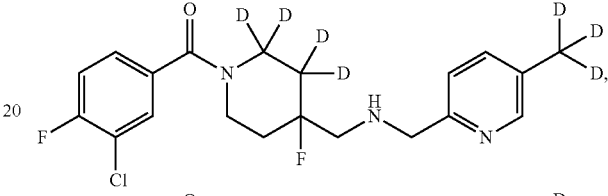
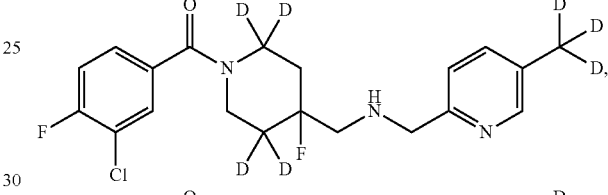
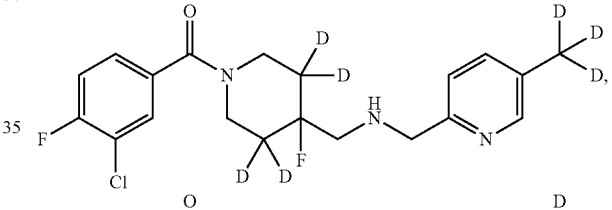
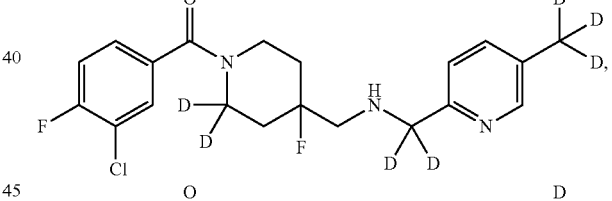
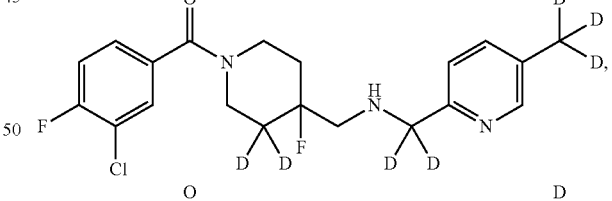
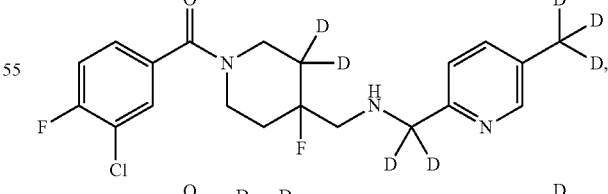
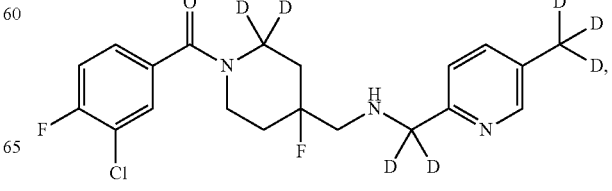

-continued
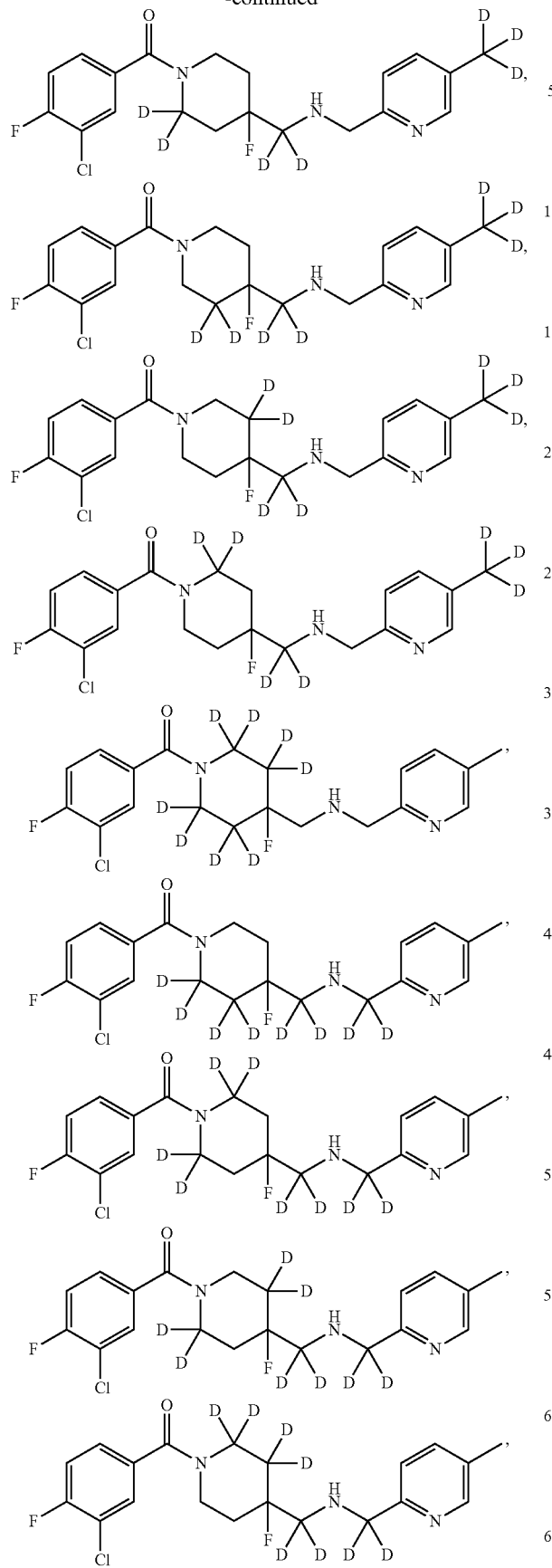
-continued
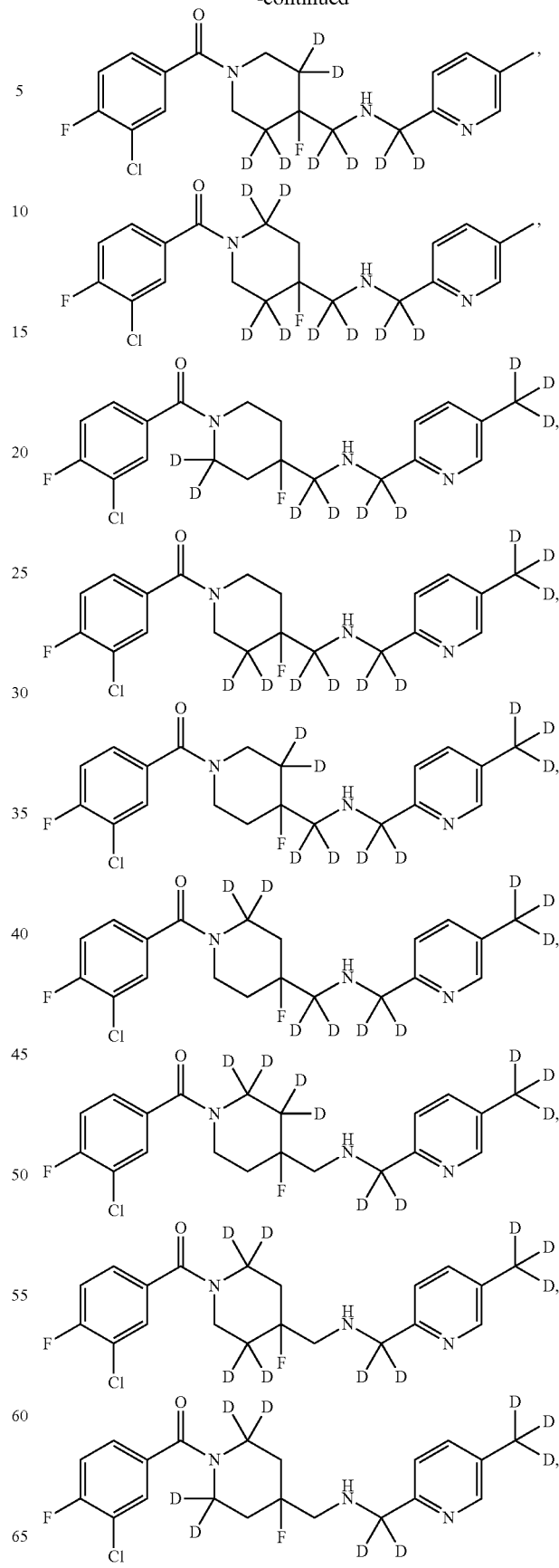

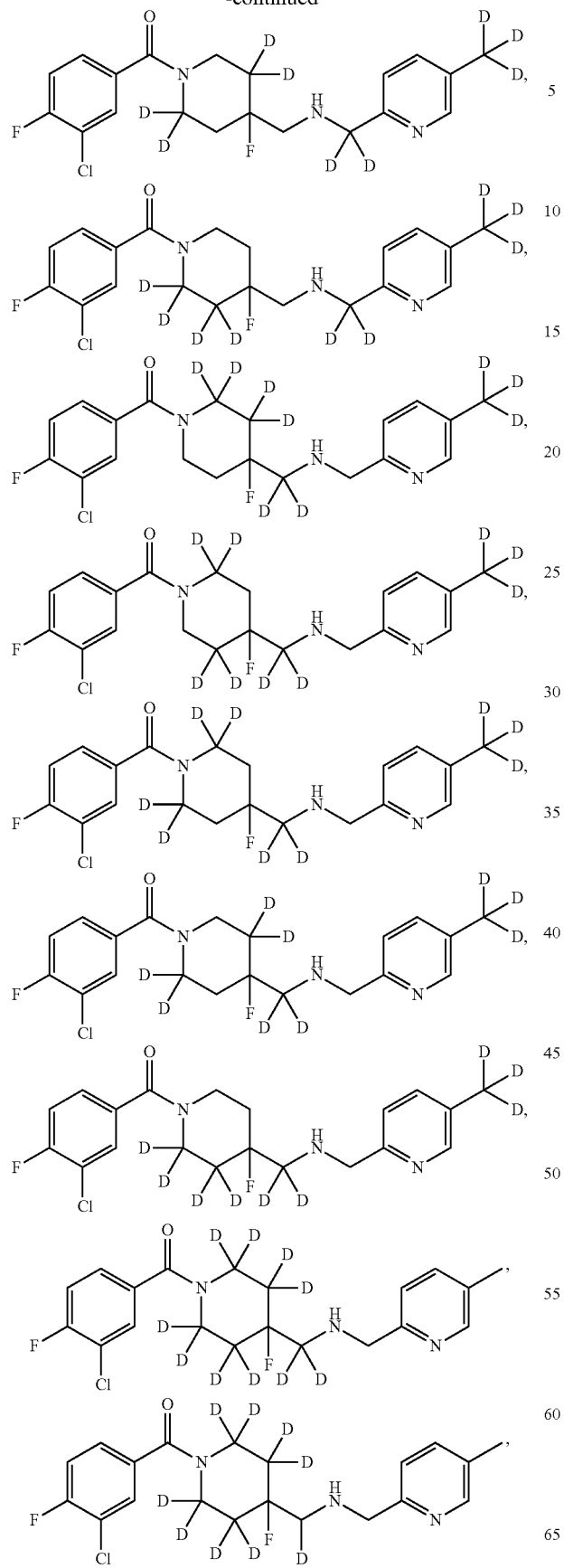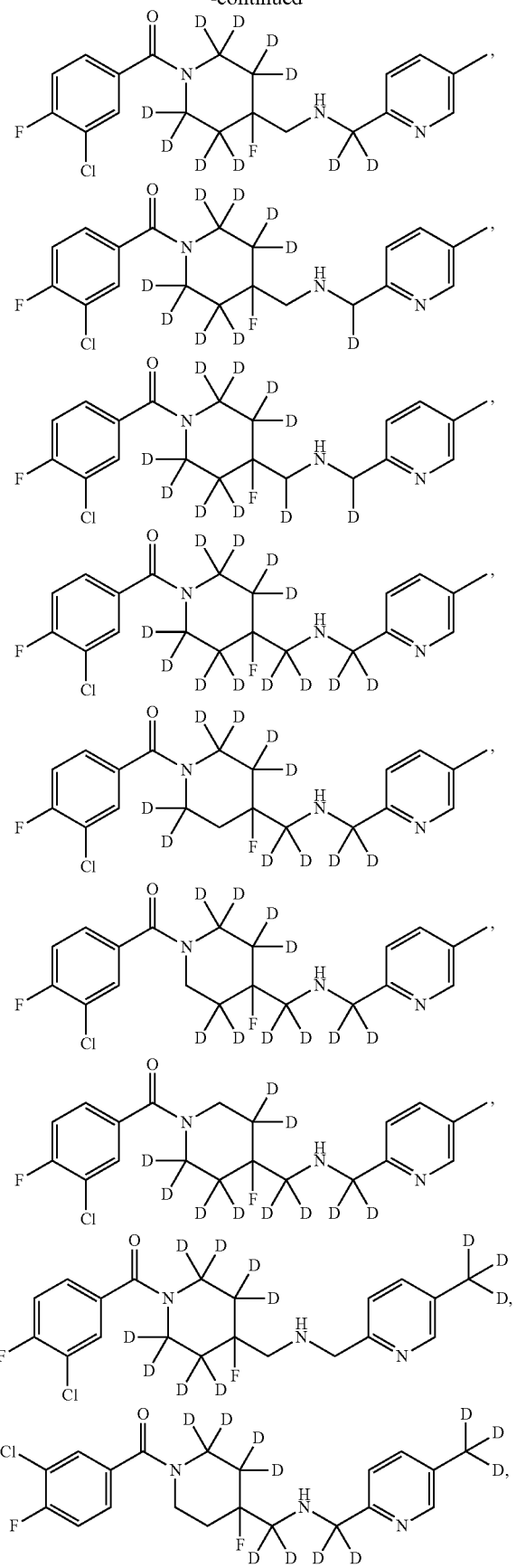

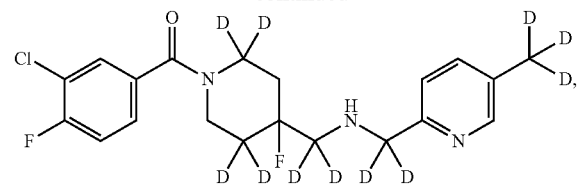
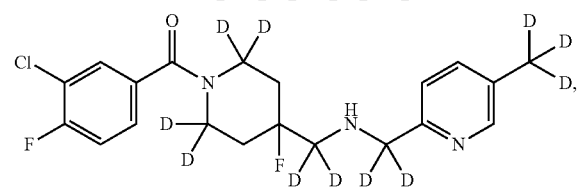
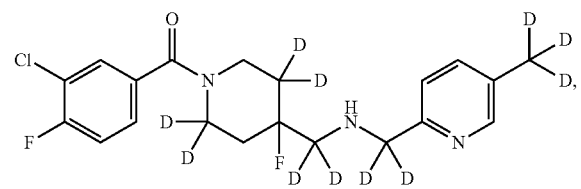
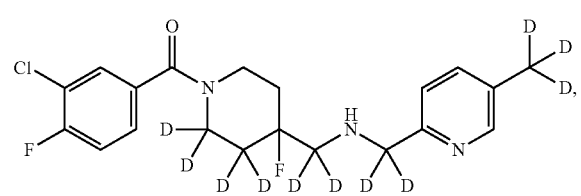
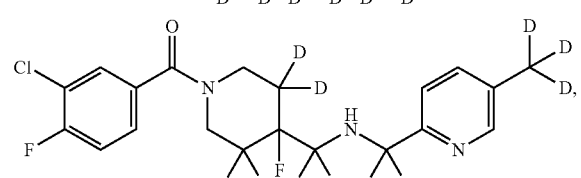
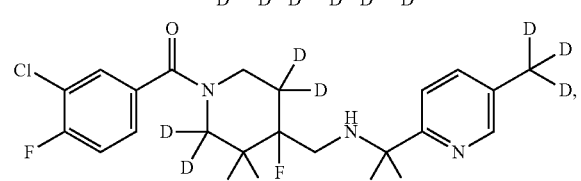
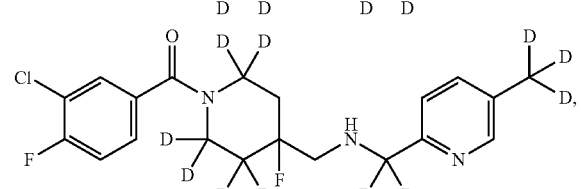
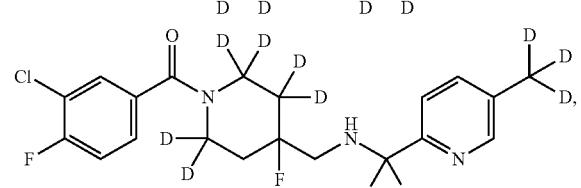
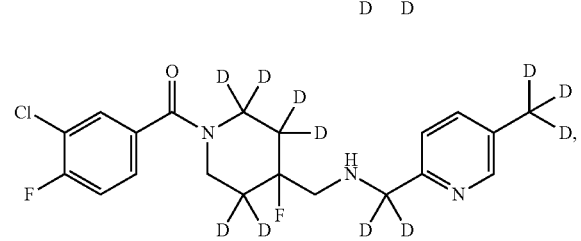
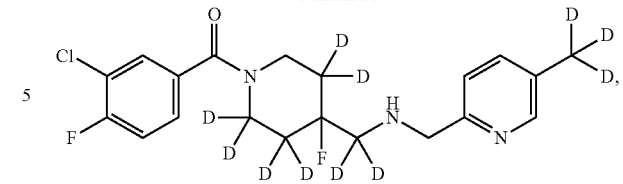
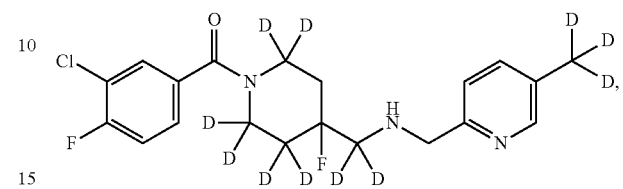
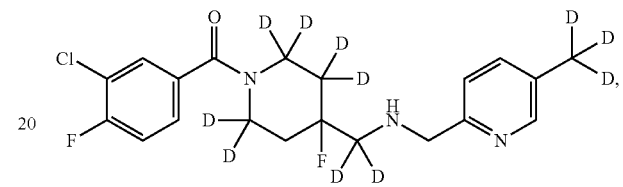
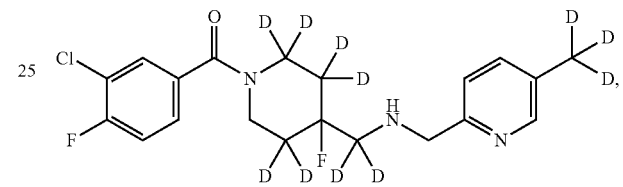
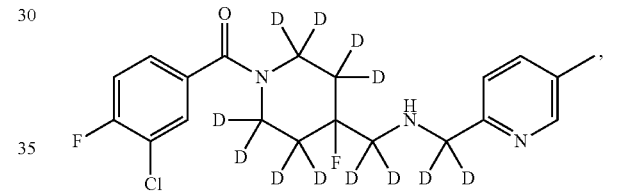
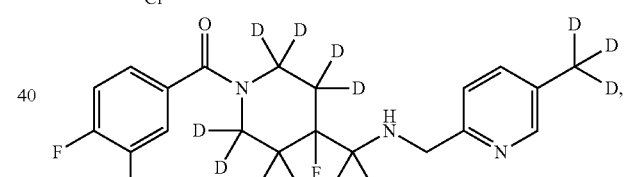
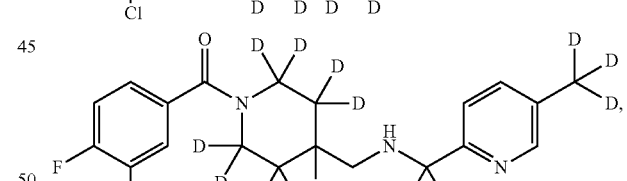
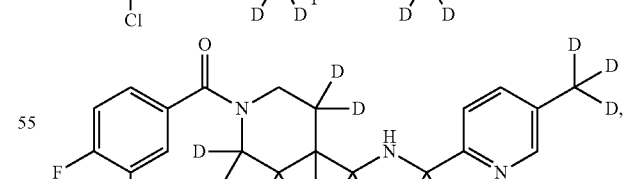
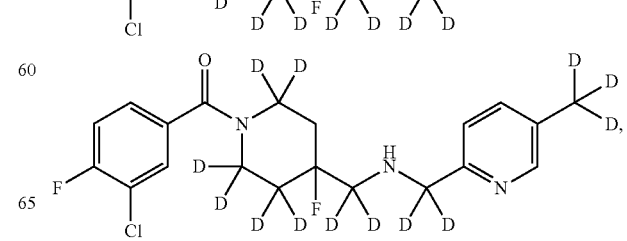

25
-continued
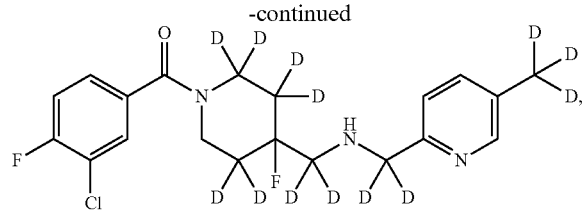
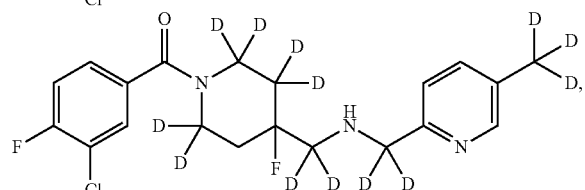
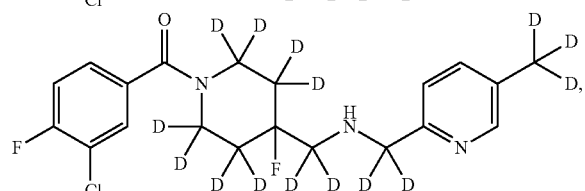
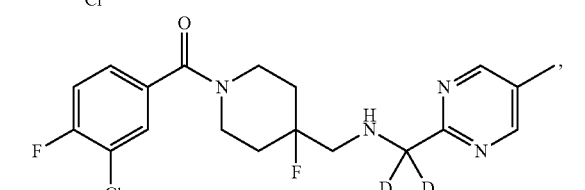
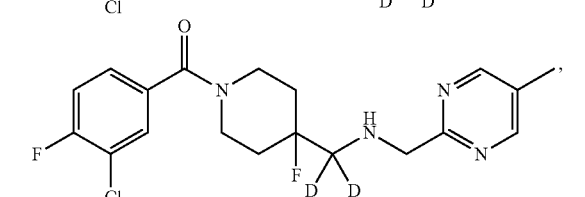
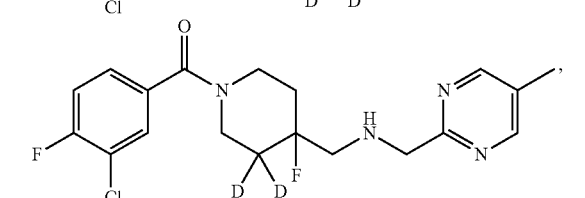
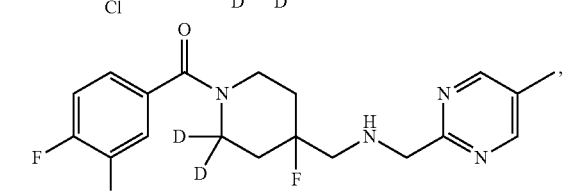
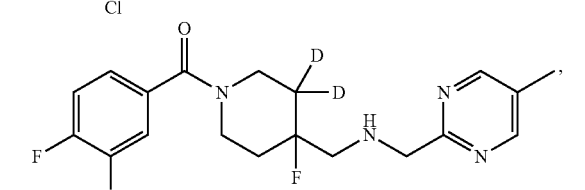
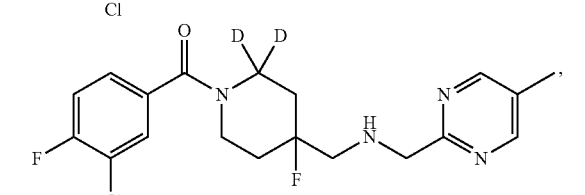
26
-continued
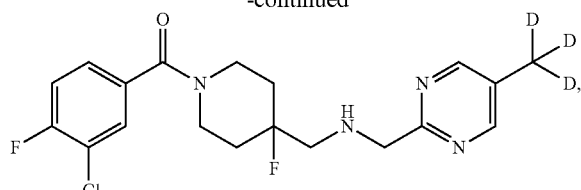
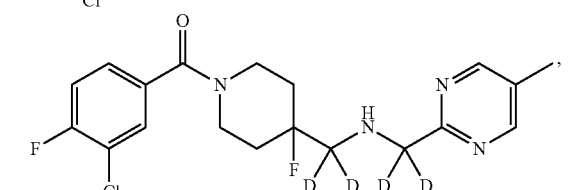
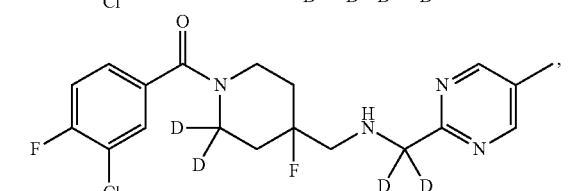
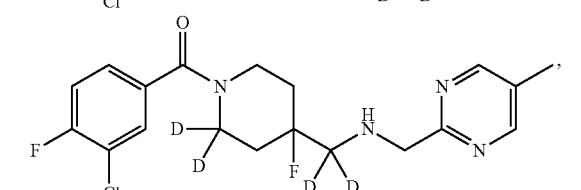
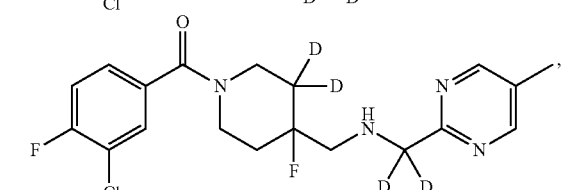
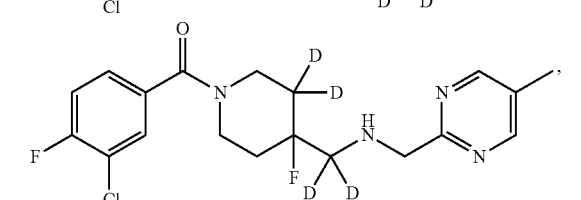
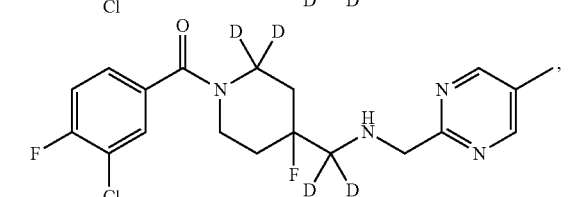
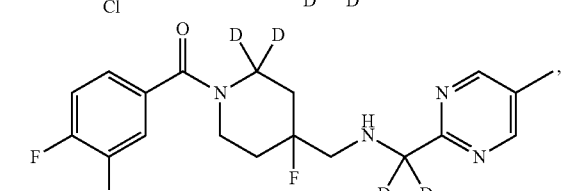
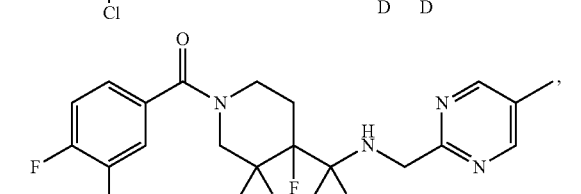

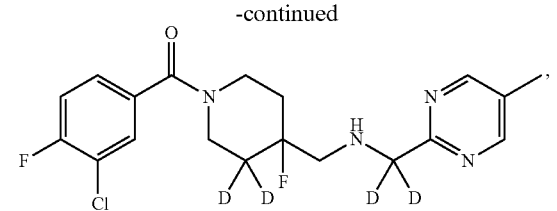
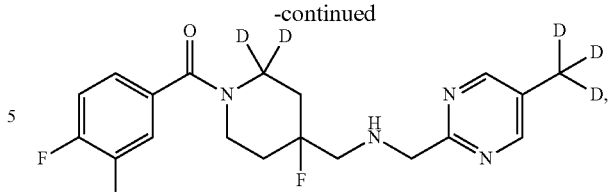
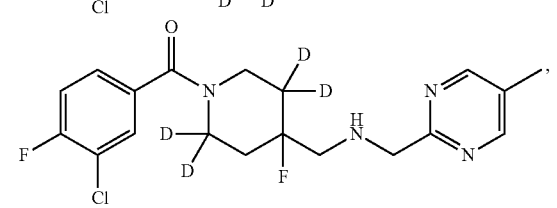
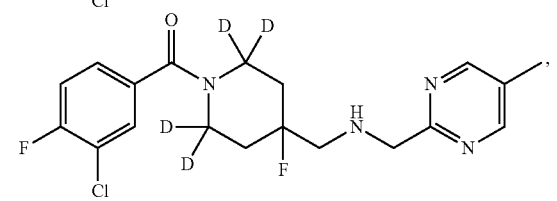
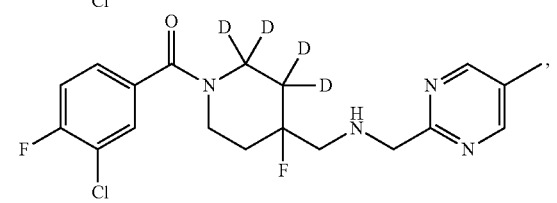
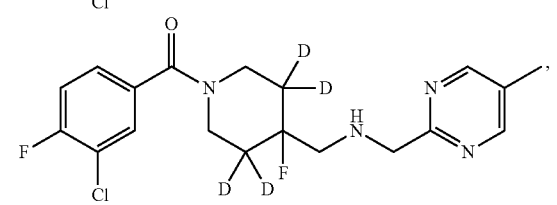
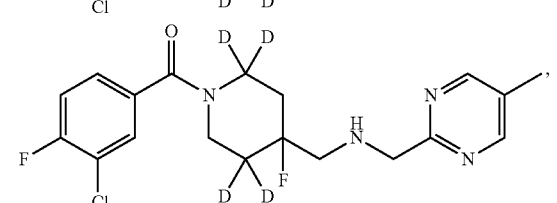
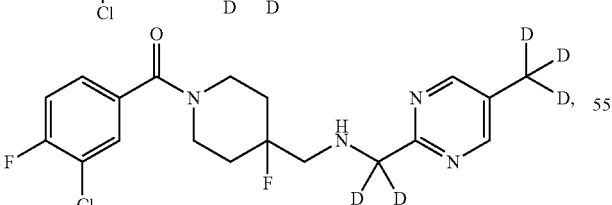
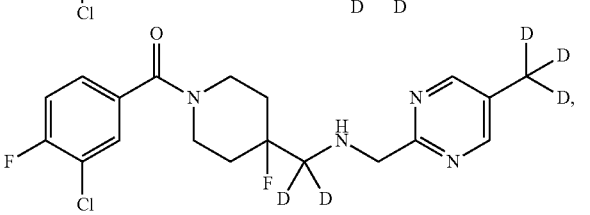

-continued
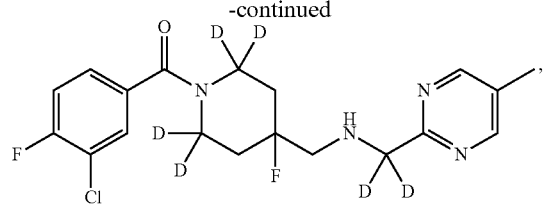
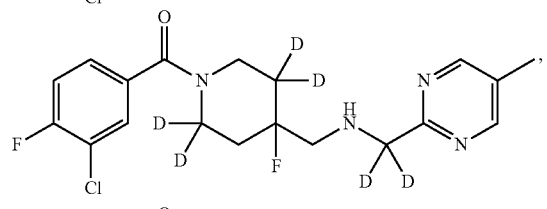
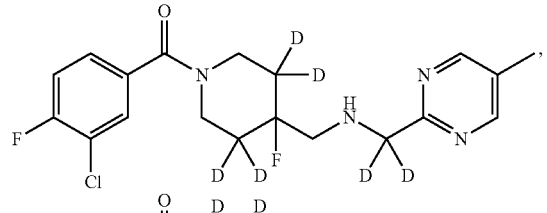
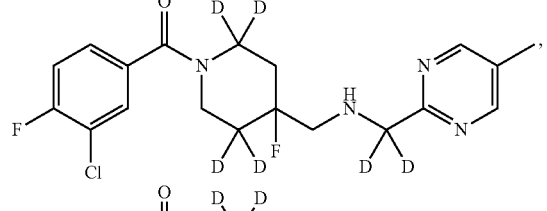
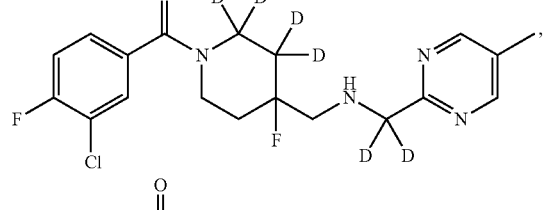
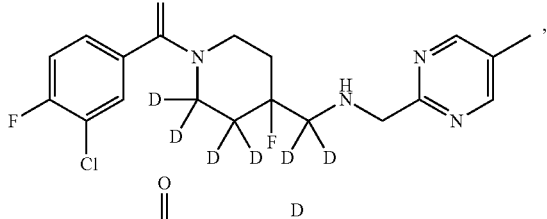
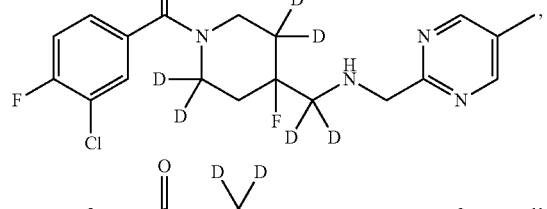
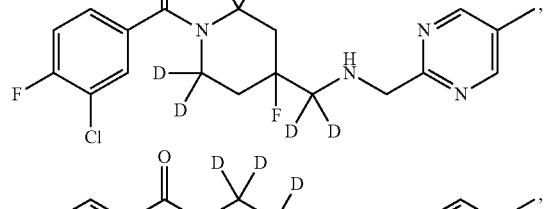
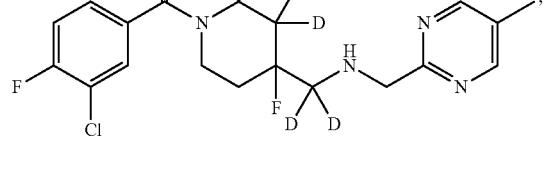
-continued
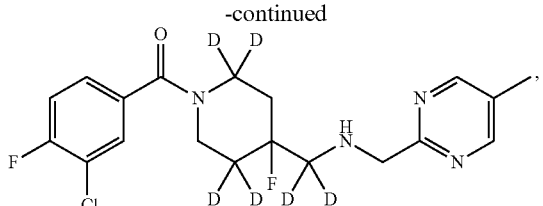
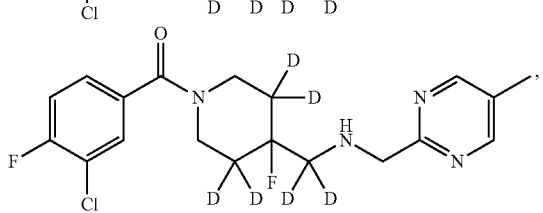
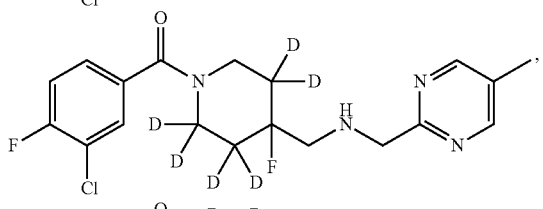
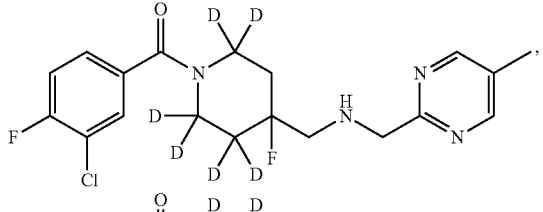
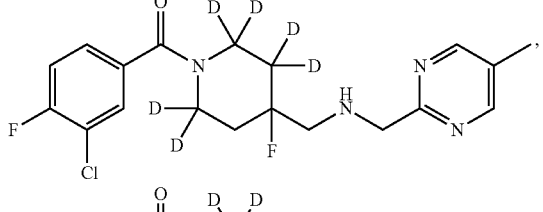
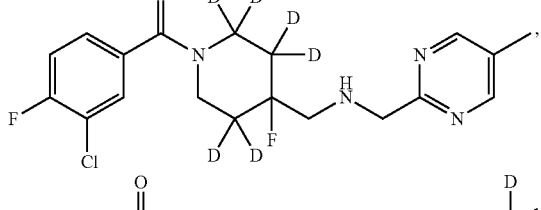
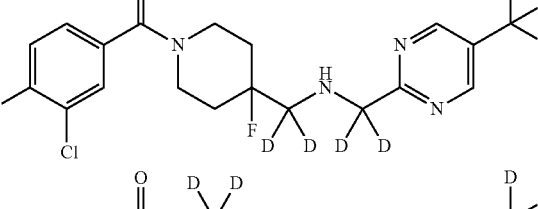
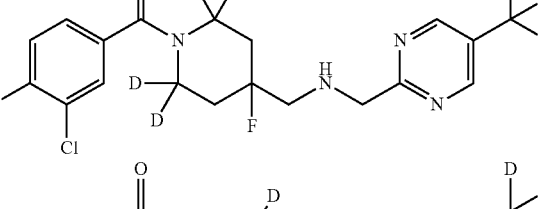
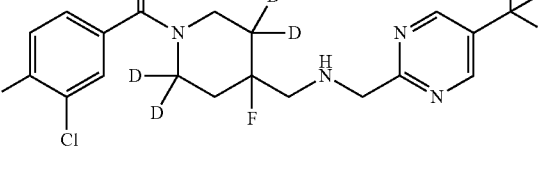

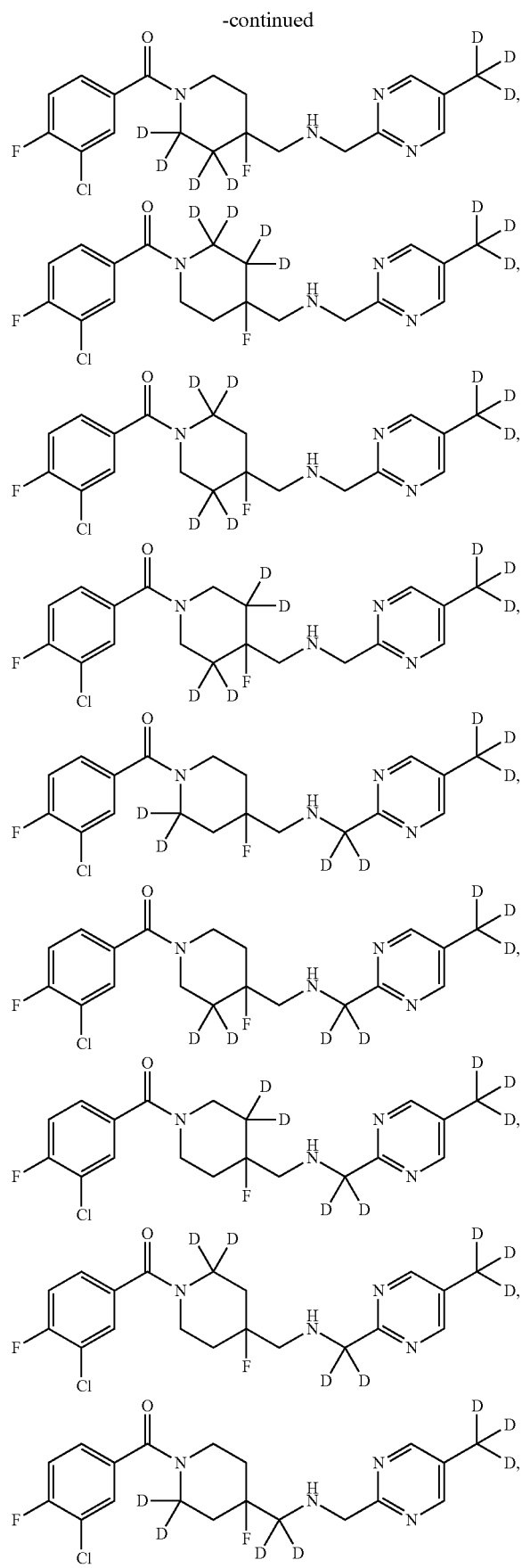
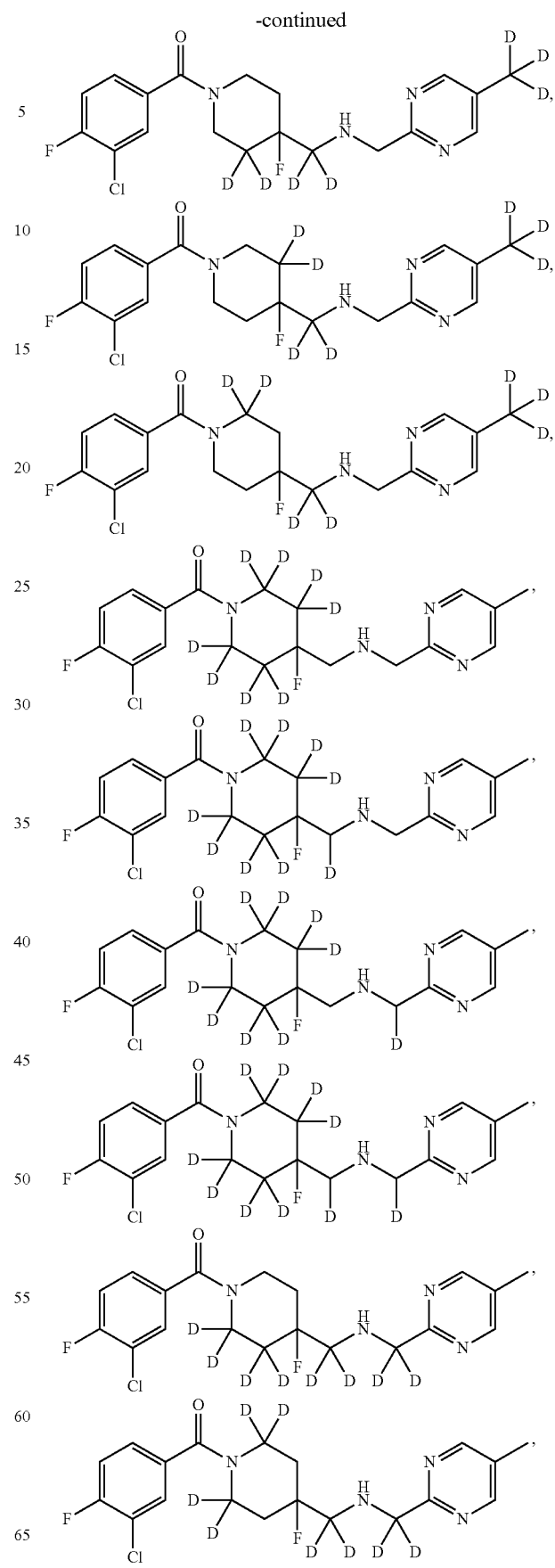

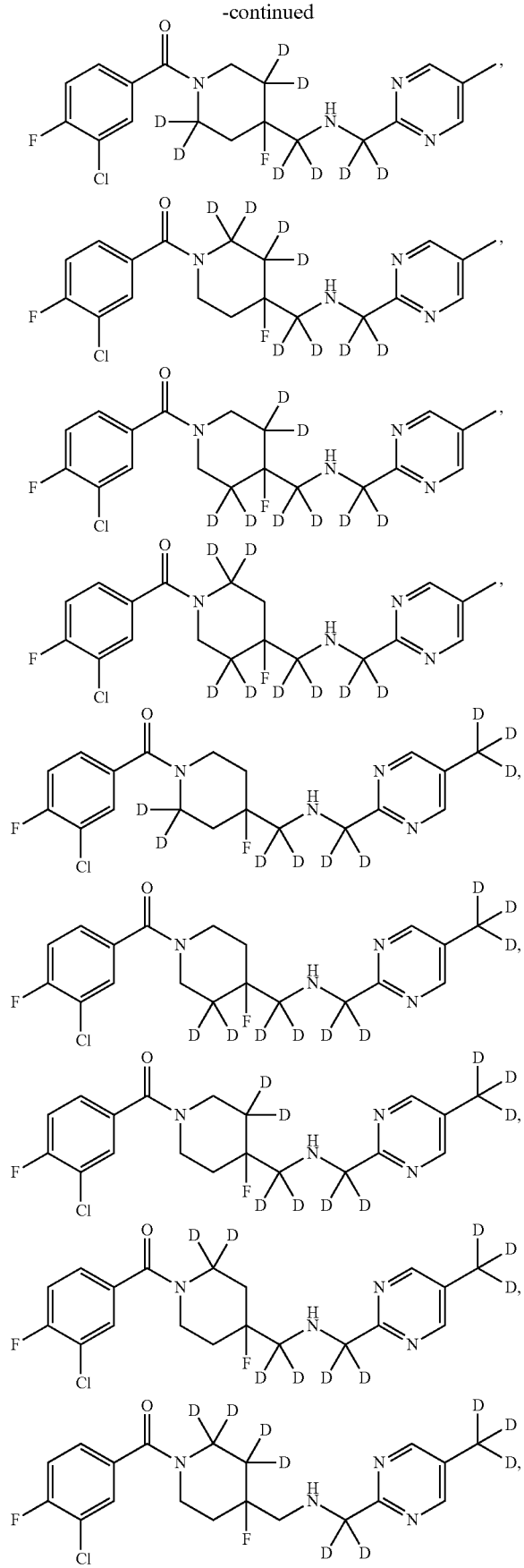
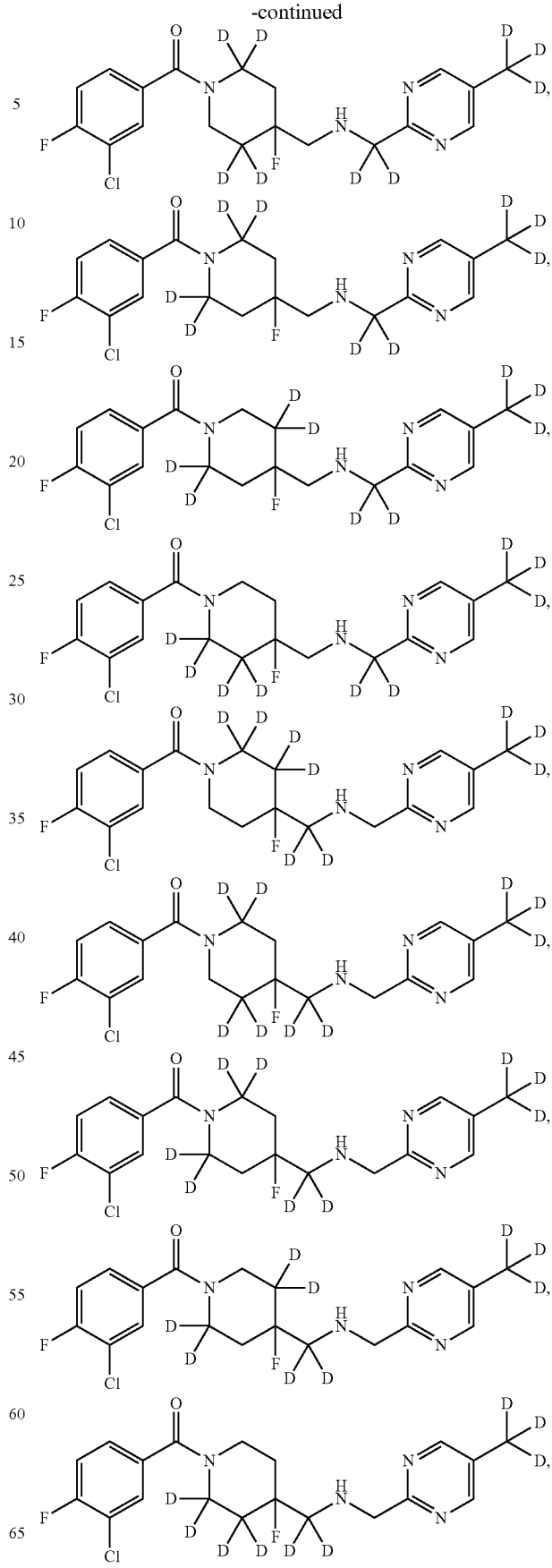

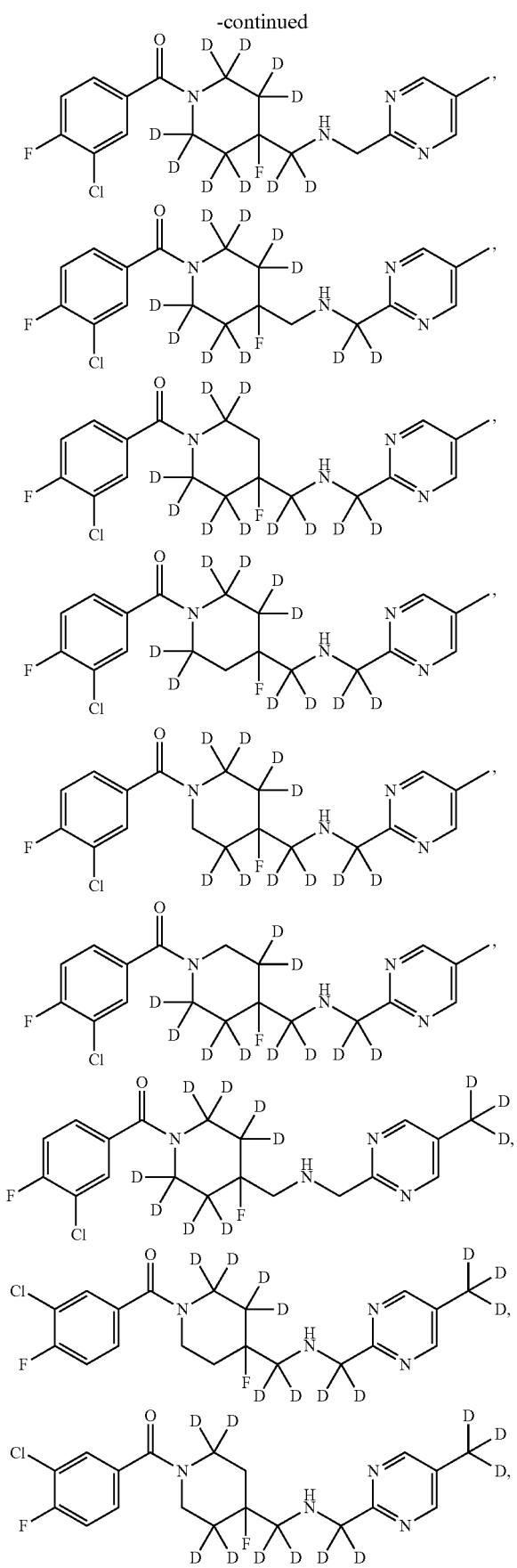
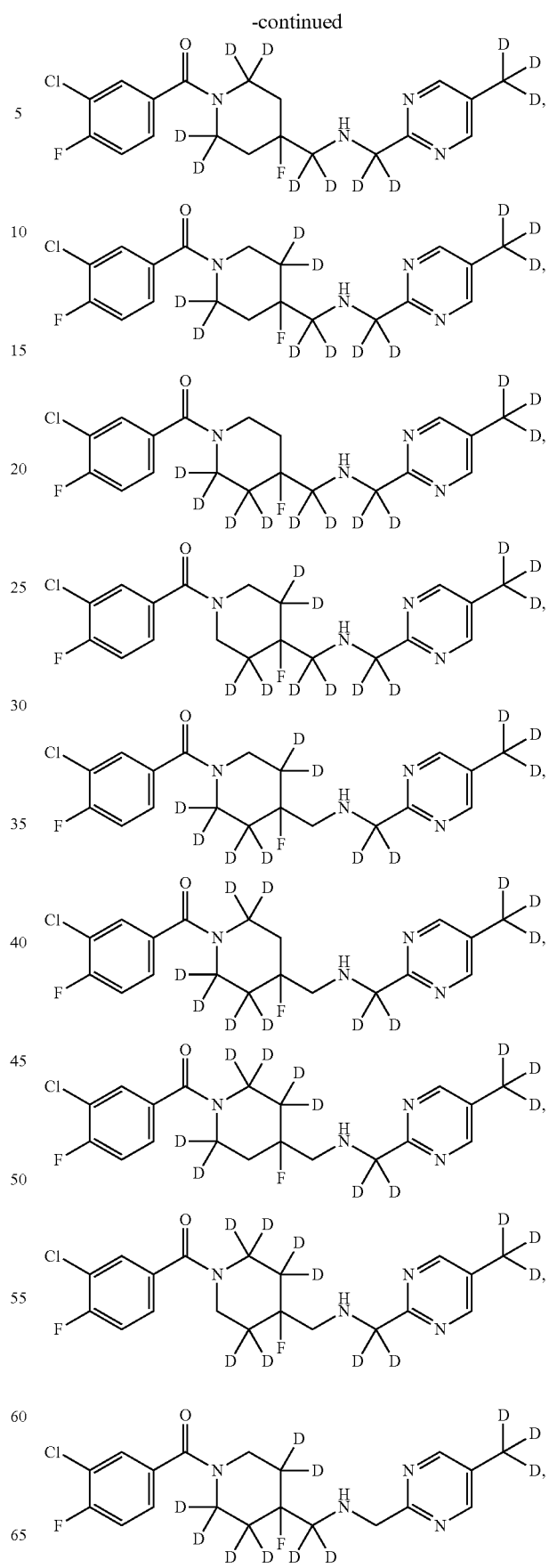

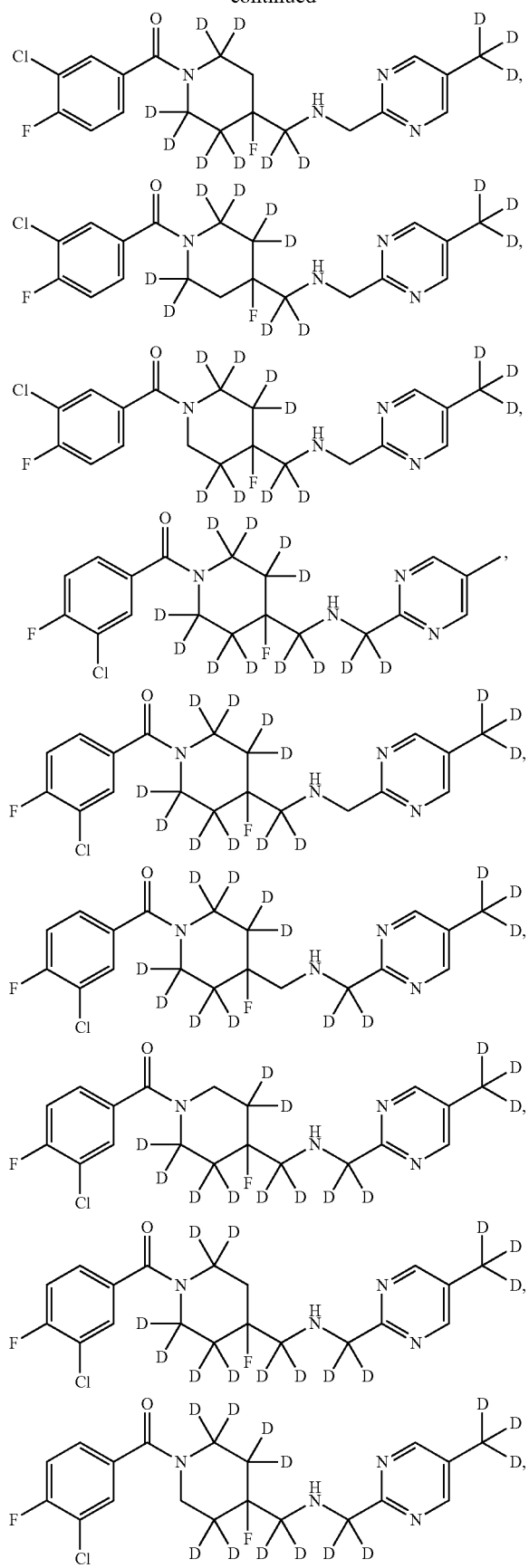

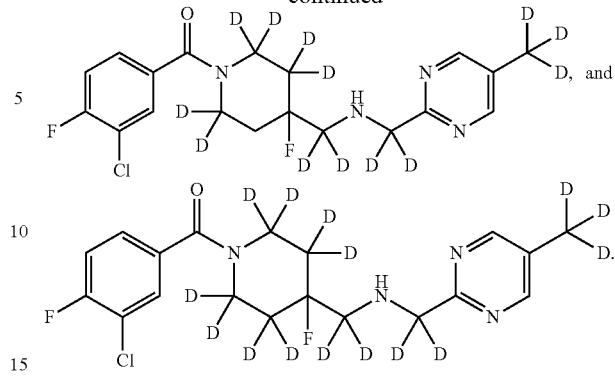

It is noted that in any of the above enumerated compounds of Formula I, the aromatic rings (i.e. the pyridine ring, the pyrimidine ring, and/or the phenyl ring) may also contain one or more deuterium.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Also provided is a pharmaceutical composition comprising a compound as disclosed herein together with a pharmaceutically acceptable carrier.

Also provided is a pharmaceutical composition comprising a pharmaceutically acceptable carrier together with a compound of Formula I:

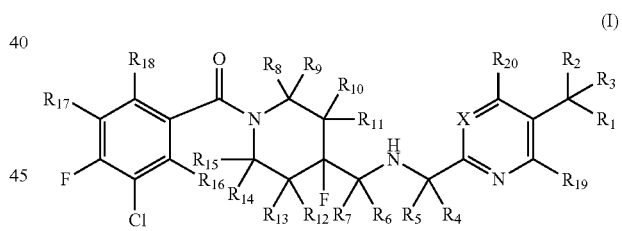

or a pharmaceutically acceptable salt, ester, prodrug, co-crystal, or solvate thereof, wherein:

X is selected from N or C—$R_{21}$; $R_1$-$R_{21}$ are independently selected from hydrogen and deuterium; and at least one of $R_1$-$R_{21}$ is deuterium.

In certain embodiments, $R_1$ is deuterium.
In certain embodiments, $R_2$ is deuterium.
In certain embodiments, $R_3$ is deuterium.
In certain embodiments, $R_4$ is deuterium.
In certain embodiments, $R_5$ is deuterium.
In certain embodiments, $R_6$ is deuterium.
In certain embodiments, $R_7$ is deuterium.
In certain embodiments, $R_8$ is deuterium.
In certain embodiments, $R_9$ is deuterium.
In certain embodiments, $R_{10}$ is deuterium.
In certain embodiments, $R_{11}$ is deuterium.
In certain embodiments, $R_{12}$ is deuterium.
In certain embodiments, $R_{13}$ is deuterium.
In certain embodiments, $R_{14}$ is deuterium.

In certain embodiments, $R_{15}$ is deuterium.
In certain embodiments, $R_{16}$ is deuterium.
In certain embodiments, $R_{17}$ is deuterium.
In certain embodiments, $R_{18}$ is deuterium.
In certain embodiments, $R_{19}$ is deuterium.
In certain embodiments, $R_{20}$ is deuterium.
In certain embodiments, $R_{21}$ is deuterium.

In further embodiments, said pharmaceutically acceptable salt is selected from a hydrochloride, a hydrobromide, a sulfate, a formate, an acetate, a trifluoroacetate, a propionate, a succinate, a fumarate, a citrate, a tartrate, a glutamate, a benzoate, a salicylate, a stearate, a lactate, a mesylate, a tosylate, a besylate, a phosphate, a maleate, and the like.

In specific embodiments, said pharmaceutically acceptable salt is selected from a sulfate and a fumarate.

In specific embodiments, at least one of $R_1$-$R_{21}$ has deuterium enrichment of at least 10%.

In some embodiments, the compounds of Formula I are effective in the treatment of movement disorders. As used herein, the term "movement disorder" refers to a group of diseases or disorders that affect the ability to produce and control body movement. Such diseases or disorders may be associated with neurological disorders or conditions associated with neurological dysfunction. Movement disorders may manifest themselves in abnormal fluency or speed of movement, excessive or involuntary movement, or slowed or absent voluntary movement. Akathisia for example, is a movement disorder characterized by unpleasant sensations of "inner" restlessness, mental unease, or dysphoria that results in inability of a patient to sit still or remain motionless. Patients having movement disorders typically have restless movement, including rocking from foot to foot and walking on the spot when standing, shuffling and tramping the legs, rocking back and forth, or swinging one leg on the other when sitting. In severe cases, patients constantly pace up and down in an attempt to relieve the sense of unrest, since the restlessness is felt from wakeup in the morning to sleep at night.

Another example of a movement disorder is dyskinesia, which is characterized by various involuntary movements which can affect discrete body parts or can become generalized and severely disabling. Tardive dyskinesia is one example of dyskinesia, which is characterized by repetitive, involuntary, purposeless movements, such as grimacing, tongue protrusion, lip smacking, puckering and pursing of the lips, and rapid eye blinking. Involuntary movements of the fingers may appear as though the patient is playing an invisible guitar or piano.

Without intending to be bound by theory, it is thought that the neurological disorder or condition which causes the movement disorder may be associated with dysfunction of the basal ganglia. The dysfunction may be idiopathic, induced by certain drugs or infections, or caused by genetic defects.

Parkinson's disease (PD) is an example of a neurological disorder associated with dysfunction of the basal ganglia. Parkinson's disease results in movement disorders and is characterized by muscle rigidity, tremor, postural abnormalities, gait abnormalities, a slowing of physical movement (bradykinesia) and, in extreme cases, a loss of physical movement (akinesia). The disease is caused by progressive death and degeneration of dopamine neurons in substantia nigra pars compacta and a dysfunctional regulation of dopamine neurotransmission. In order to replace the lost dopamine, Parkinson's disease may be treated with Levodopa (L-DOPA, a precursor of dopamine), with dopamine agonists or other agents that act by increasing the concentration of dopamine in the synaptic cleft.

Unfortunately, the treatment of Parkinson's disease with L-DOPA may give rise to dyskinesia (diminished voluntary movements and presence of involuntary movements) in advanced Parkinson's disease patients with impaired regulations of dopamine levels. This specific type of dyskinesia is called L-DOPA Induced Dyskinesia (LID).

Movement disorders induced by drug therapy can also be related to treatment of other neurological or psychiatric diseases. Examples of such movement disorders include, but are not limited to, tardive dyskinesia and akathisia, which are commonly developed as a side effect of long term treatment with neuroleptics for instance in patients suffering from e.g. schizophrenia.

In some embodiments, the compounds of Formula I are effective in the treatment of conditions or diseases known to respond to modulating the activity of $5\text{-}HT_{1A}$ receptors, including but not limited to, anxiety, depression, bipolar disorder, obsessive-compulsive disorders, panic attacks, aggression, impulsivity, alcohol abuse, sexual disorders, sleeping disorders, pain, acute pain, postoperative pain, chronic pain, nociceptive pain, cancer pain, neuropathic pain, psychogenic pain hypertension, nausea, dizziness, vomiting, regulation of gastric secretion, obesity, regulation of food intake, immune diseases, migraine, dyskinesia, akinesia, chorea, ballismus, dystonia, myoclonus, athetosis, akathisia, ataxia, synkinesia, tics, bradykinesia, tremor, movement disorders, Parkinson's disease, Huntington's disease, Tourette's syndrome, tardive dyskinesia, muscle spasms, muscle hypertonia, schizophrenia, drug-seeking behavior, opioid-induced respiratory syndrome, restless leg syndrome, L-DOPA-induced dyskinesia.

Also provided is a method of treating or preventing an $5\text{-}HT_{1A}$ receptors-mediated disorder, the method comprising administering, to a mammal in need thereof, a therapeutically effective amount of a compound of Formula I or administering a pharmaceutical composition comprising a compound of Formula I. In other embodiments, provides is a method of treating or preventing a disease selected from anxiety, depression, bipolar disorder, obsessive-compulsive disorders, panic attacks, aggression, impulsivity, alcohol abuse, sexual disorders, sleeping disorders, pain, acute pain, postoperative pain, chronic pain, nociceptive pain, cancer pain, neuropathic pain, psychogenic pain hypertension, nausea, dizziness, vomiting, regulation of gastric secretion, obesity, regulation of food intake, immune diseases, migraine, dyskinesia, akinesia, chorea, ballismus, dystonia, myoclonus, athetosis, akathisia, ataxia, synkinesia, tics, bradykinesia, tremor, movement disorders, Parkinson's disease, Huntington's disease, Tourette's syndrome, tardive dyskinesia, muscle spasms, muscle hypertonia, schizophrenia, drug-seeking behavior, opioid-induced respiratory syndrome, restless leg syndrome, and L-DOPA-induced dyskinesia, the method comprising administering a therapeutically effective amount of at least one compound of Formula I to a mammal in need thereof.

In certain embodiments, the method further results in at least one effect selected from the group consisting of:
  a) decreased inter-individual variation in plasma levels of said compound or a metabolite thereof as compared to the non-isotopically enriched compound;
  b) increased average plasma levels of said compound per dosage unit thereof as compared to the non-isotopically enriched compound;

c) decreased average plasma levels of at least one metabolite of said compound per dosage unit thereof as compared to the non-isotopically enriched compound;
d) increased average plasma levels of at least one metabolite of said compound per dosage unit thereof as compared to the non-isotopically enriched compound; and
e) an improved clinical effect during the administration in said subject per dosage unit thereof as compared to the non-isotopically enriched compound.

In certain embodiments, the method further results in at least two effects selected from the group consisting of:
a) decreased inter-individual variation in plasma levels of said compound or a metabolite thereof as compared to the non-isotopically enriched compound;
b) increased average plasma levels of said compound per dosage unit thereof as compared to the non-isotopically enriched compound;
c) decreased average plasma levels of at least one metabolite of said compound per dosage unit thereof as compared to the non-isotopically enriched compound;
d) increased average plasma levels of at least one metabolite of said compound per dosage unit thereof as compared to the non-isotopically enriched compound; and
e) an improved clinical effect during the administration in said subject per dosage unit thereof as compared to the non-isotopically enriched compound.

In certain embodiments, the method affects a decreased metabolism of the compound per dosage unit thereof by at least one polymorphically-expressed cytochrome $P_{450}$ isoform in the subject, as compared to the corresponding non-isotopically enriched compound.

In certain embodiments, said compound is characterized by decreased inhibition of at least one cytochrome $P_{450}$ or monoamine oxidase isoform in said subject per dosage unit thereof as compared to the non-isotopically enriched compound.

In certain embodiments, said cytochrome $P_{450}$ or monoamine oxidase isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, $MAO_A$, and $MAO_B$.

In certain embodiments, the method reduces a deleterious change in a diagnostic hepatobiliary function endpoint, as compared to the corresponding non-isotopically enriched compound.

In certain embodiments, the diagnostic hepatobiliary function endpoint is selected from the group consisting of alanine aminotransferase ("ALT"), serum glutamic-pyruvic transaminase ("SGPT"), aspartate aminotransferase ("AST," "SGOT"), ALT/AST ratios, serum aldolase, alkaline phosphatase ("ALP"), ammonia levels, bilirubin, gamma-glutamyl transpeptidase ("GGTP," "γ-GTP," "GGT"), leucine aminopeptidase ("LAP"), liver biopsy, liver ultrasonography, liver nuclear scan, 5'-nucleotidase, and blood protein.

With respect to the terms used in this disclosure, the following definitions are provided.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ . . . to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

As used herein, the term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

As used herein, the term "is/are deuterium," when used to describe a given position in a molecule such as $R_1$-$R_{21}$ or the symbol "D," when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

As used herein, the term "isotopic enrichment" refers to the percentage of incorporation of a less prevalent isotope of an element at a given position in a molecule in the place of the more prevalent isotope of the element.

As used herein, the term "non-isotopically enriched" refers to a molecule in which the percentages of the various isotopes are substantially the same as the naturally occurring percentages.

Asymmetric centers may exist in the compounds disclosed herein. Compounds of the present invention containing an asymmetrically substituted atom may be isolated in optically active or racemic forms. It is well known in the art how to prepare optically active forms, such as by resolution of racemic forms or by synthesis from optically active materials. Asymmetric centers are designated by the symbols "R" or "S," depending on the configuration of substituents around the chiral carbon atom. It should be understood that the invention encompasses all chiral, diastereomeric, racemic forms, and all geometric isomeric forms, and mixtures thereof, unless the specific stereochemistry or isomeric form is specifically indicated. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

As used herein, the term "substituted" means that any one or more hydrogens on the designated atom or ring is replaced with a selection from the indicated group, e.g. deuterium, provided that the designated atom's normal valency is not exceeded.

As used herein, the term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

As used herein, the term "disorder" is intended to be generally synonymous, and is used interchangeably with, the terms "disease" and "condition" (as in medical condition), in that all reflect an abnormal condition of the human or animal body or of one of its parts that impairs normal functioning, is typically manifested by distinguishing signs and symptoms.

As used herein, the terms "treat," "treating," and "treatment" are meant to include alleviating or abrogating a disorder or one or more of the symptoms associated with a disorder; or alleviating or eradicating the cause(s) of the disorder itself. In some embodiments, treating refers to inhibiting the disease-state, i.e., arresting its development and/or relieving the disease-state, i.e., causing regression of the disease state.

As used herein, the terms "prevent," "preventing," and "prevention" refer to a method of delaying or precluding the onset of a disorder; and/or its attendant symptoms, barring a subject from acquiring a disorder or reducing a subject's risk of acquiring a disorder. In some embodiments, preventing refers to precluding a disease-state from occurring in a mammal, in particular, when such mammal is pre-disposed to the disease-state but has not yet been diagnosed as having it.

As used herein, the term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

As used herein, the term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human and/or a canine and/or a feline patient.

As used herein, the term "combination therapy" refers to the administration of two or more therapeutic agents to treat (or prevent) a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment (or prevention) regimen will provide beneficial effects of the drug combination in treating the disorders described herein.

As used herein, the term "5-$HT_{1A}$ receptors-mediated disorder" refers to a disorder that is characterized by abnormal 5-$HT_{1A}$ receptor activity, that when modulated ameliorates other abnormal biochemical processes. A 5-$HT_{1A}$ receptors-mediated disorder may be completely or partially mediated by modulating the activity of 5-$HT_{1A}$ receptors. In particular, a 5-$HT_{1A}$ receptor-mediated disorder is one in which the modulation of 5-$HT_{1A}$ receptor activity results in some effect on the underlying disorder, e.g., administration of 5-$HT_{1A}$ receptor agonist results in some improvement in at least some of the patients being treated.

As used herein, the term "5-$HT_{1A}$ receptor agonist" refers to the ability of a compound disclosed herein to alter the function of at least one 5-$HT_{1A}$ receptor. A 5-$HT_{1A}$ receptor agonist may trigger the release or inhibition of norepinephrine. A 5-$HT_{1A}$ receptor agonist may also increase dopamine release in the media prefrontal cortex, stiatum, and hippocampus. In some instances, a 5-$HT_{1A}$ receptor agonist may induce the secretion of various hormones including cortisol, corticosterone, adrenocorticotropic hormone (ACTH), oxytocin, prolactin, growth hormone, and β-endorphin.

As used herein, the term "modulating 5-$HT_{1A}$ receptor activity" or the like refers to altering the function of at least one 5-$HT_{1A}$ receptor by administering a 5-$HT_{1A}$ receptor agonist.

As used herein, the terms "therapeutically acceptable" and "pharmaceutically acceptable" are used interchangeably and refer to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

As used herein, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio.

As used herein, the terms "active ingredient," "active compound," and "active substance" refer to a compound, which is administered, alone or in combination with one or more pharmaceutically acceptable excipients or carriers, to a subject for treating, preventing, or ameliorating one or more symptoms of a disorder.

As used herein, the terms "drug," "therapeutic agent," and "chemotherapeutic agent" refer to a compound, or a pharmaceutical composition thereof, which is administered to a subject for treating, preventing, or ameliorating one or more symptoms of a disorder.

As used herein, the term "release controlling excipient" refers to an excipient whose primary function is to modify the duration or place of release of the active substance from a dosage form as compared with a conventional immediate release dosage form.

As used herein, the term "nonrelease controlling excipient" refers to an excipient whose primary function do not include modifying the duration or place of release of the active substance from a dosage form as compared with a conventional immediate release dosage form.

As used herein, the term "prodrug" refers to a compound functional derivative of the compound as disclosed herein and is readily convertible into the parent compound in vivo. The term "prodrug" denotes a compound which, upon administration to a subject, undergoes chemical conversion by metabolic or chemical processes to yield a compound of the formula, and/or a salt and/or solvate thereof. For example, compounds containing a carboxy group can form physiologically hydrolyzable esters which serve as prodrugs by being hydrolyzed in the body to yield formula compounds per se. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

The term "prodrug" as employed herein includes esters and carbonates formed by reacting compounds of formula I with alkyl, alkoxy, or aryl substituted acylating agents employing procedures known to those skilled in the art to generate acetates, pivalates, methyl carbonates, benzoates, and the like.

As used herein, the term "co-crystal" refers to materials (i.e. solids) that are crystalline single phase materials composed of two or more different molecular and/or ionic compounds generally in a stoichiometric ratio which are neither solvates nor simple salts.

The compounds disclosed herein can exist as therapeutically acceptable salts or pharmaceutically acceptable salts. As used herein, the terms "therapeutically acceptable salt" and "pharmaceutically acceptable salt" are used interchangeably and represent salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts.

The term pharmaceutically acceptable salt includes acid addition salts. There are formed, for example, with strong inorganic acids, such as mineral acids or a hydrohalic acid, with strong organic carboxylic acid, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, benzoic acid, or organic sulfonic acids.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecyl sulfuric acid, ethane-1,2-disulfonic acid, ethanesulfonic acid, 2-hydroxy-ethanesulfonic acid, formic acid, fumaric acid, phthalic acid, terephthalic acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Such pharmaceutically acceptable salts may refer to basic salts formed with inorganic and organic bases. Such salts include ammonium salts; alkali metal salts, such as lithium, sodium, and potassium salts; alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In specific embodiments, fumaric acid (trans-butendioic acid) is used for the preparation of a pharmaceutically acceptable salt. The resulting salt is, thus, a fumarate. In other specific embodiments, sulfuric acid is used for the preparation of a pharmaceutically acceptable salt. The resulting salt is, thus, a sulfate. In further embodiments, the pharmaceutically acceptable salt is selected from selected from a hydrochloride, a hydrobromide, a sulfate, a formate, an acetate, a trifluoroacetate, a propionate, a succinate, a fumarate, a citrate, a tartrate, a glutamate, a benzoate, a salicylate, a stearate, a lactate, a mesylate, a tosylate, a besylate, a phosphate, a maleate, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

As used herein, the terms "therapeutically effective amount" and "pharmaceutically effective amount" are intended to include an amount of a compound of the present invention alone or an amount of the combination of compounds claimed or an amount of a compound of the present invention in combination with other active ingredients effective to treat or prevent a 5-$HT_{1A}$ receptor-mediated disorder.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. Such carriers enable the pharmaceutical compositions to be formulated as tablets, pills dragees, capsules, liquids, gels, syrups, slurries, suspensions, and the like, for ingestion, application, or inhalation by the patient. In addition to the active ingredients (e.g. the compounds of structural Formula I), the pharmaceutical compositions may contain suitable pharmaceutically acceptable carriers comprising excipients and auxiliaries which facilitate processing of the active compounds into preparations which can be used pharmaceutically. Techniques for formulation and administration are known in the art.

The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art.

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. Such compositions may be present in the form of a gel, paste, ointment, cream, lotion, liquid suspension, dispersion, emulsions, micro-emulsions, microcapsules, microparticles, vesicular dispersions, and the like.

The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment (i.e., administration) on a long-term basis upon any recurrence of symptoms.

Disclosed herein are methods of treating a $5\text{-HT}_{1A}$ receptor-mediated disorder comprising administering to a subject having or suspected of having such a disorder, a therapeutically effective amount of a compound as disclosed herein or a pharmaceutically acceptable salt, solvate, or prodrug thereof.

Without intending to be bound by theory, it is thought that the compounds of Formula I target and modulate the activity of $5\text{-HT}_{1A}$ receptors. Thus, one or more embodiments are directed to modulating the activity of $5\text{-HT}_{1A}$ receptors in order to treat or prevent a $5\text{-HT}_{1A}$ receptor-mediated disorder.

$5\text{-HT}_{1A}$ receptor-mediated disorders, include, but are not limited to, anxiety, depression, bipolar disorder, obsessive-compulsive disorders, panic attacks, aggression, impulsivity, alcohol abuse, sexual disorders, sleeping disorders, pain, acute pain, postoperative pain, chronic pain, nociceptive pain, cancer pain, neuropathic pain, psychogenic pain hypertension, nausea, dizziness, vomiting, regulation of gastric secretion, obesity, regulation of food intake, immune diseases, migraine, dyskinesia, akinesia, chorea, ballismus, dystonia, myoclonus, athetosis, akathisia, ataxia, synkinesia, tics, bradykinesia, tremor, movement disorders, Parkinson's disease, Huntington's disease, Tourette's syndrome, tardive dyskinesia, muscle spasms, muscle hyptertonia, schizophrenia, drug-seeking behavior, opioid-induced respiratory syndrome, restless leg syndrome, L-DOPA-induced dyskinesia, and/or any disorder which can lessened, alleviated, or prevented by administering a 5-HT$_{1A}$ receptor agonist.

In certain embodiments, a method of treating a 5-HT$_{1A}$ receptor-mediated disorder comprises administering to the subject a therapeutically effective amount of a compound as disclosed herein, or a pharmaceutically acceptable salt, ester, solvate, co-crystal, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome P$_{450}$ or monoamine oxidase isoform in the subject; (4) decreased metabolism via at least one polymorphically-expressed cytochrome P$_{450}$ isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome P$_{450}$ or monoamine oxidase isoform by a compound as disclosed herein is decreased; or metabolism of the compound as disclosed herein by at least one polymorphically-expressed cytochrome P$_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described the art.

Examples of cytochrome P$_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R$_1$, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, MAO$_A$, and MAO$_B$.

The inhibition of the cytochrome P$_{450}$ isoform is measured by the method of Ko et al. (*British Journal of Clinical Pharmacology*, 2000, 49, 343-351). The inhibition of the MAO$_A$ isoform is measured by the method of Weyler et al. (*J. Biol. Chem.* 1985, 260, 13199-13207). The inhibition of the MAO$_B$ isoform is measured by the method of Uebelhack et al. (*Pharmacopsychiatry*, 1998, 31, 187-192).

Examples of polymorphically-expressed cytochrome P$_{450}$ isoforms in a mammalian subject include, but are not limited to, CYP1A2, CYP2C8, CYP2C9, CYP2C19, CYP2D6, CYP3A4, and CYP3A5.

The metabolic activities of liver microsomes, cytochrome P$_{450}$ isoforms, and monoamine oxidase isoforms are measured by the methods described herein.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

Patients being treated by administration of the 5-HT$_{1A}$ receptor agonists of Formula I often exhibit diseases or conditions that may benefit from treatment with other therapeutic agents. These diseases or conditions can be of psychological or movement based or can be related to cardiovascular disorders, metabolic disorders, pulmonary disorders, metabolic disorders, gastrointestinal disorders, and the like. Additionally, some patients being treated by administration of the 5-HT$_{1A}$ receptor agonists of Formula I exhibit conditions that can benefit from treatment with therapeutic agents that are antibiotics, analgesics, and/or antidepressants and anti-anxiety agents.

The present invention includes within its scope pharmaceutical compositions comprising, as an active ingredient, a therapeutically effective amount of at least one compound of Formula I, alone or in combination with a pharmaceutical carrier or diluent. Optionally, compounds of the present invention can be used alone, in combination with other compounds of the invention (i.e. additional compounds of Formula I), or in combination with one or more other therapeutic agent(s).

In certain embodiments, the method comprises administering, or co-administering, an additional therapeutic agent in combination with one or more compounds of Formula I. The compounds disclosed herein may also be combined or used in combination with other agents useful in the treatment or prevention of 5-HT$_{1A}$ receptor-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

Thus, in another aspect, embodiments provide methods for treating 5-HT$_{1A}$ receptor-mediated disorders in a human or animal comprising administering to said subject an amount of a compound of formula I disclosed herein effective to reduce or prevent said 5-HT$_{1A}$ receptor-mediated disorder in the subject, in combination with at least one additional therapeutic agent for the treatment of said disorder. In a related aspect, embodiments provide pharmaceutical compositions comprising at least one compound disclosed herein in combination with one or more additional therapeutic agents for the treatment of 5-HT$_{1A}$ receptor-mediated disorders.

In certain embodiments, the compounds of Formula I disclosed herein can be combined with one or more additional 5-HT$_{1A}$ receptor agonist (full or partial agonist) including, but not limited to, aripiprazole, alnespirone, asenapine, bacoside, amphetamine, adatanserin, befiradol, binospirone, bufotenin, buspirone, cannabidiol, clozapine, dihydroergotamine, ebalzotan, eltoprazine, ergotamine, etoperidone, flesinoxan, flibanserin, gepirone, haloperidol, lamotrigine, ipsapirone, lisuride, lurasidone, methylphenidate, naluzotan, nefazodone, olanzapine, osemozotan, perospirone, piclozotan, psilocin, psilocybin, quetiapine, rauwolscine, repinotan, sarizotan, sunepitron, tandospirone, tiospirone, trazodone, urapidil, vortioxetine, vilazodone, zalospirone, ziprasidone, osemozotan, repinotan, lesopitron, eptapirone, and alnespirone.

In certain embodiments, the compounds of Formula I disclosed herein can be combined with one or more 5-HT$_{1B}$, 5-HT$_{1D}$ and 5-HT$_{1F}$ receptor agonist, including, but not limited to, ergotamine, oxymetazoline, sumatriptan, zolmitriptan, 5-carboxamidotryptamine, vortioxetine, ziprasidone, asenapine, 5-(nonyloxy)tryptamine, 5-(t-butyl)-N-methyltryptamine, 5-n-butyrloxy-DMT, eletriptan, and naratriptan.

In certain embodiments, the compounds of Formula I disclosed herein can be combined with one or more agents selected from the group of agents increasing the dopamine concentration of the synaptic cleft (i.e. dopamine reuptake inhibitors), including, but not limited to, amineptine, dexmethylphenidate, difemetorex, fencamfamine, lefetamine, levophacetoperane, medifoxamine, mesocarb, methylphenidate, nomifensine, pipradrol, prolintane, pyrovalerone, ketamine, dopamine, L-DOPA, or a dopamine receptor agonist, including, but not limited to, aripiprazole, quinpirole, apomorphine, bromocriptine, cabergoline, ciladopa, dihydrexidine, dinapsoline, doxanthrine, epicriptine, lisuride, pergolide, piribedil, pramipexole, propylnorapomorphine, quinagolide, ropinirole, rotigotine, roxindole, and sumanirole.

In certain embodiments, the compounds of Formula I disclosed herein can be combined with one or more antidepressant and antianxiety agents including, without limitation, sertraline, citalopram, fluoxetine, escitalopram, trazodone, venlafaxine, desvenlafaxine, bupropion, duloxetine, paroxetine, amitriptyline, mirtazapine, nefazodone, nortriptyline, alprazolam, bromazepam, chlordiazepoxide, clonazepam, clorazepate, diazepam, flurazepam, lorazepam, oxazepam, temazepam, triazolam, tofisopam, meprobamate, carisoprodol, tybamate, lorbamate, and the like.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepam; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In some embodiments, a patient presenting with a psychological disorder or a movement disorder or related condition may suffer from secondary medical conditions such as one or more of a cardiovascular disease, a metabolic disorder, a pulmonary disorder, a peripheral vascular disorder, a gastrointestinal disorder, or a pain disorder. Such patients may benefit from a treatment of a combination therapy comprising administration to the patient one or more compounds of Formula I in combination with at least one additional therapeutic agent.

Cardiovascular related diseases or conditions that a patient may present with include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension and chronic thromboembolic pulmonary hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions in combination with compounds of Formula I disclosed herein include anti-anginals, heart failure agents, antithrombotic agents, antiarrhythmic agents, antihypertensive agents, and lipid lowering agents.

Anti-anginals include beta-blockers, calcium channel blockers, and nitrates. Examples of beta-blockers include, but are not limited to, metoprolol (Lopressor®, Toprol® XL), carteolol (Cartrol®), acebutolol (Sectral®), betaxolol (Kerlone®), atenolol (Tenormin®), bisoprolol/hydrochlorothiazide (Ziac®), bisoprolol (Zebeta®), esmolol (Brevibloc®), labetalol (Normodyne®, Trandate®), nadolol (Corgard®), propranolol (Inderal®), sotalol (Betapace®), and timolol (Blocadren®).

Examples of nitrates include, but are not limited to, nitroglycerin, nitrate patches, isosorbide dinitrate, and isosorbide-5-mononitrate.

Examples of calcium channel blockers include, but are not limited to, bepridil (Vascor®), amlodipine (Norvasc®, Lotrel®), diltiazem (Cardizem®, Tiazac®), nifedipine (Adalat®, Procardia®), felodipine (Plendil®), nisoldipine (Sular®), nimodipine (Nimotop®), verapamil (Verelan®, Calan®, Isoptin®), and nicardipine.

Agents used to treat heart failure include ACE inhibitors, diuretics, vasodilators, and cardiac glycosides. Examples of ACE inhibitors include, but are not limited to, benazepril (Lotensin®), captopril (Capoten®), enalapril (Vasotec®), fosinopril (Monopril®), Lisinopril (Prinivil®, Zestril®), moexipril (Univasc®), perindopril (Aceon®), quinapril (Accupril®), ramipril (Altace®), and trandolapril (Mavik®).

Examples of diuretics include, but are not limited to, furosemide (Lasix®), metolazone (Zaroxolyn®), bumetanide (Bumex®), spironolactone (Aldactone®), eplerenone (Inspra®), and hydrochlorothiazide.

Examples of vasodilators include, but are not limited to, hydralazine, diazoxide, prazosin, clonidine, and methyldopa. Nitrates, ACE inhibitors, potassium channel activators, and calcium channel blockers may also act as vasodilators.

Examples of cardiac glycosides include, but are not limited to, digoxin, digitoxin, and digitalis.

Examples of antithrombotics include, but are not limited to, platelet inhibitors, anticoagulants, and thrombolytic agents.

Examples of platelet inhibitors include, but are not limited to, clopidogrel (Plavix®), ticlopidine, acetyl salicylic acid (aspirin), prasugrel (Effient®), cilostazol, dipyridamole, persantine sulfinpyrazone, indomethacin, and glycoprotein llb/lla inhibitors (such as abciximab, tirofiban, and eptifibatide (Integrelin®).

Examples of anticoagulants include, but are not limited to, warfarin (Coumadin®), unfractionated heparin, low molecular weight heparin, danaparoid, lepirudin, argatroban, bivalirudin, apixaban (Eliquis®), rivaroxaban, and edoxaban.

Examples of thrombolytic agents include, but are not limited to, tissue plasminogen activator (t-PA), tenecteplase (TNK), streptokinase, and urokinase.

Antiarrhythmic agents include, but are not limited to, quinidine, procainamide, amiodarone, dronedarone, lidocaine, and propafenone.

Antihypertensive agents include, but are not limited to, alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopres-sor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid lowering agents can include, but are not limited to bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®), pravastatin (Lipostat®), rosuvastatin (Crestor®), and simvastatin (Zocor®).

As used herein, examples of metabolic disorders include, but are not limited to, diabetes (including type I and type II diabetes), metabolic syndrome, dyslipidemia, obesity, glucose intolerance, polycystic ovarian syndrome (PCOS), hypertension, elevated serum cholesterol, and elevated triglycerides.

Examples of therapeutic agents that may be used to treat metabolic disorders included, but are not limited to, antihypertensive agents, lipid lowering agents, insulin, sulfonylureas, biguanides, alpha-glucosidase inhibitors, and incretin mimetics.

As used herein, the term "pulmonary disorder" refers to any disease or condition related to the lungs. Examples of pulmonary disorders include, but are not limited to, asthma, chronic obstructive pulmonary disease (COPD), pulmonary hypertension, emphysema, and bronchitis.

Examples of therapeutic agents that may be used to treat pulmonary disorders include, but are not limited to, corticosteroids, bronchodilators, and electrolyte supplements.

As used herein, the term "gastrointestinal disorder" refers to diseases and conditions associated with the gastrointestinal tract, including, but not limited to, gastroesophageal reflux disease (GERD), inflammatory bowel disease (IBD), gastroenteritis, peptic ulcer disease, pancreatitis, and gastritis.

Examples of therapeutic agents that may be used to treat gastrointestinal disorders include, but are not limited to, proton pump inhibitors, H2 blockers, prostaglandins, and antacids.

As used herein, the term "peripheral vascular disorder" refers to disorders related to the blood vessels (arteries and veins) located outside the heart and the brain, including, but not limited to, peripheral arterial disease (PAD).

Pain disorders or conditions that can benefit from a combination treatment of the 5-HT$_{1A}$ receptor agonists of Formula I with other therapeutic agents include, without limitation, pain, acute pain, postoperative pain, chronic pain, nociceptive pain, cancer pain, neuropathic pain, psychogenic pain, and the like. Agents used to treat such pain disorders include, without limitation, cyclooxygenase-2 (COX-2) inhibitors, such as celecoxib, valdecoxib, rofecoxib, and the like; opioids, such as tramadol, and the like; serotonin-norepinephrine reuptake inhibitors (SNRIs), such as milnacipran, and the like; norepinephrine-dopamine reuptake inhibitor (NDRIs), such as bupropion, and the like; serotonin-norepinephrine-dopamine-reuptake-inhibitors (SNDRIs), such as venlafaxine, and the like; norepinephrine reuptake inhibitors (NRIs) such as atomoxetine, and the like; dopamine reuptake inhibitors (DARIs), such as methylphenidate, and the like; nonsteroidal anti-inflammatory (NSAID) agents, such as acetylsalicylic acid, naproxen, ibuprofen, indomethacine, and the like; acetaminophen; and other agents known in the treatment of pain.

In other embodiments, a patient presenting with a psychological disorder or a movement disorder or the like may suffer from second medical conditions and/or symptoms that may benefit from the administration of one or more additional therapeutic agents including, but not limited to antibiotics, analgesics, antidepressants, and anti-anxiety agents.

The methods of combination therapy include co-administration of a formulation containing one or more 5-HT$_{1A}$ receptor agonists of Formula I and at least one additional therapeutic agent, essentially contemporaneous administration of more than one formulation comprising the 5-HT$_{1A}$ receptor agonist of Formula I and the additional therapeutic agents or agents, and consecutive administration Thus, in another aspect, certain embodiments provide methods for treating 5-HT$_{1A}$ receptor-mediated disorders in a human or animal comprising administering to said subject an amount of a compound disclosed herein effective to reduce or prevent said disorder in the subject, in combination with at least one additional agent for the treatment of said disorder. In a related aspect, certain embodiments provide therapeutic pharmaceutical compositions comprising at least one compound disclosed herein in combination with one or more additional agents for the treatment of 5-HT$_{1A}$ receptor-mediated disorders.

General Synthetic Methods for Preparing Compounds

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds of Formula I as disclosed herein can be prepared by methods known to one of skill in the art and routine modifications thereof, and/or following procedures similar to those described in the Example section herein and routine modifications thereof, and/or procedures found in U.S. Pat. Nos. 6,020,345, and 7,208,603, which are hereby incorporated in their entirety, and references cited therein and routine modifications thereof. Compounds as disclosed herein can also be prepared as shown in any of the following schemes and routine modifications thereof.

Compounds of Formula I may be prepared as shown in the following reaction schemes and the description thereof, as well as relevant literature procedures that may be used by one skilled in the art. Exemplary reagents and procedures for these reactions appear hereinafter and in the working Examples. Any position shown as hydrogen may optionally be replaced with deuterium.

Specifically, compounds of Formula I, wherein X is C—R$_{21}$ may be prepared as showing in the following reaction Schemes I-IV and the description thereof, as well as relevant literature procedures that may be used by one skilled in the art. Exemplary reagents and procedures for these reactions appear hereinafter and in the working Examples. Any position shown as hydrogen may optionally be replaced with deuterium.

Scheme I

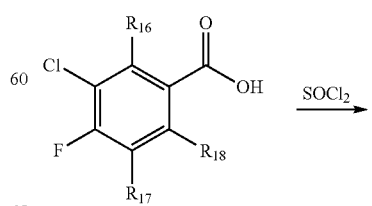

1

59
-continued
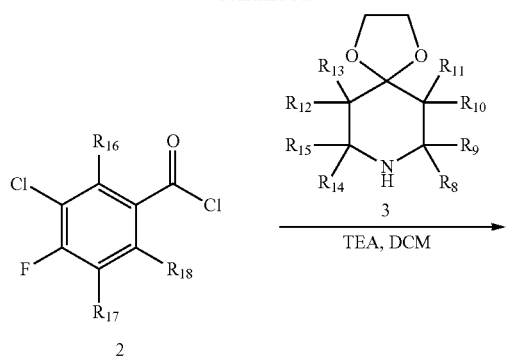
2
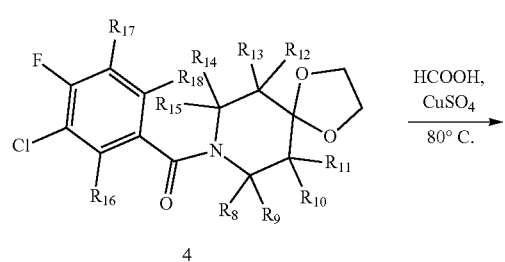
4
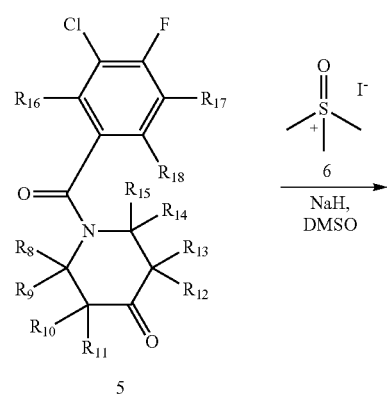
5
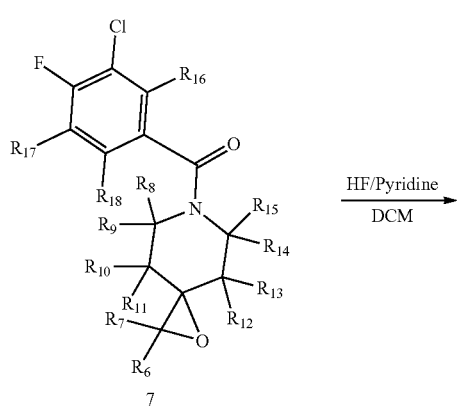
7
60
-continued
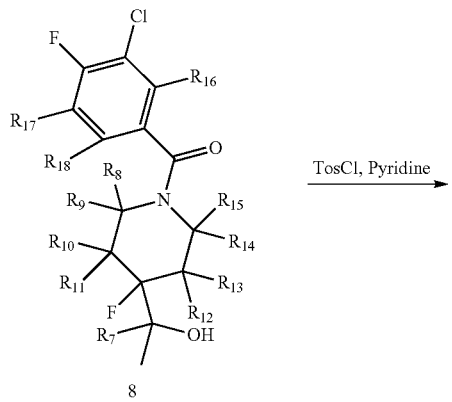
8
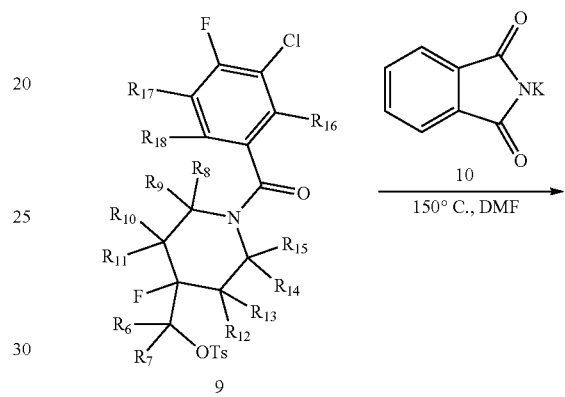
9
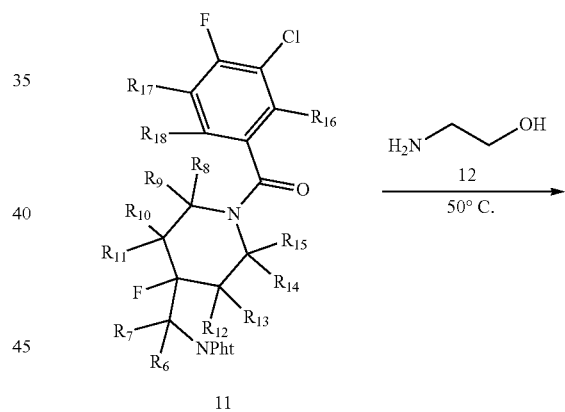
11
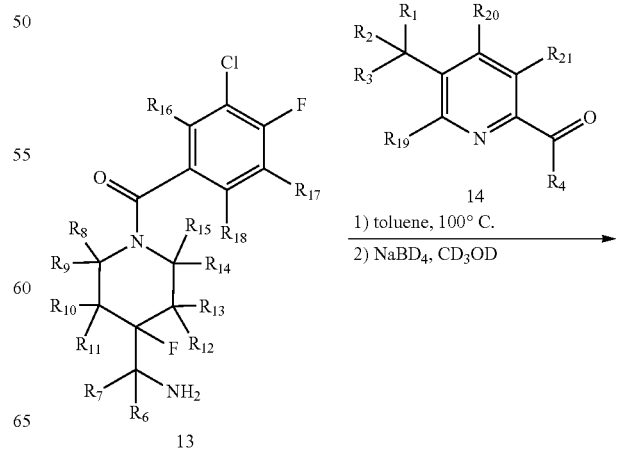
13

-continued

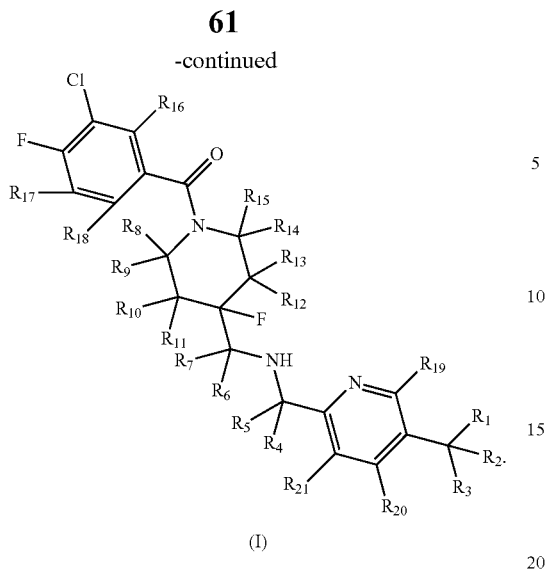

(I)

Deuterium can be incorporated into different positions synthetically, according to the synthetic procedures as shown in Scheme I, by using appropriate deuterated intermediates. For example, to introduce deuterium at one or more positions of $R_8$-$R_{15}$, compound 3 with the corresponding deuterium substitutions can be used. To introduce deuterium at one or more positions of $R_1$-$R_5$ and $R_{19}$-$R_{21}$, compound 14 with the corresponding deuterium substitutions can be used.

Scheme II

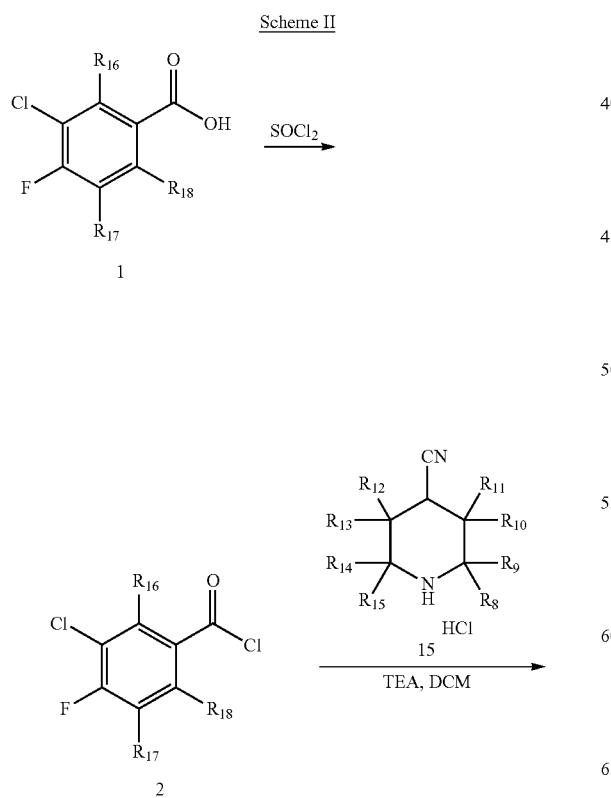

-continued

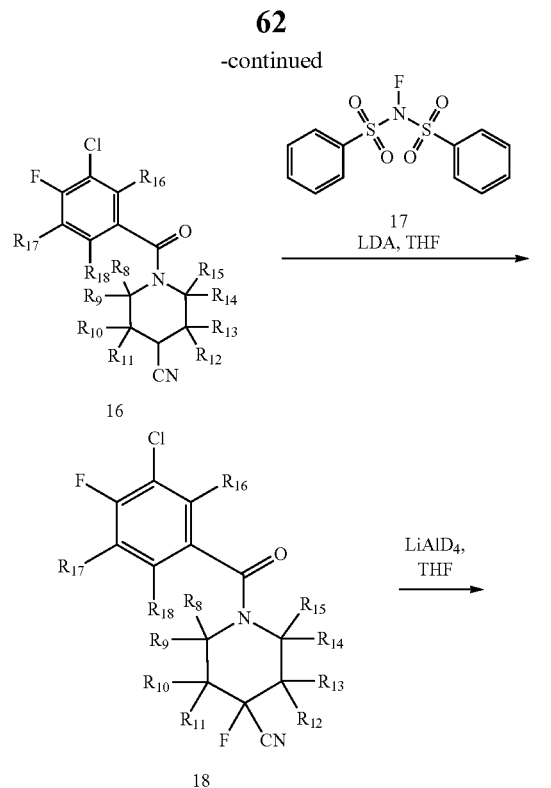

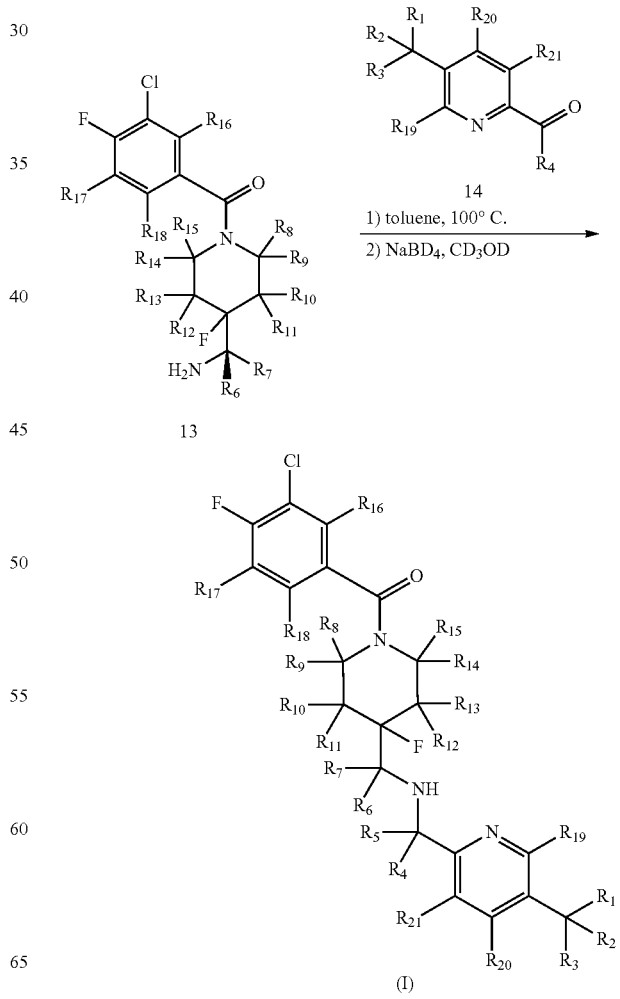

(I)

Deuterium can be incorporated into different positions synthetically, according to the synthetic procedures as shown in Scheme II, by using appropriate deuterated intermediates. For example, to introduce deuterium at one or more positions of $R_8$-$R_{15}$, compound 15 with the corresponding deuterium substitutions can be used. To introduce deuterium at one or more positions of $R_1$-$R_5$ and $R_{19}$-$R_{21}$, compound 14 with the corresponding deuterium substitutions can be used.

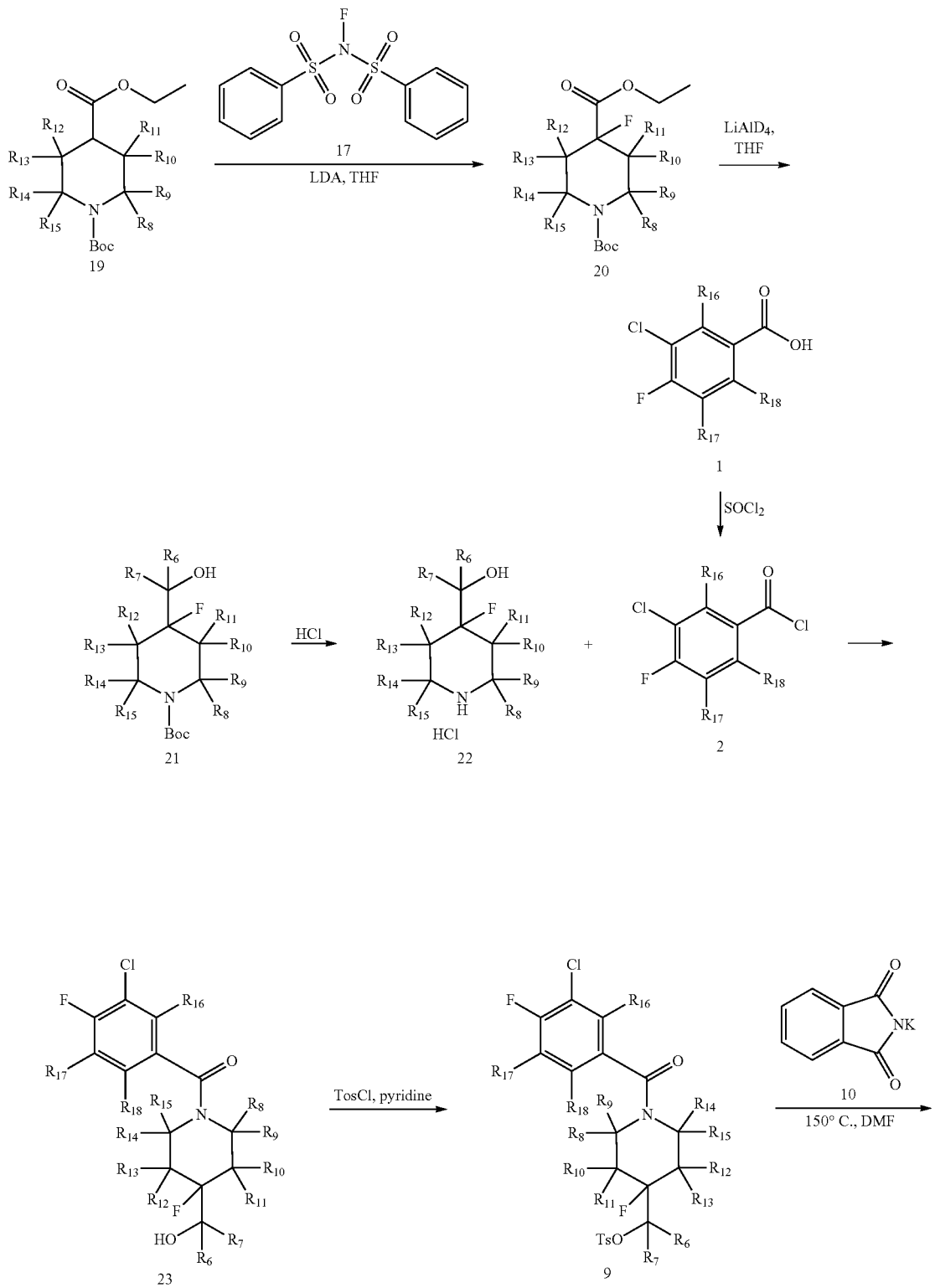

Scheme III

65

-continued

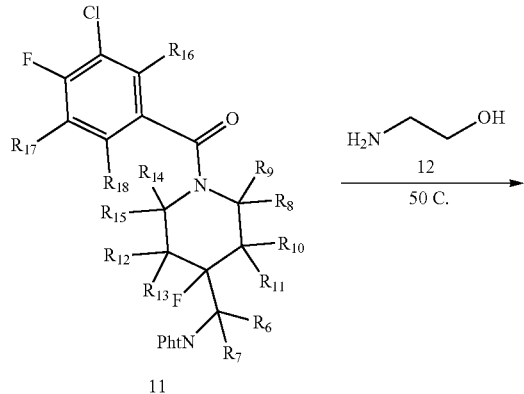

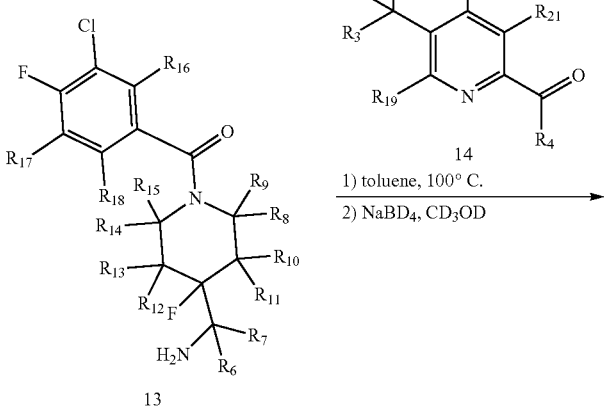

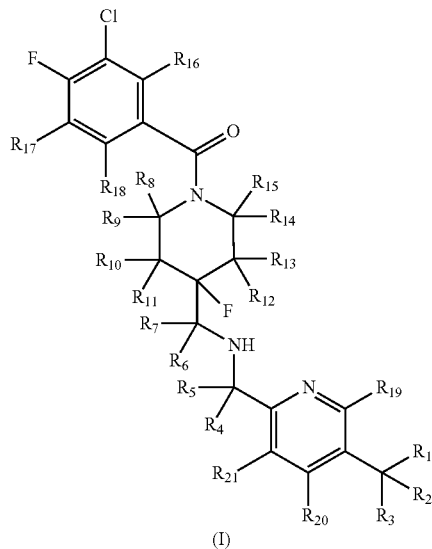

Deuterium can be incorporated into different positions synthetically, according to the synthetic procedures as shown in Scheme III, by using appropriate deuterated intermediates. For example, to introduce deuterium at one or more positions of $R_8$-$R_{15}$, compound 19 with the corresponding deuterium substitutions can be used. To introduce deuterium at $R_6$-$R_7$, compound 12 with the corresponding deuterium substitutions can be used. To introduce deuterium at one or more positions of $R_1$-$R_5$ and $R_{19}$-$R_{21}$, compound 14 with the corresponding deuterium substitutions can be used.

Scheme IV

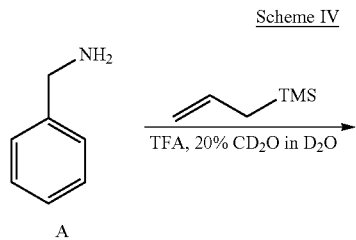

-continued

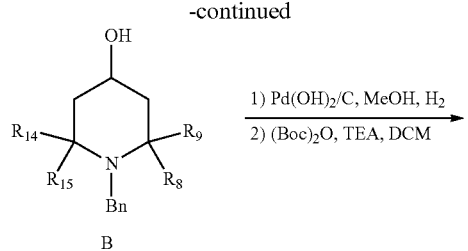

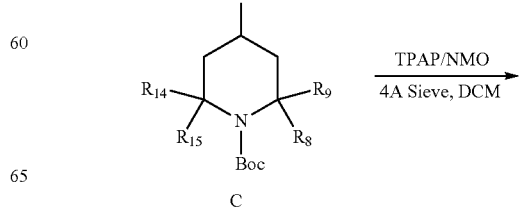

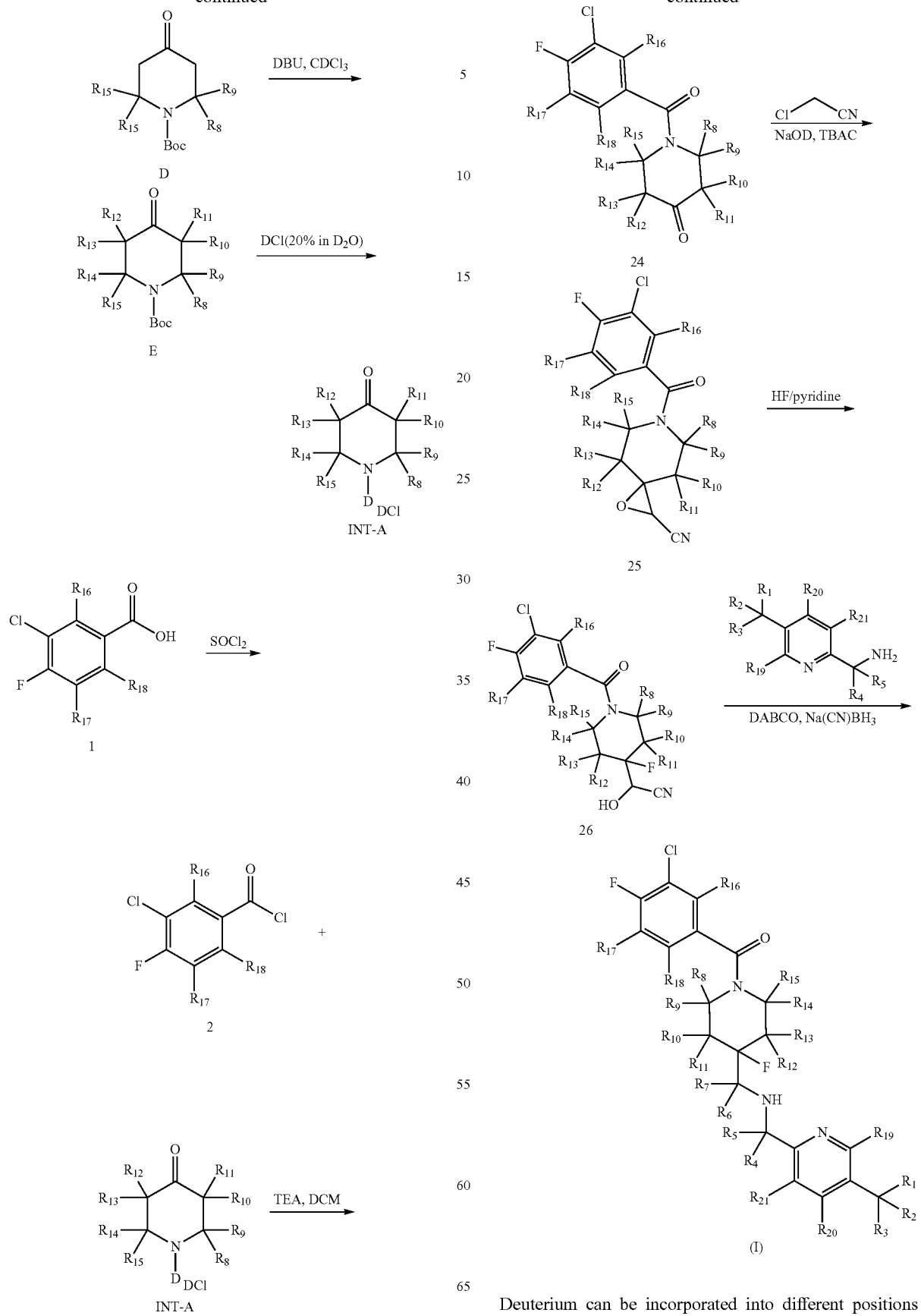
Deuterium can be incorporated into different positions synthetically, according to the synthetic procedures as shown in Scheme IV, by using appropriate deuterated intermediates. For example, to introduce deuterium at one or more positions of $R_8$-$R_{15}$, INT-A with the corresponding deuterium substitutions can be used. INT-A can be prepared from starting compound A. To introduce deuterium at $R_1$-$R_5$, $R_4$-$R_7$, and $R_{19}$-$R_{21}$, compound 27 with the corresponding deuterium substitutions and reagents DABCO can be used.

Compounds of Formula I, wherein X is N may be prepared as showing in the following reaction Scheme V and the description thereof, as well as relevant literature procedures that may be used by one skilled in the art. Exemplary reagents and procedures for these reactions appear hereinafter and in the working Examples. Any position shown as hydrogen may optionally be replaced with deuterium.

Scheme V

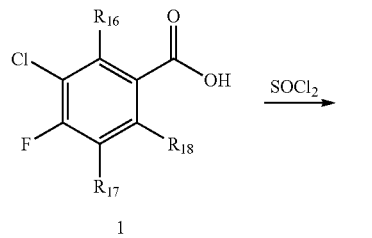

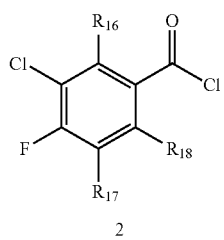

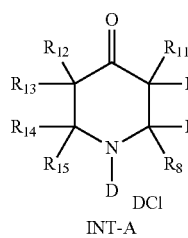

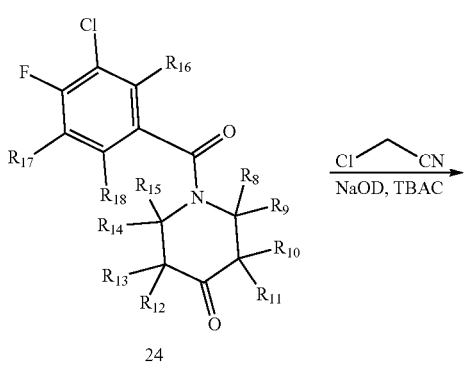

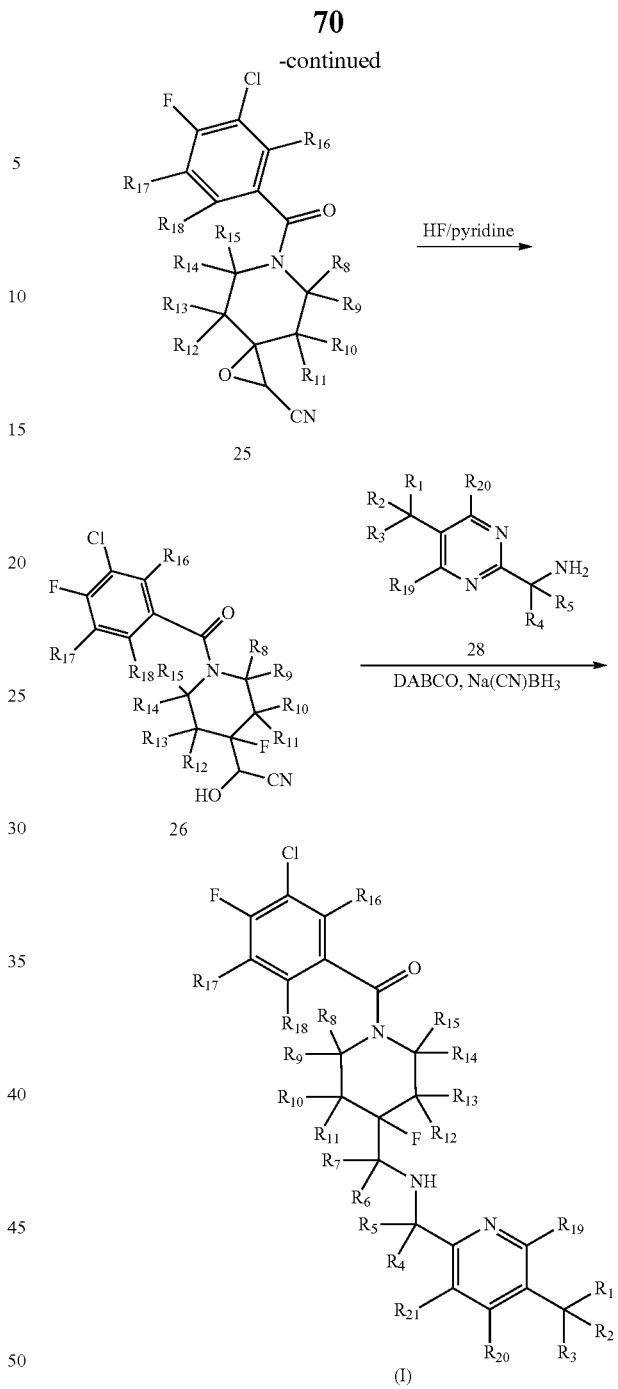

Deuterium can be incorporated into different positions synthetically, according to the synthetic procedures as shown in Scheme V, by using appropriate deuterated intermediates. For example, to introduce deuterium at one or more positions of $R_8$-$R_{15}$, INT-A with the corresponding deuterium substitutions can be used. To introduce deuterium at $R_1$-$R_5$, $R_4$-$R_7$, and $R_{19}$-$R_{21}$, compound 28 with the corresponding deuterium substitutions and reagents DABCO can be used.

Deuterium can be incorporated into various positions having an exchangeable proton, such as the amide and amine N—Hs, via proton-deuterium equilibrium exchange.

The invention is now described with reference to the following examples. Before describing several exemplary embodiments of the invention, it is to be understood that the invention is not limited to the details of construction or process steps set forth in the following description. The invention is capable of other embodiments and of being practiced or being carried out in various ways.

The following abbreviations may be employed in the Examples and elsewhere herein:

DMA=dimethylacetamide
DMF=dimethylformamide
DMSO=dimethyl sulfoxide
DCM=dichloromethane
THF=tetrahydrofuran
TEA=triethylamine
LDA=lithium diisopropylamide
IBX=2-iodoxy benzoic acid
TosCl=4-toluene sulfonyl chloride
TBAC=tert-butyl acetate
L=liter
mL=milliliter
µL=microliter
g=gram(s)
mg=milligram(s)
mol=moles
mmol=millimole(s)
h or hr=hour(s)
min=minute(s)
Equiv=equivalent(s)
H2=hydrogen
Ar=argon
N2=nitrogen
RT or R.T.=room temperature
AT=ambient temperature
Aq.=aqueous
HPLC=high performance liquid chromatography
HPLC R,=HPLC retention time
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point
All IUPAC names were generated using PerkinElmer®'s ChemDraw.

EXAMPLES

Example 1—Comparative (3-chloro-4-fluorophenyl)(4-fluoro-4-((((5-methyl-pyridin-2-yl)methyl)amino)methyl) piperidin-1-yl)methanone [Befiradol]

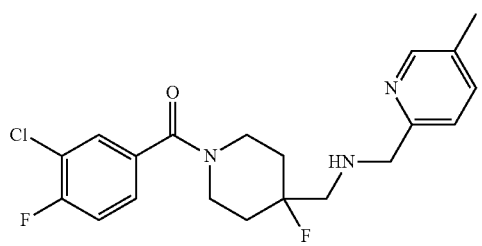 [SMILES: Cc1ccc(CNCC2(F)CCN(C(=O)c3ccc(F)c(Cl)c3)CC2)nc1]

Step 1: 3-chloro-4-fluorobenzoyl chloride

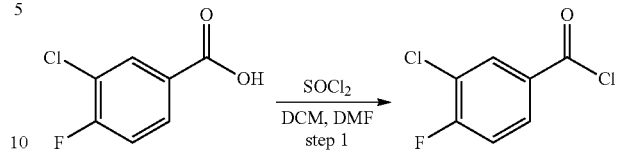

To a solution of 3-chloro-4-fluorobenzoic acid (15 g, 86.2 mmol, 1.00 equiv) in dichloromethane (150 mL) under an inert atmosphere of nitrogen was added N,N-dimethylformamide (315 mg, 4.3 mmol, 0.05 equiv). Then thionyl chloride (50.8 g, 431 mmol, 5 equiv) was added at 0° C. The reaction solution was stirred for 4 h at 45° C. The resulting mixture was concentrated under vacuum to afford 15 g (91%) of 3-chloro-4-fluorobenzoyl chloride as brown oil.

Step 2: 1-[(3-chloro-4-fluorophenyl)carbonyl]piperidin-4-one

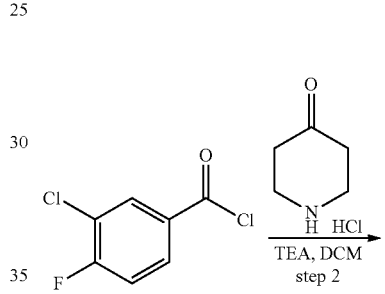

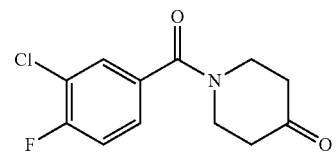

To a solution of piperidin-4-one hydrochloride (11.6 g, 86.3 mmol, 1.10 equiv) in dichloromethane (120 mL) under an inert atmosphere of nitrogen was added triethylamine (12.1 g, 120 mmol, 2.00 equiv)) at 0° C. This was followed by the addition of a solution of 3-chloro-4-fluorobenzoyl chloride [Example 1, Step 1] (15 g, 78.5 mmol, 1.00 equiv) in DCM (50 mL) dropwise with stirring at 0° C. in 15 min. The reaction solution was stirred for 1 h at room temperature. The reaction was quenched with water (200 mL). The resulting solution was extracted with dichloromethane (3×200 mL), and the organic layers were combined. The organic layers were washed with water (3×100 mL) and brine (3×100 mL). The mixture was dried over anhydrous sodium sulfate and concentrated under vacuum. The residue was applied onto a silica gel column with ethyl acetate/petroleum ether (1:2) to afford 17 g (85%) of 1-[(3-chloro-4-fluorophenyl)carbonyl]piperidin-4-one as a white solid. LC-MS: m/z=256[M+H]⁺.

Step 3: 6-[(3-chloro-4-fluorophenyl)carbonyl]-1-oxa-6-azaspiro[2.5]octane-2-carbonitril

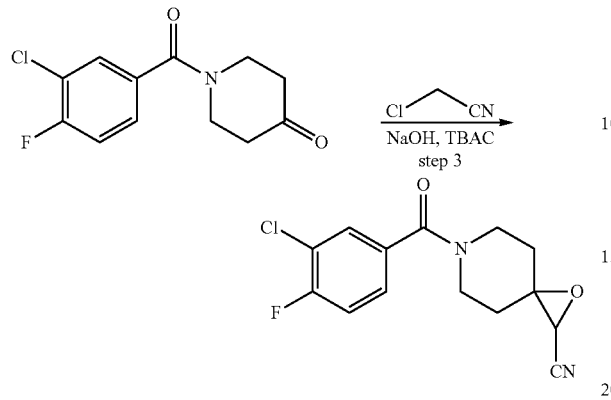

To a solution of 1-[(3-chloro-4-fluorophenyl) carbonyl]piperidin-4-one [Example 1, Step 2] (2 g, 7.8 mmol, 1.00 equiv) in dichloromethane (20 mL) was added sodium hydroxide (30.5% in H₂O) (5.4 mL, 7.00 equiv), TBAC (108 mg, 0.38 mmol, 0.05 equiv) and 2-chloroacetonitrile (1.18 g, 15.6 mmol, 2.00 equiv) at 0° C. The reaction solution was stirred for 1 h at room temperature. The resulting solution was diluted with water (100 mL). The resulting solution was extracted with dichloromethane (3×100 mL). The organic layers were washed with brine (3×50 mL). The mixture was dried over anhydrous sodium sulfate and concentrated under vacuum to afford 1.1 g (48%) of 6-[(3-chloro-4-fluorophenyl)carbonyl]-1-oxa-6-azaspiro[2.5]octane-2-carbonitril as a brown solid. LC-MS: m/z=295[M+H]⁺.

Step 4: 2-[1-[(3-chloro-4-fluorophenyl)carbonyl]-4-fluoropiperidin-4-yl]-2-hydroxyacetonitrile

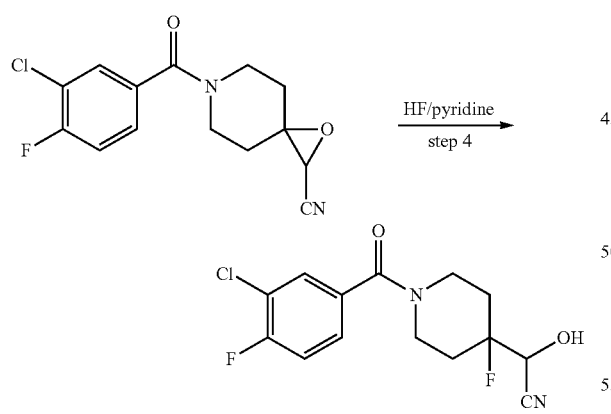

To a 10-mL teflon reactor was added 6-[(3-chloro-4-fluorophenyl)carbonyl]-1-oxa-6-azaspiro[2.5]octane-2-carbonitrile [Example 1, Step 3] (1.1 g, 3.7 mmol, 1.00 equiv) and HF/pyridine (2 mL). The resulting solution was stirred overnight at 25° C. The reaction was then quenched by the addition of water (10 mL). The pH value of the solution was adjusted to 8-9 with potassium carbonate. The resulting solution was extracted with DCM (3×30 mL). The organic layers were washed with water (3×20 mL) and brine (3×20 mL). The mixture was dried over anhydrous sodium sulfate and concentrated under vacuum to afford 1 g (85%) of 2-[1-[(3-chloro-4-fluorophenyl)carbonyl]-4-fluoropiperidin-4-yl]-2-hydroxyacetonitrile as yellow oil. LC-MS: m/z=315[M+H]⁺.

Step 5: tert-butyl N-[[5-methylpyridin-2-yl]methyl]carbamate

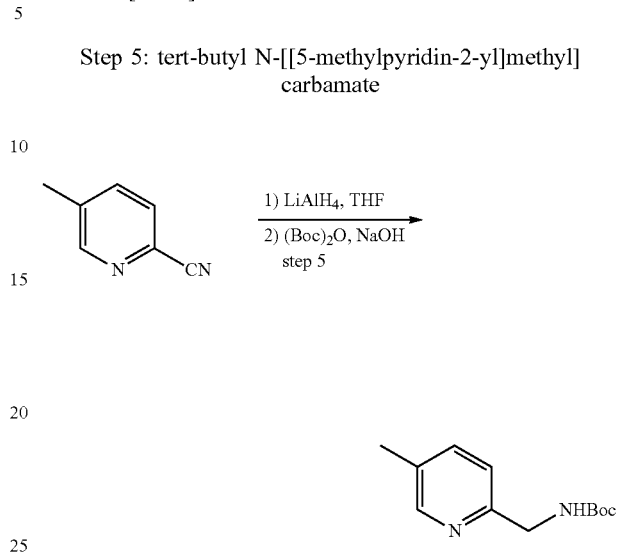

To a solution of 5-methylpyridine-2-carbonitrile (3 g, 24.56 mmol, 1.00 equiv) in tetrahydrofuran (30 mL) was added LiAlH₄ (1.4 g, 36.84 mmol, 1.50 equiv) at 0° C. The resulting solution was stirred for 30 min at 0° C. This was followed by the addition of H₂O (30 mL), NaOH (2.95 g, 73.7 mmol, 3.00 equiv) and (Boc)₂O (8 g, 37 mmol, 1.50 equiv). The resulting solution was stirred overnight at 25° C. The resulting solution was extracted with ethyl acetate (3×150 mL). The organic layers were washed with water (3×50 mL) and brine (3×50 mL). The mixture was dried over anhydrous sodium sulfate and concentrated under vacuum. The residue was applied onto a silica gel column with ethyl acetate/petroleum ether (1:9) to afford 2 g (37%) of tert-butyl N-[[5-methylpyridin-2-yl]methyl]carbamate as yellow oil. LC-MS: m/z=223 [M+H]⁺.

Step 6: [5-methylpyridin-2-yl]methanamine hydrochloride

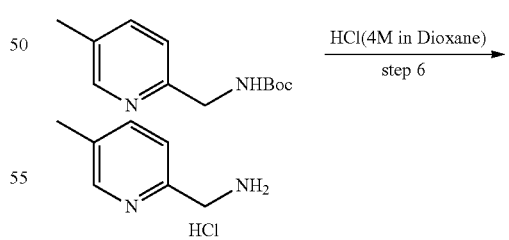

To a solution of tert-butyl N-[[5-methylpyridin-2-yl]methyl]carbamate [Example 1, Step 5] (2 g, 9 mmol, 1.00 equiv) in dichloromethane (20 mL) was added hydrogen chloride (4M in dioxane) (20 mL). The resulting solution was stirred overnight at 25° C. The resulting mixture was concentrated under vacuum to afford 1 g (crude) of [5-methylpyridin-2-yl]methanamine hydrochloride as a yellow solid.

Step 7: ([1-[(3-chloro-4-fluorophenyl)carbonyl]-4-fluoropiperidin-4-yl]methyl)[(5-methylpyridin-2-yl)methyl]amine

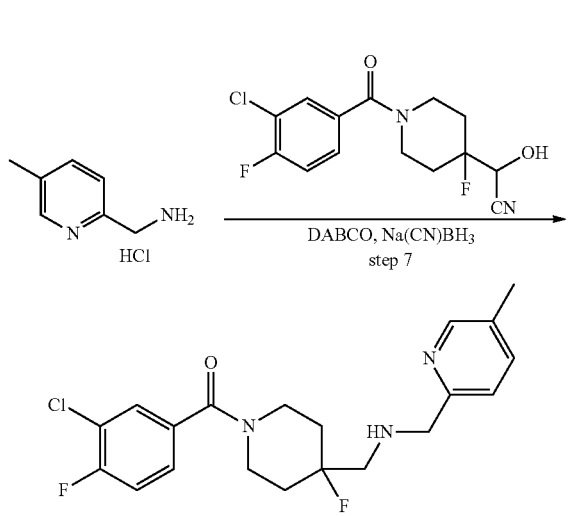

To a solution of 2-[1-[(3-chloro-4-fluorophenyl)carbonyl]-4-fluoropiperidin-4-yl]-2-hydroxyacetonitrile [Example 1, Step 4] (500 mg, 1.59 mmol, 1.00 equiv) in methanol (5 mL) was added (5-methylpyridin-2-yl)methanamine hydrochloride [Example 1, Step 6] (377.38 mg, 2.39 mmol, 1.50 equiv), DABCO (624.2 mg, 5.57 mmol, 3.50 equiv), and Na(CN)BH$_3$ (120 mg, 1.91 mmol, 1.20 equiv). The resulting solution was stirred overnight at 25° C. The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following conditions: Column, XBridge Prep OBD C18 Column, 19*250 mm; mobile phase, Water (0.05% NH$_4$HCO$_3$) and ACN (33.0% ACN up to 53.0% in 7 min); Detector, UV 254/220 nm to afford 120 mg (20%) of ([1-[(3-chloro-4-fluorophenyl)carbonyl]-4-fluoropiperidin-4-yl]methyl)[(5-methylpyridin-2-yl)methyl]amine as a white solid.

$^1$H NMR (400 MHz, DMSO-d$_6$) δ: 8.33-8.30 (m, 1H), 7.68-7.66 (m, 1H), 7.57-7.55 (m, 1H), 7.51-7.42 (m, 2H), 7.32-7.30 (m, 1H), 4.27-4.25 (m, 1H), 3.78 (s, 2H), 3.39-3.06 (m, 3H), 2.72-2.68 (m, 2H), 2.34 (s, 1H), 2.27 (s, 3H), 1.79-1.67 (m, 4H). LC-MS: m/z=394 [M+H]$^+$.

Example 2: (3-chloro-4-fluorophenyl)(4-fluoro-4-((((5-methylpyridin-2-yl)methyl)amino)methyl-d$_2$)piperidin-1-yl)methanone

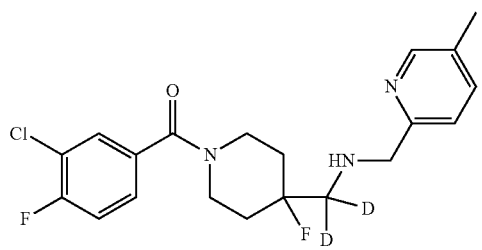 [SMILES: [2H]C([2H])(NCc1ccc(C)cn1)C1(F)CCN(C(=O)c2ccc(F)c(Cl)c2)CC1]

Step 1: methyl 5-methylpyridine-2-carboxylate

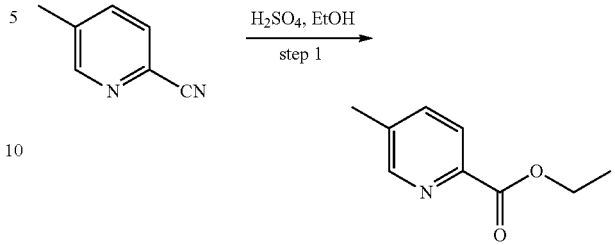

To a solution of 5-methylpyridine-2-carbonitrile (5 g, 42.3 mmol, 1.00 equiv) in ethanol (40 mL) was added sulfuric acid (10 mL, 4.00 equiv). The resulting solution was stirred for 2 days at 80° C. The reaction mixture was cooled to 25° C. The resulting mixture was concentrated under vacuum. The resulting solution was diluted with water (100 mL). The pH value of the solution was adjusted to 8-9 with potassium carbonate. The resulting solution was extracted with ethyl acetate (3×100 mL). The organic layers were washed with water (3×50 mL) and brine (3×50 mL). The mixture was dried over anhydrous sodium sulfate and concentrated under vacuum to afford 3 g (43%) of methyl 5-methylpyridine-2-carboxylate as light yellow oil. LC-MS: m/z=166[M+H]$^+$.

Step 2: (5-methylpyridin-2-yl)methanol

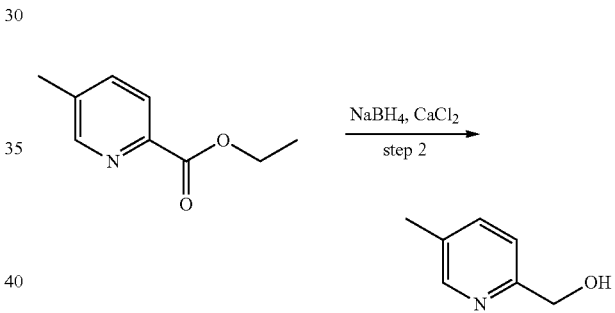

To a solution of methyl 5-methylpyridine-2-carboxylate [Example 2, Step 1] (3 g, 18.3 mmol, 1.00 equiv) in ethanol (20 mL) and tetrahydrofuran (20 mL) was added CaCl$_2$ (8.125 g, 549 mmol 4.00 equiv) and NaBH$_4$ (1.38 g, 36.6 mmol, 2.00 equiv). The resulting solution was stirred overnight at 50° C. The solids were filtered out. The filtrate was concentrated under vacuum. The resulting solution was diluted with ethyl acetate (50 mL). The solids were filtered out. The filtrate was concentrated under vacuum to afford 2.6 g (88.9%) of (5-methylpyridin-2-yl)methanol as light yellow oil. LC-MS: m/z=124[M+H]$^+$.

Step 3: 5-methylpyridine-2-carbaldehyde

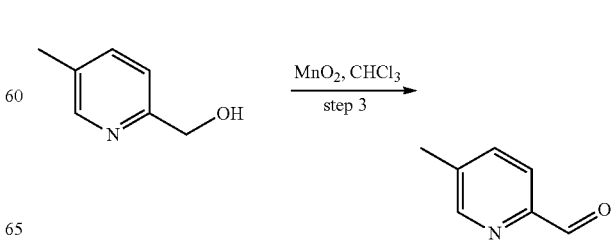

To a solution of (5-methylpyridin-2-yl)methanol [Example 2, Step 2] (2 g, 16.24 mmol, 1.00 equiv) in chloroform (25 mL) was added MnO$_2$ (18.39 g, 211.53 mmol, 13.00 equiv). The mixture was stirred overnight at 50° C. The solids were filtered out. The filtrate was concentrated under vacuum to afford 500 mg (25%) of 5-methylpyridine-2-carbaldehyde as brown oil. LC-MS: m/z=122[M+H]$^+$.

Step 4: ethyl 4-fluoropiperidine-4-carboxylate hydrochloride

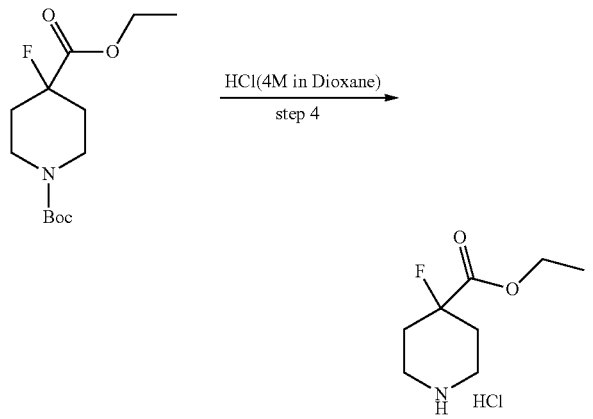

To a solution of 1-tert-butyl 4-ethyl 4-fluoropiperidine-1,4-dicarboxylate [Example 2, Step 3] (15 g, 54.48 mmol, 1.00 equiv) in dichloromethane (150 mL) was added hydrogen chloride (4M in dioxane) (100 mL). The resulting solution was stirred overnight at 25° C. The resulting mixture was concentrated under vacuum to afford 11 g (95%) of ethyl 4-fluoropiperidine-4-carboxylate hydrochloride as a white solid.

Step 5: ethyl 1-[(3-chloro-4-fluorophenyl)carbonyl]-4-fluoropiperidine-4-carboxylate

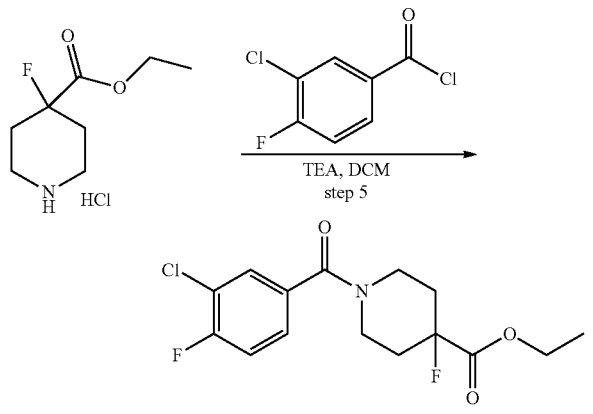

To a solution of 4-fluoropiperidine-4-carboxylate hydrochloride (11.8 g, 55.75 mmol, 1.10 equiv) in dichloromethane (150 mL) was added TEA (10.29 g, 101.69 mmol, 2.00 equiv). This was followed by the addition of a solution of 3-chloro-4-fluorobenzoyl chloride (9.76 g, 50.57 mmol, 1.00 equiv) in dichloromethane (10 mL) dropwise with stirring at 0° C. in 15 min. The resulting solution was stirred for 1.5 h at 0° C. The resulting solution was diluted with dichloromethane (200 mL). The organic layers were washed with water (3×100 mL) and brine (3×100 mL). The mixture was dried over anhydrous sodium sulfate and concentrated under vacuum to afford 18 g (crude) of ethyl 1-[(3-chloro-4-fluorophenyl)carbonyl]-4-fluoropiperidine-4-carboxylate as a white solid. LC-MS: m/z=332[M+H]$^+$.

Step 6: 1-[(3-chloro-4-fluorophenyl)carbonyl]-4-fluoropiperidine-4-carboxylic acid

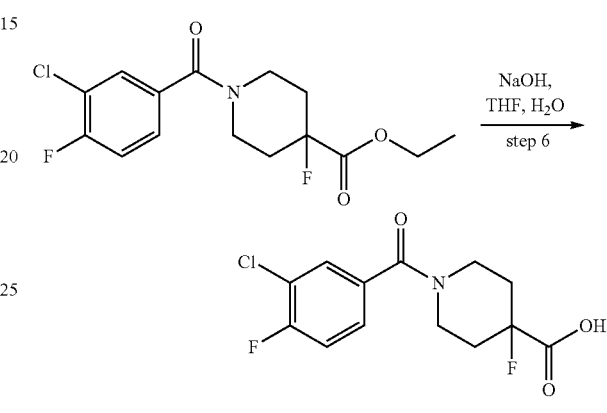

To a solution of ethyl 1-[(3-chloro-4-fluorophenyl)carbonyl]-4-fluoropiperidine-4-carboxylate [Example 2, Step 5] (18.7 g, 56.37 mmol, 1.00 equiv) in water (100 mL) and tetrahydrofuran (100 mL) was added sodium hydroxide (6.78 g, 169.50 mmol, 3.00 equiv). The resulting solution was stirred overnight at 25° C. The resulting mixture was concentrated under vacuum. The pH value of the solution was adjusted to 4-5 with hydrogen chloride (1M). The solids were collected by filtration. The solid was dried in an oven under reduced pressure to afford 14 g (82%) of 1-[(3-chloro-4-fluorophenyl)carbonyl]-4-fluoropiperidine-4-carboxylic acid as a white solid. LC-MS: m/z=304[M+H]$^+$.

Step 7: [1-[(3-chloro-4-fluorophenyl)carbonyl]-4-fluoropiperidin-4-yl](d$_2$)methanol

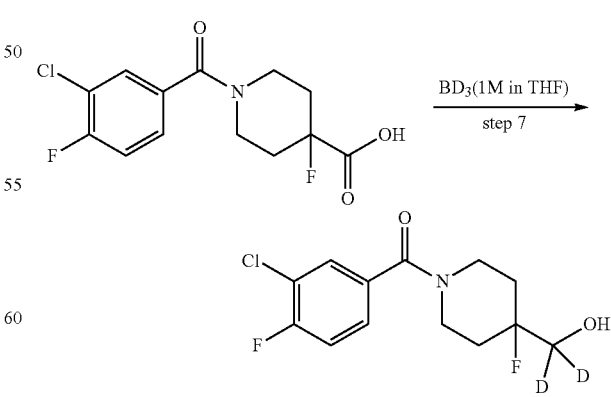

To a solution of tetrahydrofuran (100 mL) was added 1-[(3-chloro-4-fluorophenyl)carbonyl]-4-fluoropiperidine-4-carboxylic acid [Example 2, Step 6] (14.6 g, 48.08 mmol, 1.00 equiv). This was followed by the addition of BD$_3$ (1M in tetrahydrofuran) (96 mL, 2.00 equiv) dropwise with stirring at 0° C. in 15 min. The resulting solution was stirred overnight at 50° C. The reaction was then quenched by the addition of D$_2$O (50 mL). The resulting solution was extracted with ethyl acetate (3×100 mL). The organic layers were washed with water (3×50 mL) and brine (3×50 mL). The mixture was dried over anhydrous sodium sulfate and concentrated under vacuum. The residue was applied onto a silica gel column with ethyl acetate/petroleum ether (1:1) to afford 8 g (57%) of [1-[(3-chloro-4-fluorophenyl)carbonyl]-4-fluoropiperidin-4-yl](d$_2$)methanol as a white solid. LC-MS: m/z=292 [M+H]$^+$.

Step 8: [1-[(3-chloro-4-fluorophenyl)carbonyl]-4-fluoropiperidin-4-yl](d$_2$)methyl 4-methylbenzene-1-sulfonate

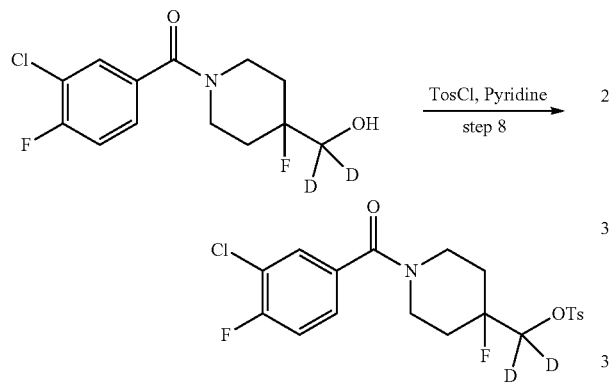

To a solution of [1-[(3-chloro-4-fluorophenyl)carbonyl]-4-fluoropiperidin-4-yl](d$_2$)methanol [Example 2, Step 7] (8 g, 27.41 mmol, 1.00 equiv) in Pyridine (100 mL) was added TosCl (5.76 g, 30.27 mmol, 1.10 equiv) at 0° C. The resulting solution was stirred overnight at 50° C. The reaction was then quenched by the addition of D$_2$O (50 mL). The resulting solution was extracted with dichloromethane (3×150 mL). The organic layers were washed with water (3×50 mL) and brine (3×50 mL). The mixture was dried over anhydrous sodium sulfate and concentrated under vacuum to afford 7 g (57%) of [1-[(3-chloro-4-fluorophenyl)carbonyl]-4-fluoropiperidin-4-yl](d$_2$)methyl 4-methylbenzene-1-sulfonate as yellow oil. LC-MS: m/z=446 [M+H]$^+$.

Step 9: 2-([1-[(3-chloro-4-fluorophenyl)carbonyl]-4-fluoropiperidin-4-yl](d$_2$)methyl)-2,3-dihydro-1H-isoindole-1,3-dione

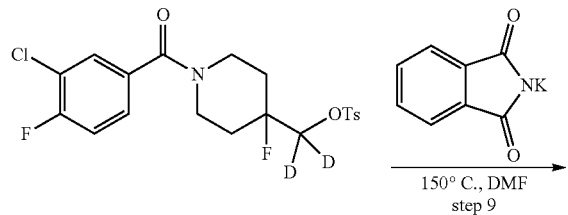

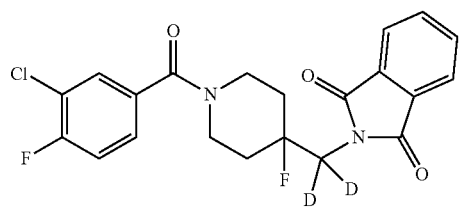

To a solution of [1-[(3-chloro-4-fluorophenyl)carbonyl]-4-fluoropiperidin-4-yl](d$_2$)methyl 4-methylbenzene-1-sulfonate [Example 2, Step 8] (7 g, 15.68 mmol, 1.00 equiv) in N,N-dimethylformamide (100 mL) was added 2-potassio-2,3-dihydro-1H-isoindole-1,3-dione (3.78 g, 20.44 mmol, 1.30 equiv). The resulting solution was stirred for 7 h at 150° C. The reaction mixture was cooled to 25° C. The reaction was then quenched by the addition of water. The resulting solution was extracted with dichloromethane (100 mL). The organic layers were washed with water (3×100 mL) and brine (3×100 mL). The mixture was dried over anhydrous sodium sulfate and concentrated under vacuum. The residue was applied onto a silica gel column with ethyl acetate/petroleum ether (1:1) to afford 6.1 g (92%) of 2-([1-[(3-chloro-4-fluorophenyl)carbonyl]-4-fluoropiperidin-4-yl](d$_2$)methyl)-2,3-dihydro-1H-isoindole-1,3-dione as a light yellow solid. LC-MS: m/z=421 [M+H]$^+$.

Step 10: [1-[(3-chloro-4-fluorophenyl)carbonyl]-4-fluoropiperidin-4-yl](d$_2$)methanamine

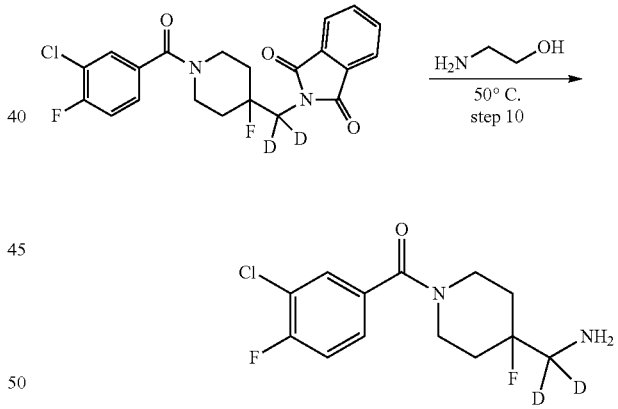

To a solution of 2-aminoethan-1-ol (100 mL) was added 2-([1-[(3-chloro-4-fluorophenyl)carbonyl]-4-fluoropiperidin-4-yl]($^2$H$_2$)methyl)-2,3-dihydro-1H-isoindole-1,3-dione [Example 2, Step 9] (6.1 g, 14.52 mmol, 1.00 equiv). The resulting solution was stirred for 2 h at 50° C. The reaction mixture was cooled to 25° C. The reaction was then quenched by the addition of water. The resulting solution was extracted with dichloromethane (100 mL). The organic layers were washed with water (3×100 mL) and brine (3×100 mL). The mixture was dried over anhydrous sodium sulfate and concentrated under vacuum to afford 4 g (95%) of [1-[(3-chloro-4-fluorophenyl)carbonyl]-4-fluoropiperidin-4-yl](d$_2$)methanamine as yellow oil. LC-MS: m/z=291 [M+H]$^+$.

Step 11: ([1-[(3-chloro-4-fluorophenyl)carbonyl]-4-fluoropiperidin-4-yl]($^2$H$_2$)methyl) [(5-methylpyridin-2-yl)methyl]amine

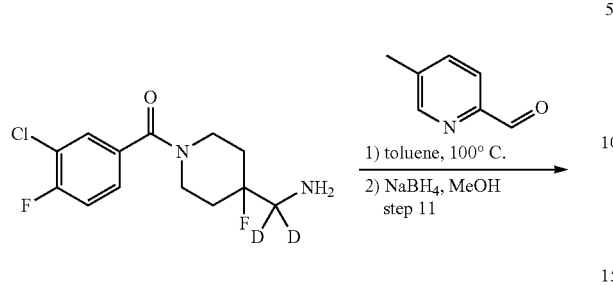

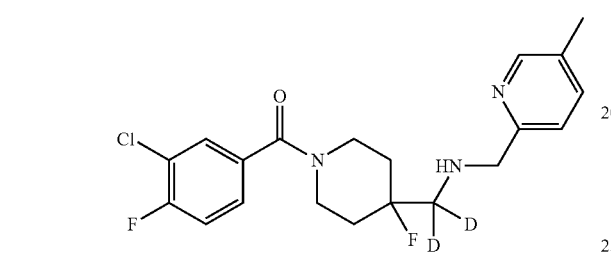

To a solution of [1-[(3-chloro-4-fluorophenyl)carbonyl]-4-fluoropiperidin-4-yl]($^2$H$_2$)methanamine [Example 2, Step 10] (1 g, 3.44 mmol, 1.00 equiv) in toluene (10 mL) was added 5-methylpyridine-2-carbaldehyde (417 mg, 3.44 mmol, 1.00 equiv). The resulting solution was stirred for 2 h at 100° C. The resulting mixture was concentrated under vacuum to remove toluene. The residue was taken up in methanol (10 mL) and cooled to 0° C., and NaBH$_4$ (261.44 mg, 6.88 mmol, 2.00 equiv) was added in several portions. The resulting solution was stirred overnight at 25° C. The resulting mixture was concentrated under vacuum to remove methanol. The resulting solution was diluted with ethyl acetate (25 mL). The organic layers were washed with water (3×10 mL) and brine (3×10 mL). The mixture was dried over anhydrous sodium sulfate and concentrated under vacuum. The crude product was purified by Prep-HPLC with the following conditions: Column,)(Bridge Prep OBD C18 Column 5 um, 30×150 mm; mobile phase, Water (10 mmol/L NH$_4$HCO$_3$) and ACN (32% ACN up to 48% in 7 min); Detector, UV 254/220 nm to afford 120 mg (9%) of ([1-[(3-chloro-4-fluorophenyl)carbonyl]-4-fluoropiperidin-4-yl](d$_2$)methyl)[(5-methylpyridin-2-yl)methyl]amine as a white solid.

$^1$H NMR (400 MHz, DMSO-d$_6$) δ: 8.33-8.32 (m, 1H), 7.68-7.66 (m, 1H), 7.57-7.55 (m, 1H), 7.51-7.42 (m, 2H), 7.32-7.30 (m, 1H), 4.27-4.25 (m, 1H), 3.78 (s, 2H), 3.39-3.06 (m, 3H), 2.34 (s, 1H), 2.27 (s, 3H), 1.79-1.62 (m, 4H). LC-MS: m/z=396 [M+H]$^+$.

Example 3: (3-chloro-4-fluorophenyl)(4-fluoro-4-((((5-(methyl-d$_3$)pyridin-2-yl)methyl)amino)methyl)piperidin-1-yl)methanone

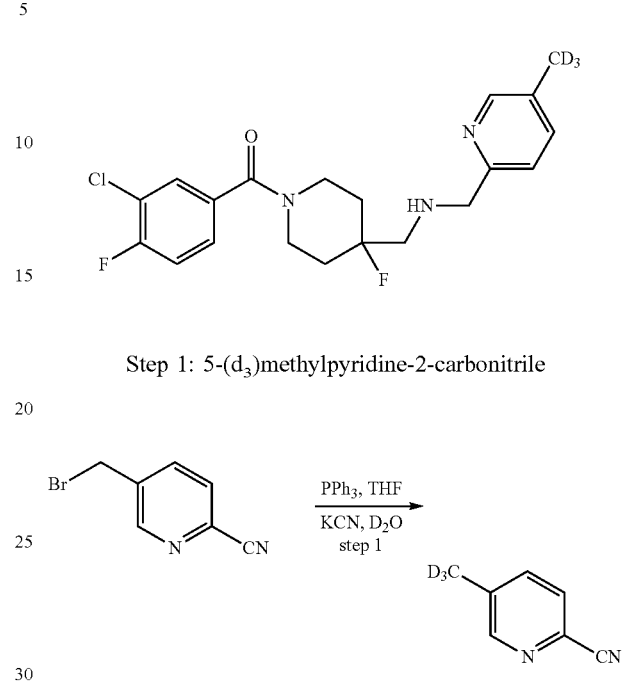

Step 1: 5-(d$_3$)methylpyridine-2-carbonitrile

To a solution of 5-(bromomethyl)pyridine-2-carbonitrile (6 g, 30.48 mmol, 1.00 equiv) in tetrahydrofuran (100 mL) was added PPh$_3$ (12 g, 45.72 mmol, 1.50 equiv). The resulting solution was stirred overnight at 40° C. This was followed by the addition of D$_2$O (100 mL) and KCN (2.4 g, 36.84 mmol, 1.20 equiv). The resulting solution was stirred overnight at 55° C. The resulting solution was diluted with ethyl acetate (300 mL). The organic layers were washed with water (3×70 mL) and brine (3×70 mL). The mixture was dried over anhydrous sodium sulfate and concentrated under vacuum. The residue was applied onto a silica gel column with ethyl acetate/petroleum ether (2:1) to afford 3 g (81%) of 5-(d$_3$)methylpyridine-2-carbonitrile as a yellow solid. LC-MS: m/z=122[M+H]$^+$.

Step 2: tert-butyl N-[[5-(d$_3$)methylpyridin-2-yl]methyl]carbamate

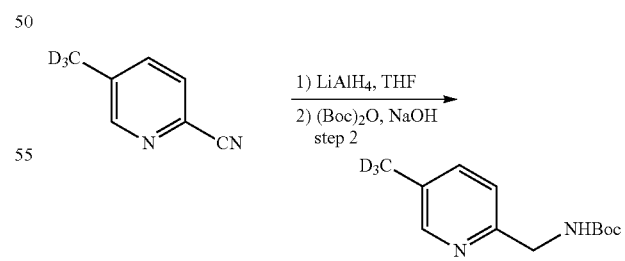

To a solution of 5-(d$_3$)methylpyridine-2-carbonitrile [Example 2, Step 1] (1 g, 8.25 mmol, 1.00 equiv) in tetrahydrofuran (10 mL) was added LiAlH$_4$ (472 mg, 12.44 mmol, 1.50 equiv) at 0° C. The resulting solution was stirred for 30 min at 0° C. This was followed by the addition of D$_2$O (10 mL), sodium hydroxide (331 mg, 8.28 mmol, 1.00 equiv) and (Boc)$_2$O (2.702 g, 12.38 mmol, 1.50 equiv). The resulting solution was stirred overnight at 25° C. The resulting solution was extracted with ethyl acetate (3×50 mL). The organic layers were washed with water (3×10 mL) and brine (3×10 mL). The mixture was dried over anhydrous sodium sulfate and concentrated under vacuum. The residue was applied onto a silica gel column with ethyl acetate/petroleum ether (1:9) to afford 1 g (54%) of tert-butyl N-[[5-($d_3$) methylpyridin-2-yl]methyl]carbamate as yellow oil.

$^1$H NMR (400 MHz, DMSO-$d_6$) δ: 8.39 (s, 1H), 7.65-7.64 (m, 1H), 7.30-7.28 (m, 1H), 4.32 (s, 2H), 1.48 (s, 3H).

Step 3: [5-($d_3$)methylpyridin-2-yl]methanamine hydrochloride

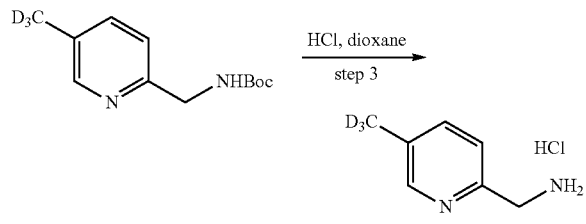

To a solution of tert-butyl N-[[5-($d_3$)methylpyridin-2-yl] methyl]carbamate [Example 2, Step 2] (1 g, 4.44 mmol, 1.00 equiv) in dichloromethane (10 mL) was added hydrogen chloride (4M in dioxane) (10 mL). The resulting solution was stirred overnight at 25° C. The resulting mixture was concentrated under vacuum to afford 800 mg (crude) of [5-($d_3$)methylpyridin-2-yl]methanamine hydrochloride as a yellow solid.

Step 4: ([1-[(3-chloro-4-fluorophenyl)carbonyl]-4-fluoropiperidin-4-yl]methyl][(5-($d_3$)methylpyridin-2-yl)methyl]amine

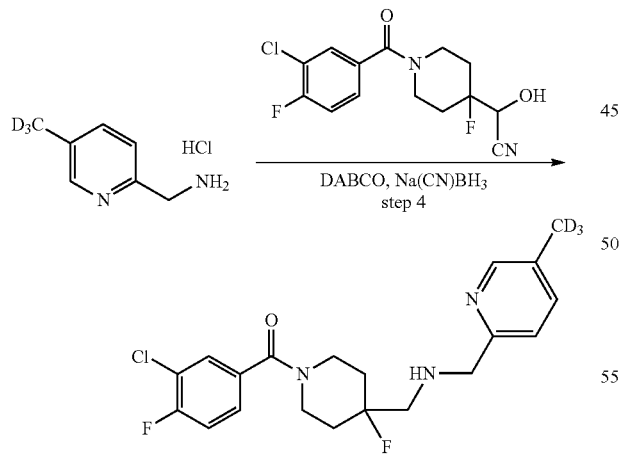

To a solution of 2-[1-[(3-chloro-4-fluorophenyl)carbonyl]-4-fluoropiperidin-4-yl]-2-hydroxyacetonitrile [Example 1, Step 4] (600 mg, 1.91 mmol, 1.00 equiv) in methanol (5 mL) was added [5-($d_3$)methylpyridin-2-yl] methanamine hydrochloride [Example 2, Step 3] (461.46 mg, 2.87 mmol, 1.50 equiv), DABCO (749 mg, 6.68 mmol, 3.50 equiv) and Na(CN)BH$_3$ (144 mg, 2.29 mmol, 1.20 equiv). The resulting solution was stirred overnight at 25° C.

The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following: Column, XBridge Prep OBD C18 Column Sum, 19×150 mm; mobile phase, Water (10 mmol/L NH$_4$HCO$_3$) and ACN (32% ACN up to 35% in 12 min); Detector, UV 254/220 nm to afford 150 mg (20%) of ([1-[(3-chloro-4-fluorophenyl)carbonyl]-4-fluoropiperidin-4-yl]methyl][(5-($d_3$)methylpyridin-2-yl)methyl]amine as a white solid.

$^1$H NMR (400 MHz, DMSO-$d_6$) δ: 8.33-8.32 (m, 1H), 7.68-7.66 (m, 1H), 7.57-7.55 (m, 1H), 7.51-7.42 (m, 2H), 7.32-7.30 (m, 1H), 4.27-4.25 (m, 1H), 3.78 (s, 2H), 3.39-3.06 (m, 3H), 2.72-2.67 (m, 2H), 2.34 (s, 1H), 1.79-1.62 (m, 4H). LC-MS: m/z=397 [M+H]$^+$.

Example 4: (3-chloro-4-fluorophenyl)(4-fluoro-4-((((5-(methyl-$d_3$)pyridin-2-yl)methyl-$d_2$)amino) methyl)piperidin-1-yl)methanone

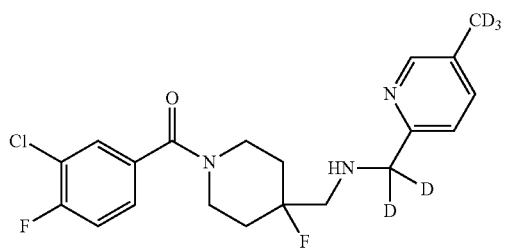 [SMILES: [2H]C([2H])([2H])c1ccc(C([2H])([2H])NCC2(F)CCN(C(=O)c3ccc(F)c(Cl)c3)CC2)nc1]

Step 1: tert-butyl N-[[5-($d_3$)methylpyridin-2-yl] ($^2$H$_2$)methyl]carbamate

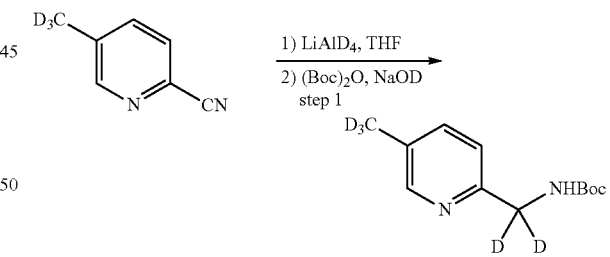

To a solution of 5-($d_3$)methylpyridine-2-carbonitrile [Example 3, Step 1] (1 g, 8.25 mmol, 1.00 equiv) in tetrahydrofuran (10 mL) was added LiAlD$_4$ (521 mg, 12.39 mmol, 1.50 equiv) at 0° C. The resulting solution was stirred for 30 min at 0° C. This was followed by the addition of D$_2$O (10 mL), NaOD (3M in D$_2$O) (2.75 mL, 8.25 mmol, 1.00 equiv), and (Boc)$_2$O (2.702 g, 12.38 mmol, 1.50 equiv). The resulting solution was stirred overnight at 25° C. The resulting solution was extracted with ethyl acetate (3×50 mL). The organic layers were washed with water (3×10 mL) and brine (3×10 mL). The mixture was dried over anhydrous sodium sulfate and concentrated under vacuum. The residue was applied onto a silica gel column with ethyl acetate/petroleum ether (1:9) to afford 1 g (54%) of tert-butyl N-[[5-($^2$H$_3$)methylpyridin-2-yl]($^2$H$_2$)methyl]carbamate as yellow oil. LC-MS: m/z=228 [M+H]$^+$.

Step 2: [5-(d$_3$)methylpyridin-2-yl](d$_2$)methanamine hydrochloride

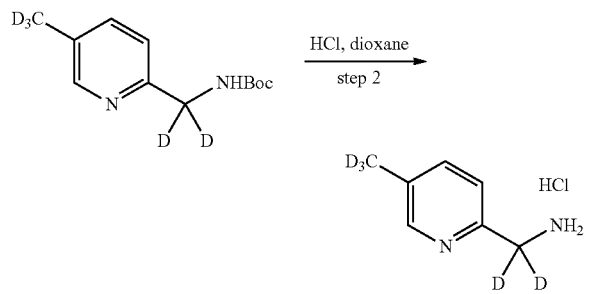

To a solution of tert-butyl N[[5-($^2$H$_3$)methylpyridin-2-yl]($^2$H$_2$)methyl]carbamate [Example 4, Step 1] (1 g, 4.44 mmol, 1.00 equiv) in dichloromethane (10 mL) was added hydrogen chloride (4M in dioxane) (10 mL). The resulting solution was stirred overnight at 25° C. The resulting mixture was concentrated under vacuum to afford 800 mg (crude) of [5-($^2$H$_3$)methylpyridin-2-yl]$^2$H$_2$)methanamine hydrochloride as a yellow solid.

Step 3: ([1-[(3-chloro-4-fluorophenyl)carbonyl]-4-fluoropiperidin-4-yl]methyl)[(5-(d$_3$)methylpyridin-2-yl)(d$_2$)methyl]amine

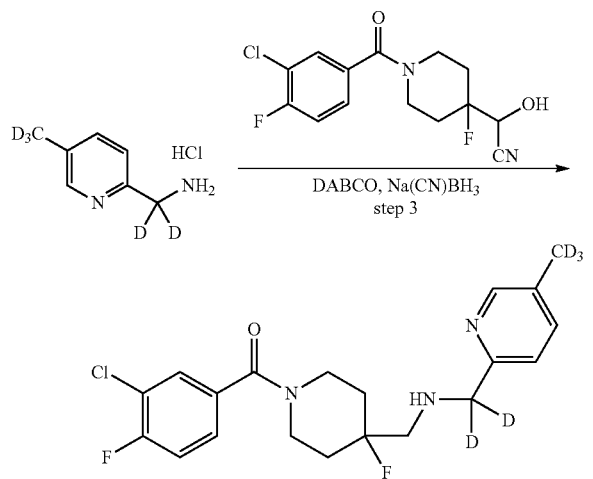

To a solution of 2-[1-[(3-chloro-4-fluorophenyl)carbonyl]-4-fluoropiperidin-4-yl]-2-hydroxyacetonitrile (600 mg, 1.91 mmol, 1.00 equiv) [Example 1, Step 4] in methanol (5 mL) was added [5-(d$_3$)methylpyridin-2-yl](d$_2$)methanamine hydrochloride [Example 4, Step 2] (467.0 mg, 2.87 mmol, 1.50 equiv), DABCO (749 mg, 6.68 mmol, 3.50 equiv), and Na(CN)BH$_3$ (144 mg, 2.29 mmol, 1.20 equiv). The resulting solution was stirred overnight at 25° C. The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following: Column,)(Bridge Prep OBD C18 Column Sum, 19×150 mm; mobile phase, Water (10 mmol/L NH$_4$HCO$_3$) and ACN (32% ACN up to 35% in 12 min); Detector, UV 254/220 nm to afford 160 mg (21%) of ([1-[(3-chloro-4-fluorophenyl)carbonyl]-4-fluoropiperidin-4-yl]methyl)[(5-($^2$H$_3$)methylpyridin-2-yl)($^2$H$_2$)methyl]amine as a white solid.

$^1$H NMR (400 MHz, DMSO-d$_6$) δ: 8.33-8.32 (m, 1H), 7.68-7.66 (m, 1H), 7.57-7.55 (m, 1H), 7.51-7.42 (m, 2H), 7.32-7.30 (m, 1H), 4.27-4.25 (m, 1H), 3.39-3.06 (m, 3H), 2.72-2.67 (m, 2H), 2.34 (s, 1H), 1.79-1.62 (m, 4H). LC-MS: m/z=399 [M+H]$^+$.

Example 5: (3-chloro-4-fluorophenyl)(4-fluoro-4-((((5-methylpyridin-2-yl)methyl-d$_2$)amino) methyl) piperidin-1-yl)methanone

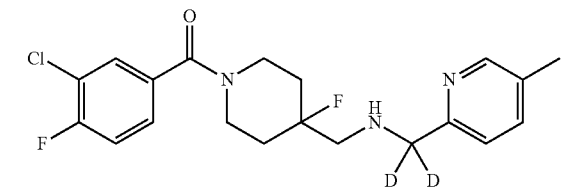 [SMILES: [2H]C([2H])(NCC1(F)CCN(C(=O)c2ccc(F)c(Cl)c2)CC1)c1ccc(C)cn1]

Step 1: tert-butyl N-[[5-methylpyridin-2-yl](d$_2$) methyl]carbamate

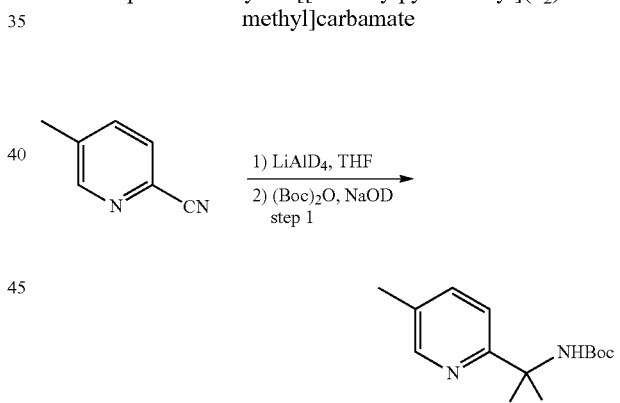

To a solution of 5-methylpyridine-2-carbonitrile (2.2 g, 18.6 mmol, 1.00 equiv) in tetrahydrofuran (30 mL) was added LiAlD$_4$ (1.17 g, 27.9 mmol, 1.50 equiv) at 0° C. The resulting solution was stirred for 30 min at 0° C. This was followed by the addition of D$_2$O (30 mL), NaOD (3M in D$_2$O) (18.6 mL, 55.8 mmol, 3.00 equiv), and (Boc)$_2$O (5.5 g, 25 mmol, 1.50 equiv). The resulting solution was stirred overnight at 25° C. The resulting solution was extracted with ethyl acetate (3×150 mL). The organic layers were washed with water (3×50 mL) and brine (3×50 mL). The mixture was dried over anhydrous sodium sulfate and concentrated under vacuum. The residue was applied onto a silica gel column with ethyl acetate/petroleum ether (1:14) to afford 2 g (53%) of tert-butyl N-[[5-methylpyridin-2-yl](d$_2$)methyl] carbamate as yellow oil. LC-MS: m/z=225 [M+H]$^+$.

Step 2: [5-methylpyridin-2-yl](d₂)methanamine hydrochloride

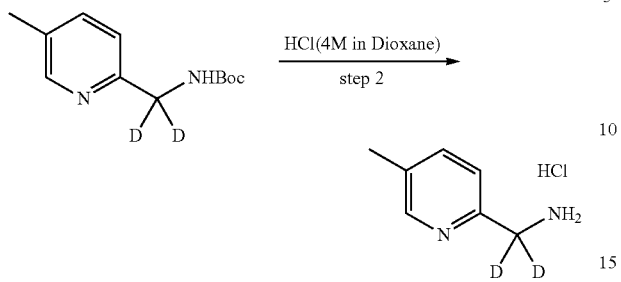

To a solution of tert-butyl N-[[5-methylpyridin-2-yl](d₂)methyl]carbamate [Example 4, Step 1] (2 g, 8.9 mmol, 1.00 equiv) in dichloromethane (20 mL) was added hydrogen chloride (4M in dioxane) (20 mL). The resulting solution was stirred overnight at 25° C. The resulting mixture was concentrated under vacuum to afford 1.35 g (crude) of [5-methylpyridin-2-yl](d₂)methanamine hydrochloride as a yellow solid.

Step 3: ([1-[(3-chloro-4-fluorophenyl)carbonyl]-4-fluoropiperidin-4-yl]methyl) [(5-methylpyridin-2-yl)(d₂)methyl]amine

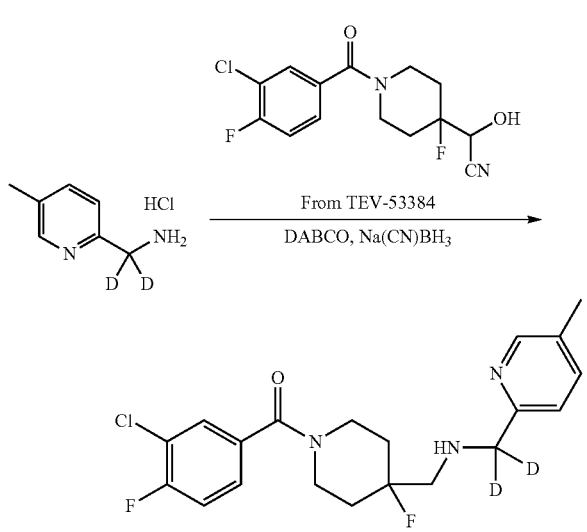

To a solution of 2-[1-[(3-chloro-4-fluorophenyl)carbonyl]-4-fluoropiperidin-4-yl]-2-hydroxyacetonitrile [Example 1, Step 4] (500 mg, 1.59 mmol, 1.00 equiv) in methanol (5 mL) was added (5-methylpyridin-2-yl)($^2$H₂)methanamine [Example 4, Step 2] (382.17 mg, 2.4 mmol, 1.50 equiv), DABCO (624.2 mg, 5.57 mmol, 3.50 equiv) and Na(CN)BH₃ (120 mg, 1.91 mmol, 1.20 equiv). The resulting solution was stirred overnight at 25° C. The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following conditions: Column,)(Bridge Prep OBD C18 Column, 19*250 mm; mobile phase, Water (0.05% NH₄HCO₃) and ACN (36.0% ACN up to 50.0% in 7 min); Detector, UV 254/220 nm to afford 140 mg (22%) of ([1-[(3-chloro-4-fluorophenyl)carbonyl]-4-fluoropiperidin-4-yl]methyl)[(5-methylpyridin-2-yl)(d₂) methyl]amine as a white solid.

$^1$H NMR (400 MHz, DMSO-d₆) δ: 8.33-8.30 (m, 1H), 7.68-7.66 (m, 1H), 7.57-7.55 (m, 1H), 7.51-7.42 (m, 2H), 7.32-7.30 (m, 1H), 4.26-4.25 (m, 1H), 3.39-3.06 (m, 3H), 2.72-2.68 (m, 2H), 2.34 (s, 1H), 2.27 (s, 3H), 1.79-1.64 (m, 4H). LC-MS: m/z=396 [M+H]⁺.

Example 6: (3-chloro-4-fluorophenyl)(4-fluoro-4-((((5-(methyl-d₃)pyridin-2-yl)methyl-d₂)amino)methyl-d₂)piperidin-1-yl)methanone

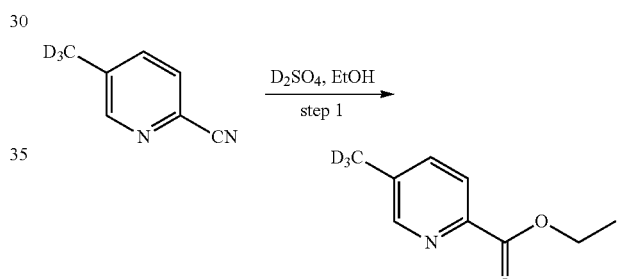

Step 1: methyl 5-(d₃)methylpyridine-2-carboxylate

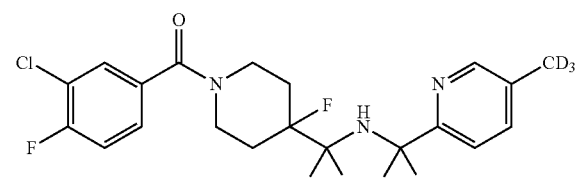

To a solution of 5-(d₃)methylpyridine-2-carbonitrile [Example 3, Step 1] (1.2 g, 9.92 mmol, 1.00 equiv) in ethanol (40 mL) was added D₂SO₄ (15 mL, 4.00 equiv). The resulting solution was stirred for 2 days at 80° C. The reaction mixture was cooled to 25° C. with a water bath. The resulting mixture was concentrated under vacuum. The resulting solution was diluted with water (100 mL). The pH value of the solution was adjusted to 8-9 with potassium carbonate. The resulting solution was extracted with ethyl acetate (3×100 mL). The organic layers were washed with water (3×50 mL) and brine (3×50 mL). The mixture was dried over anhydrous sodium sulfate and concentrated under vacuum to afford 1.2 g (72%) of methyl 5-($^2$H₃)methylpyridine-2-carboxylate as light yellow oil. LC-MS: m/z=169 [M+H]⁺.

Step 2: [5-(d₃)methylpyridin-2-yl](d₂)methanol

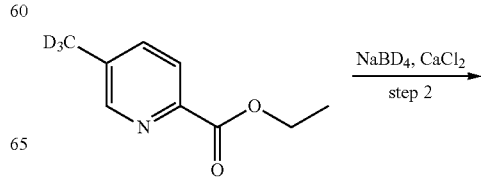

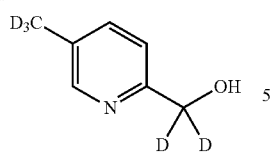

To a solution of methyl 5-(d₃)methylpyridine-2-carboxylate [Example 6, Step 1] (1.2 g, 7.14 mmol, 1.00 equiv) in ethanol (20 mL) and tetrahydrofuran (20 mL) was added CaCl₂ (3.16 g, 28.5 mmol 4.00 equiv) and NaBD₄ (600 mg, 14.3 mmol, 2.00 equiv). The resulting solution was stirred overnight at 50° C. The solids were filtered out. The filtrate was concentrated under vacuum. The resulting solution was diluted with ethyl acetate (50 mL). The solids were filtered out. The filtrate was concentrated under vacuum to afford 800 mg (87.5%) of [5-($^2$H₃)methylpyridin-2-yl]($^2$H₂)methanol as light yellow oil. LC-MS: m/z=129[M+H]⁺.

Step 3: [5-(d₃)methylpyridin-2-yl](d)formaldehyde

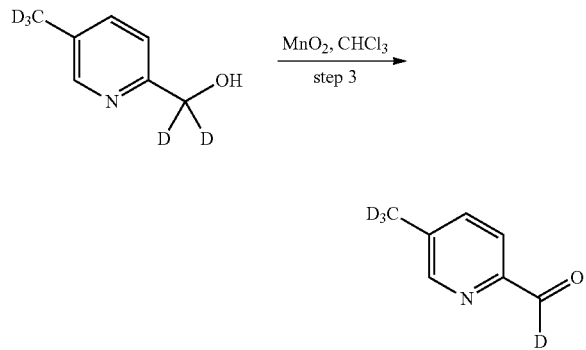

To a solution of [5-(d₃)methylpyridin-2-yl](d₂)methanol [Example 6, Step 2] (800 mg, 6.25 mmol, 1.00 equiv) in chloroform (10 mL) was added MnO₂ (7.07 g, 81.25 mmol, 13.00 equiv). The mixture was stirred overnight at 50° C. The solids were filtered out. The filtrate was concentrated under vacuum to afford 200 mg (25%) of [5-(d₃)methylpyridin-2-yl](d)formaldehyde as brown oil. LC-MS: m/z=126[M+H]⁺.

Step 4: ([1-[(3-chloro-4-fluorophenyl)carbonyl]-4-fluoropiperidin-4-yl](d₂)methyl)[(5-(d₃)methylpyridin-2-yl)(d₂)methyl]amine

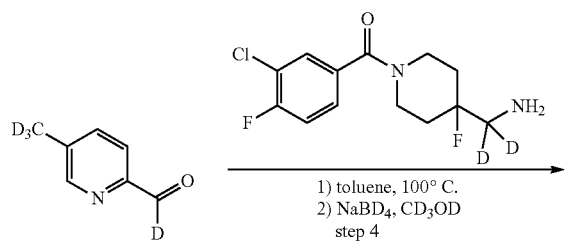

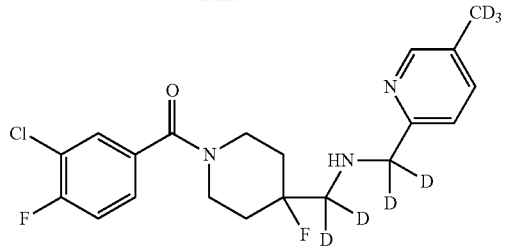

To a solution of [1-[(3-chloro-4-fluorophenyl)carbonyl]-4-fluoropiperidin-4-yl](d₂)methanamine [Example 2, Step 10] (464 mg, 1.6 mmol, 1.00 equiv) in toluene (10 mL) was added [5-(d₃)methylpyridin-2-yl](d)formaldehyde [Example 6, Step 3] (200 mg, 1.6 mmol, 1.00 equiv). The resulting solution was stirred for 2 h at 100° C. The resulting mixture was concentrated under vacuum to remove toluene. The residue was taken up in CD₃OD (10 mL) and cooled to 0° C., and NaBD₄ (134.4 mg, 3.2 mmol, 2.00 equiv) was added in several portions. The resulting solution was stirred overnight at 25° C. The resulting mixture was concentrated under vacuum to remove methanol. The resulting solution was diluted with ethyl acetate (25 mL). The organic layers were washed with water (3×10 mL) and brine (3×10 mL). The mixture was dried over anhydrous sodium sulfate and concentrated under vacuum. The crude product was purified by Prep-HPLC with the following conditions: Column,) (Bridge Prep OBD C18 Column 5 um, 30×150 mm; mobile phase, Water (10 mmol/L NH₄HCO₃) and ACN (32% ACN up to 48% in 7 min); Detector, UV 254/220 nm to afford 120 mg (18.7%) of ([1-[(3-chloro-4-fluorophenyl)carbonyl]-4-fluoropiperidin-4-yl](d₂)methyl)[(5-(d₃)methylpyridin-2-yl)(d₂)methyl]amine as a white solid.

$^1$H NMR (400 MHz, DMSO-d₆) δ: 8.33-8.32 (m, 1H), 7.68-7.66 (m, 1H), 7.57-7.55 (m, 1H), 7.51-7.42 (m, 2H), 7.32-7.30 (m, 1H), 4.27-4.25 (m, 1H), 3.39-3.06 (m, 3H), 2.34 (s, 1H), 1.79-1.62 (m, 4H). LC-MS: m/z=401 [M+H]⁺.

Example 7: ([1-[(3-chloro-4-fluorophenyl)carbonyl]-4-fluoro(d₈)piperidin-4-yl](d)methyl)[(5-methylpyridin-2-yl)methyl]amine

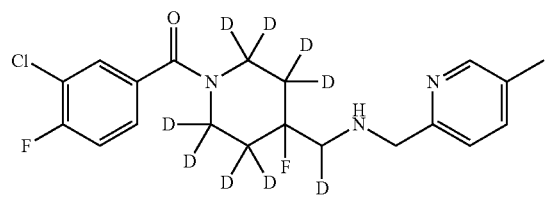 [SMILES: [2H]C(NCc1ccc(C)cn1)C1(F)C([2H])([2H])C([2H])([2H])N(C(=O)c2ccc(F)c(Cl)c2)C([2H])([2H])C1([2H])[2H]]

Step 1: 1-benzyl(2,2,6,6-d₄)piperidin-4-ol

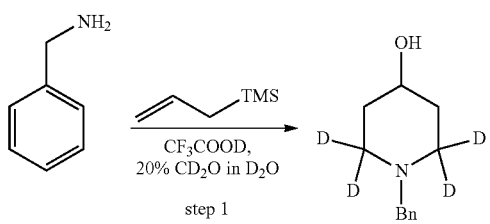

To a solution of CF$_3$COOD (10.75 g, 93.48 mmol, 1.00 equiv) was added phenylmethanamine (10 g, 93.32 mmol, 1.00 equiv) in several portions. The resulting solution was stirred for 30 min at 25° C. To this was added (d$_2$)-formaldehyde (20% in D$_2$O) (34.40 g, 1.07 mol, 2.30 equiv). The resulting mixture sonicated for 10 min and then stirred for 1 h at room temperature. To the resulting clear solution was added trimethyl(prop-2-en-1-yl)silane (11.72 g, 102.57 mmol, 1.10 equiv). The resulting solution was stirred overnight at 40° C. The reaction mixture was cooled to 25° C. The pH value of the solution was adjusted to 9 with potassium carbonate. The resulting solution was extracted with ethyl acetate (3×100 mL). The organic layers were dried over anhydrous sodium sulfate and concentrated under vacuum to afford 7 g (38%) of 1-benzyl(2,2,6,6-d$_4$)piperidin-4-ol as yellow oil. LC-MS: m/z=196[M+H]$^+$.

Step 2: (2,2,6,6-d$_4$)piperidin-4-ol

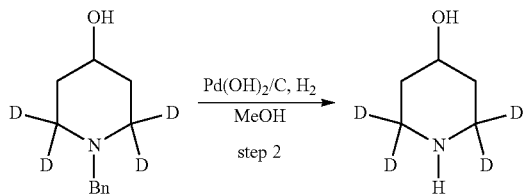 [SMILES: "MeOH" ; [2H]C1([2H])CC(O)CC([2H])([2H])N1Cc1ccccc1 ; [2H]C1([2H])CC(O)CC([2H])([2H])N1]

To a solution of 1-benzyl(2,2,6,6-d$_4$)piperidin-4-ol [Example 7, Step 1] (7 g, 35.84 mmol, 1.00 equiv) in methanol (100 mL) was added Pd(OH)$_2$/C (0.7 g). The flask was evacuated and flushed three times with nitrogen, followed by flushing with hydrogen. The mixture was stirred overnight at room temperature under an atmosphere of hydrogen (4 atm.). The solids were filtered out. The filtrate was concentrated under vacuum to afford 5 g (crude) of (2,2,6,6-d$_4$)piperidin-4-ol as yellow oil.

Step 3: tert-butyl 4-hydroxy(2,2,6,6-d$_4$)piperidine-1-carboxylate

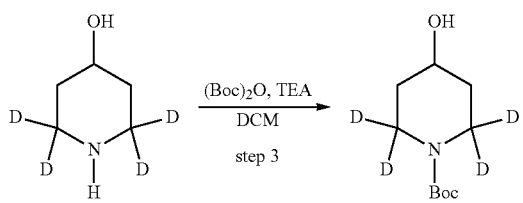

To a solution of (2,2,6,6-d$_4$)piperidin-4-ol [Example 7, Step 2] (5 g, 47.55 mmol, 1.00 equiv) in DCM (60 mL) was added TEA (11.06 g, 109.31 mmol, 2.30 equiv), and (Boc)$_2$O (12.45 g, 57.05 mmol, 1.20 equiv). The resulting solution was stirred overnight at 25° C. The resulting solution was diluted with D$_2$O. The resulting solution was extracted with DCM (3×100 mL). The organic layers were washed with water (3×50 mL) and brine (3×50 mL). The mixture was dried over anhydrous sodium sulfate and concentrated under vacuum. The residue was applied onto a silica gel column with ethyl acetate/petroleum ether (1:1) to afford 2.5 g (26%) of tert-butyl 4-hydroxy(2,2,6,6-d$_4$)piperidine-1-carboxylate as a white solid.

$^1$H NMR (400 MHz, CDCl$_3$) δ: 3.80-3.87 (m, 1H), 1.83-1.87 (m, 2H), 1.71 (s, 1H), 1.46-1.51 (m, 11H).

Step 4: tert-butyl 4-oxo(2,2,6,6-d$_4$)piperidine-1-carboxylate

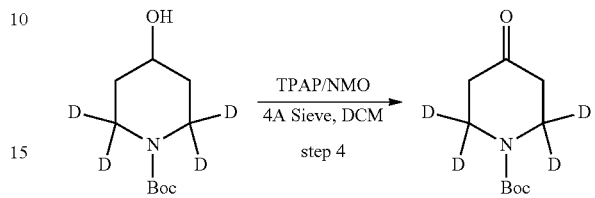

To a solution of tert-butyl 4-hydroxy(2,2,6,6-d$_4$)piperidine-1-carboxylate [Example 7, Step 3] (2.5 g, 12.18 mmol, 1.00 equiv) in dichloromethane (70 mL) was added 4A Sieve (3.75 g), NMO (2.15 g, 18.27 mmol, 1.50 equiv), and TPAP (214.32 mg, 0.61 mmol, 0.05 equiv) at 0° C. The resulting solution was stirred for 1.5 h at 25° C. The resulting mixture was concentrated under vacuum. The residue was applied onto a silica gel column with ethyl acetate/petroleum ether (1:9) to afford 2.3 g (93%) of tert-butyl 4-oxo(2,2,6,6-d$_4$) piperidine-1-carboxylate as a white solid.

Step 5: (2,2,6,6-d$_4$)piperidin-4-one hydrochloride

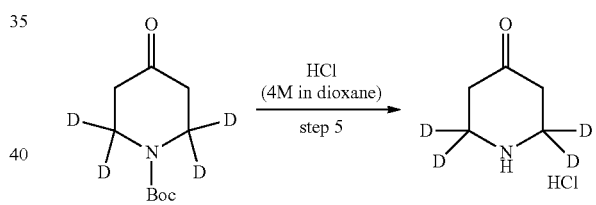

To a solution of tert-butyl 4-oxo(2,2,6,6-d$_4$)piperidine-1-carboxylate [Example 7, Step 4] (2.3 g, 11.31 mmol, 1.00 equiv) in DCM (25 mL) was added hydrogen chloride (4M in dioxane) (25 mL). The resulting solution was stirred overnight at 25° C. The resulting mixture was concentrated under vacuum to afford 2 g (crude) of (2,2,6,6-d$_4$)piperidin-4-one hydrochloride as light yellow solid.

Step 6: 1-[(3-chloro-4-fluorophenyl)carbonyl](2,2,6,6-d$_4$)piperidin-4-one

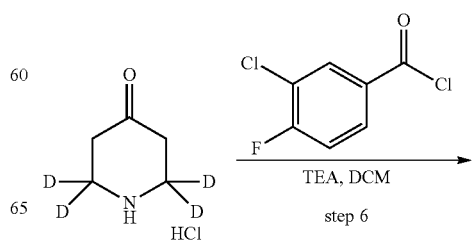

-continued

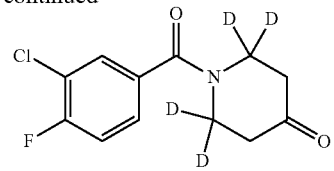

To a solution of (2,2,6,6-$d_4$)piperidin-4-one hydrochloride [Example 7, Step 5] (2 g, 14.32 mmol, 1.00 equiv) in DCM (30 mL) was added TEA (2.65 g, 26.14 mmol, 2.00 equiv). This was followed by the addition of a solution of 3-chloro-4-fluorobenzoyl chloride (3.02 g, 15.75 mmol, 1.10 equiv) in DCM (10 mL) dropwise with stirring at 0° C. in 15 min. The resulting solution was stirred for 1.5 h at 0° C. The resulting solution was diluted with DCM (150 mL). The organic layers were washed with water (3×25 mL) and brine (3×25 mL). The mixture was dried over anhydrous sodium sulfate and concentrated under vacuum. The residue was applied onto a silica gel column with ethyl acetate/petroleum ether (1:2) to afford 2 g (54%) of 1-[(3-chloro-4-fluorophenyl)carbonyl](2,2,6,6-$d_4$)piperidin-4-one as a white solid. LC-MS: m/z=260[M+H]$^+$.

Step 7: 1-[(3-chloro-4-fluorophenyl)carbonyl]($d_8$) piperidin-4-one

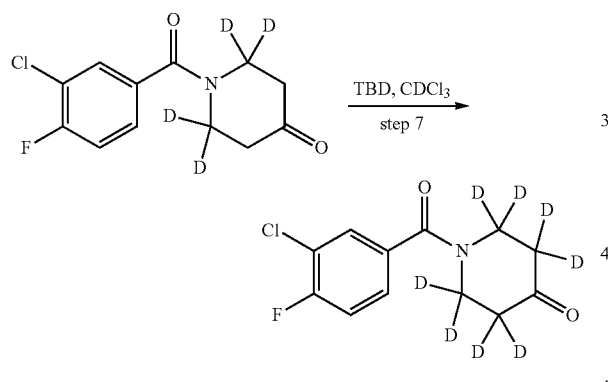

To a solution of 1-[(3-chloro-4-fluorophenyl)carbonyl](2,2,6,6-$d_4$) piperidin-4-one [Example 7, Step 6] (1.9 g, 7.32 mmol, 1.00 equiv) in CDCl$_3$ (15 mL) was added TBD (71.3 mg, 0.512 mmol, 0.07 equiv). The resulting solution was stirred overnight at 25° C. The resulting mixture was concentrated under vacuum to afford 1.9 g (98%) of 1-[(3-chloro-4-fluorophenyl)carbonyl]($^2$H8)piperidin-4-one as a light yellow solid. LC-MS: m/z=264[M+H]$^+$.

Step 8: 6-[(3-chloro-4-fluorophenyl)carbonyl]($d_9$)-1-oxa-6-azaspiro[2.5]octane-2-carbonitrile

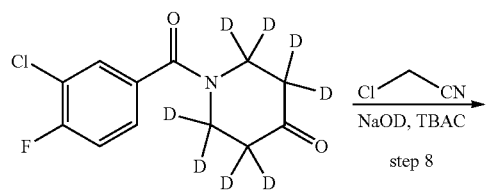

-continued

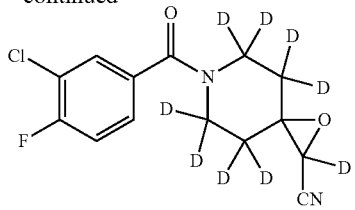

To a solution of 1-[(3-chloro-4-fluorophenyl)carbonyl]($d_8$)piperidin-4-one [Example 7, Step 7] (1.9 g, 7.20 mmol, 1.00 equiv) in DCM (25 mL) was added NaOD (3M in D$_2$O) (16.8 mL, 7.00 equiv), and TBAC (100 mg, 0.05 equiv). This was followed by the addition of 2-chloroacetonitrile (1.08 g, 14.31 mmol, 2.00 equiv) dropwise with stirring at 15° C. in 15 min. The resulting solution was stirred overnight at 25° C. The resulting solution was diluted with DCM (100 mL). The organic layers were washed with water (3×20 mL) and brine (3×20 mL). The mixture was dried over anhydrous sodium sulfate and concentrated under vacuum. The residue was applied onto a silica gel column with ethyl acetate/petroleum ether (1:2) to afford 800 mg (37%) of 6-[(3-chloro-4-fluorophenyl)carbonyl]($^2$H9)-1-oxa-6-azaspiro[2.5]octane-2-carbonitrile as yellow oil. LC-MS: m/z=304[M+H]$^+$.

Step 9: 2-[1-[(3-chloro-4-fluorophenyl)carbonyl]-4-fluoro($d_8$)piperidin-4-yl]-2-hydroxy(d)acetonitrile

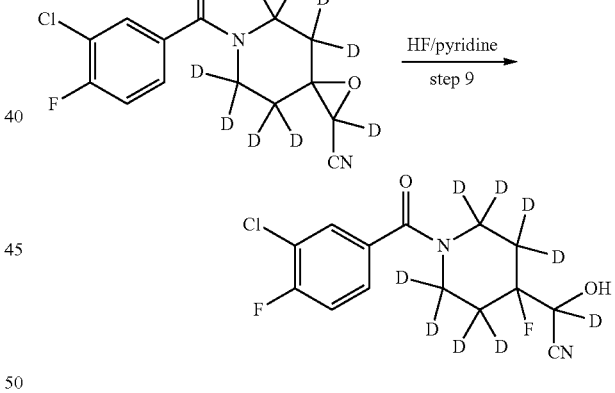

To a 10-mL teflon reactor was added 6-[(3-chloro-4-fluorophenyl)carbonyl]($d_9$)-1-oxa-6-azaspiro[2.5]octane-2-carbonitrile [Example 7, Step 8] (700 mg, 2.30 mmol, 1.00 equiv) and HF/pyridine (2 mL). The resulting solution was stirred overnight at 25° C. The reaction was then quenched by the addition of water (10 mL). The pH value of the solution was adjusted to 8-9 with potassium carbonate. The resulting solution was extracted with DCM (3×30 mL). The organic layers were washed with water (3×20 mL) and brine (3×20 mL). The mixture was dried over anhydrous sodium sulfate and concentrated under vacuum to afford 300 mg (crude) of 2-[1-[(3-chloro-4-fluorophenyl)carbonyl]-4-fluoro($d_8$)piperidin-4-yl]-2-hydroxy($^2$H)acetonitrile as yellow oil. LC-MS: m/z=324[M+H]$^+$.

Step 10: ([1-[(3-chloro-4-fluorophenyl)carbonyl]-4-fluoro($d_8$)piperidin-4-yl](d)methyl)[(5-methylpyridin-2-yl)methyl]amine

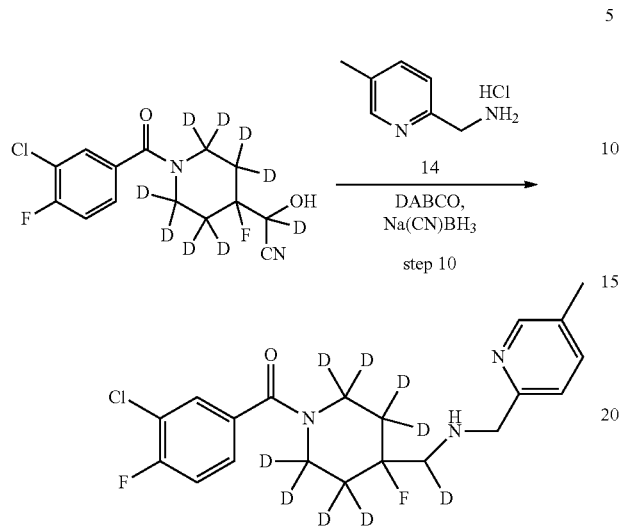

To a solution of 2-[1-[(3-chloro-4-fluorophenyl)carbonyl]-4-fluoro($d_8$)piperidin-4-yl]-2-hydroxy($^2$H)acetonitrile [Example 7, Step 9] (300 mg, 0.924 mmol, 1.00 equiv) in methanol (5 mL) was added (5-methylpyridin-2-yl)methanamine hydrochloride [Example 1, Step 6] (220.13 mg, 1.39 mmol, 1.50 equiv), DABCO (364.10 mg, 3.23 mmol, 3.50 equiv) and Na(CN)BH$_3$ (70.00 mg, 1.11 mmol, 1.20 equiv). The resulting solution was stirred overnight at 25° C. The resulting mixture was concentrated under vacuum to remove methanol. The resulting solution was diluted with EA (50 mL). The organic layers were washed with water (3×10 mL) and brine (3×10 mL). The mixture was dried over anhydrous sodium sulfate and concentrated under vacuum. The crude product was purified by Prep-HPLC with the following conditions: Column, Xselect CSH OBD Column 30*150 mm; mobile phase, Water (0.05% TFA) and ACN (20.0% ACN up to 30.0% in 7 min); Detector, UV 254/220 nm to afford 90 mg (24%) of ([1-[(3-chloro-4-fluorophenyl)carbonyl]-4-fluoro($d_8$)piperidin-4-yl](d)methyl)[(5-methylpyridin-2-yl)methyl]amine as a white solid.

$^1$H NMR (400 MHz, DMSO-$d_6$) δ: 8.33-8.30 (m, 1H), 7.68-7.66 (m, 1H), 7.57-7.55 (m, 1H), 7.51-7.42 (m, 2H), 7.32-7.30 (m, 1H), 3.78 (s, 2H), 2.72-2.64 (m, 1H), 2.34 (s, 1H), 2.27 (s, 3H). LC-MS: m/z=403 [M+H]$^+$.

Example 8—Comparative (3-chloro-4-fluorophenyl)(4-fluoro-4-((((5-methylpyrimidin-2-yl)methyl)amino) methyl)piperidin-1-yl)methanone

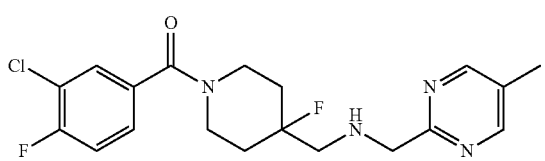 [SMILES: Cc1cnc(CNCC2(F)CCN(C(=O)c3ccc(F)c(Cl)c3)CC2)nc1]

Step 1: 5-methylpyrimidine-2-carbonitrile

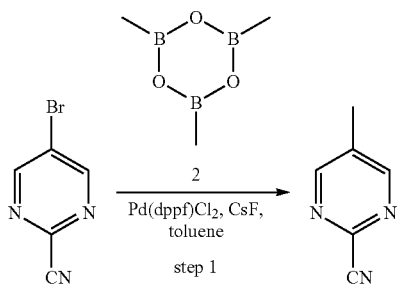

To a solution of 5-bromopyrimidine-2-carbonitrile (2 g, 10.87 mmol, 1.00 equiv) in toluene (15 mL) under an inert atmosphere of nitrogen was added trimethyl-1,3,5,2,4,6-trioxatriborinane (975.4 mg, 16.31 mmol, 1.5 equiv), CsF (1.66 g, 21.74 mmol, 2.0 equiv), K$_3$PO$_4$.3H$_2$O (4 g, 29.89 mmol, 2.75 equiv) and Pd(dppf)Cl$_2$.CH$_2$Cl$_2$ (799.7 mg, 2.17 mmol, 0.2 equiv). The reaction solution was stirred for 12 h at 100° C. The solid was filtered out. The filtrate was concentrated under vacuum. The residue was purified by a silica gel column with ethyl acetate/petroleum ether (1:1) to afford 0.5 g (38.6%) of 5-methylpyrimidine-2-carbonitrile as white solid. $^1$H NMR (300 MHz, DMSO-$d_6$) δ: 8.33 (s, 2H), 2.40 (s, 3H).

Step 2: (5-methylpyrimidin-2-yl)methanamine

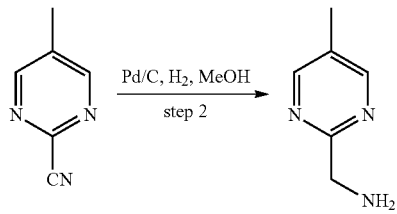

To a solution of 5-methylpyrimidine-2-carbonitrile [Example 8, Step 1] (900 mg, 7.56 mmol, 1.00 equiv) in methanol (15 mL) was added Pd/C (45 mg). The flask was evacuated and flushed three times with nitrogen, followed by flushing with hydrogen. The mixture was stirred for 1 h at room temperature under an atmosphere of hydrogen (3 atm). The solids were filtered out. The filtrate was concentrated under vacuum to afford 900 mg (crude) of (5-methylpyrimidin-2-yl)methanamine as brown oil. LC-MS: m/z=124 [M+H]$^+$.

Step 3: tert-butyl N-[(5-methylpyrimidin-2-yl)methyl]carbamate

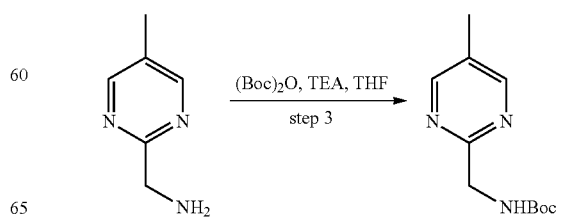

To a solution of (5-methylpyrimidin-2-yl)methanamine [Example 8, Step 2] (900 mg, 7.34 mmol, 1.00 equiv) in tetrahydrofuran (15 mL) was added TEA (3.7 g, 36.7 mmol, 5.00 equiv) and (Boc)₂O (1.92 g, 8.82 mmol, 1.50 equiv). The resulting solution was stirred overnight at 25° C. The resulting solution was diluted with H₂O (15 mL). The resulting solution was extracted with ethyl acetate (3×50 mL). The organic layers were washed with water (3×20 mL) and brine (3×20 mL). The mixture was dried over anhydrous sodium sulfate and concentrated under vacuum. The residue was purified by a silica gel column with ethyl acetate/ petroleum ether (1:1) to afford 600 mg (36.7%) of tert-butyl N-[(5-methylpyrimidin-2-yl)methyl]carbamate as yellow solid. LC-MS: m/z=224 [M+H]⁺.

Step 4: (5-methylpyrimidin-2-yl)methanamine hydrochloride

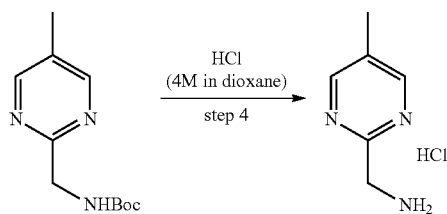

To a solution of tert-butyl N-[(5-methylpyrimidin-2-yl) methyl]carbamate [Example 8, Step 3] (600 mg, 2.69 mmol, 1.00 equiv) in dichloromethane (10 mL) was added hydrogen chloride (4M in dioxane) (10 mL). The resulting solution was stirred overnight at 25° C. The resulting mixture was concentrated under vacuum to afford 500 mg (crude) of (5-methylpyrimidin-2-yl)methanamine hydrochloride as a yellow solid. LC-MS: m/z=124 [M+H]⁺.

Step 5: ([1-[(3-chloro-4-fluorophenyl)carbonyl]-4-fluoropiperidin-4-yl]methyl)[(5-methylpyrimidin-2-yl)methyl]amine

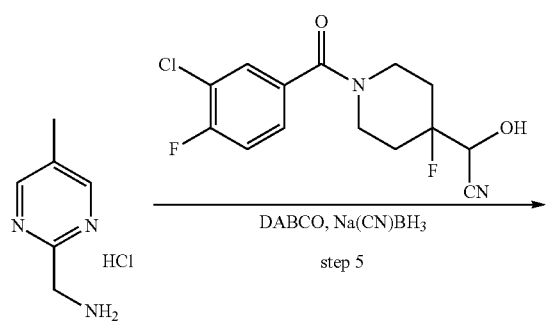

To a solution of 2-([1-[(3-chloro-4-fluorophenyl)carbonyl]-4-fluoropiperidin-4-yl]-2-hydroxyacetonitrile [Example 1, Step 4] (450 mg, 1.43 mmol, 1.00 equiv) in methanol (5 mL) was added (5-methylpyrimidin-2-yl)methanamine hydrochloride [Example 8, Step 4] (343.2 mg, 2.12 mmol, 1.50 equiv), DABCO (560.6 mg, 5.01 mmol, 3.50 equiv), and Na(CN)BH₃ (108.0 mg, 1.72 mmol, 1.20 equiv). The resulting solution was stirred overnight at 25° C. The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following conditions: Column, XBridge Prep OBD C18 Column, 19×250 mm; mobile phase, Water (0.05% NH₄HCO₃) and ACN (39.0% ACN in 8 min); Detector, UV 254/220 nm to afford 140 mg (24.9%) of ([1-[(3-chloro-4-fluorophenyl)carbonyl]-4-fluoropiperidin-4-yl]methyl)[(5-methylpyrimidin-2-yl)methyl]amine as a white solid.
¹H NMR (400 MHz, DMSO-d₆) δ: 8.618-8.617 (m, 2H), 7.687-7.664 (m, 1H), 7.516-7.425 (m, 2H), 4.241 (m, 1H), 3.890 (s, 2H), 3.400-3.067 (m, 3H), 2.789-2.738 (m, 2H), 2.340 (s, 1H), 2.257 (s, 3H), 1.799-1.646 (m, 4H). LC-MS: m/z=395 [M+H]⁺.

Example 9: (3-chloro-4-fluorophenyl)(4-fluoro-4-(((((5-methylpyrimidin-2-yl)methyl-d₂)amino) methyl)piperidin-1-yl)methanone

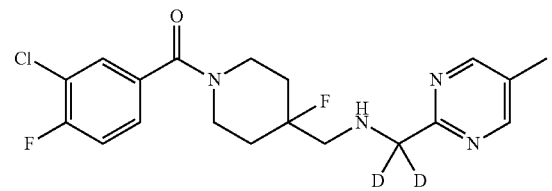 [SMILES: [2H]C([2H])(NCC1(F)CCN(C(=O)c2ccc(F)c(Cl)c2)CC1)c1ncc(C)cn1]

Step 1: 5-methylpyrimidine-2-carboxylic acid

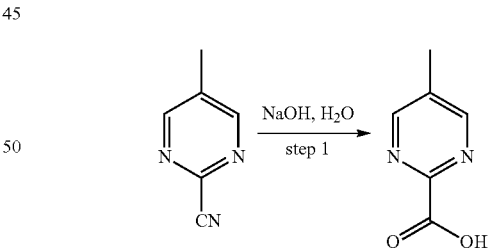

To a solution of 5-methylpyrimidine-2-carbonitrile [Example 8, Step 1] (2 g, 16.8 mmol, 1.00 equiv) in H₂O (30 mL) was added sodium hydroxide (1.01 g, 25.2 mmol, 1.50 equiv). The resulting solution was stirred for 3 h at 50° C. The pH value of the solution was adjusted to 4-5 with HCl (3M). The resulting mixture was concentrated under vacuum to remove H₂O. The resulting solution was diluted with methanol (50 mL). The solids were collected by filtration. The filtrate was dried over anhydrous sodium sulfate and concentrated under vacuum to afford 2 g (86.2%) of 5-methylpyrimidine-2-carboxylic acid as a white solid. LC-MS: m/z=139 [M+H]⁺.

Step 2: methyl 5-methylpyrimidine-2-carboxylate

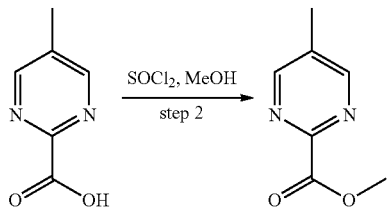

To a solution of methanol (50 mL) was added SOCl$_2$ (5.17 g, 43.5 mmol, 3.00 equiv) dropwise at 0° C. The resulting solution was stirred for 0.5 h at 25° C. This was followed by the addition of 5-methylpyrimidine-2-carboxylic acid [Example 9, Step 1] (2 g, 14.5 mmol, 1.00 equiv). The resulting solution was stirred for 1 h at 65° C. The resulting mixture was concentrated under vacuum to remove methanol and SOCl$_2$. The resulting solution was diluted with H$_2$O (30 mL). The resulting solution was extracted with ethyl acetate (3×30 mL). The organic layers were dried over anhydrous sodium sulfate and concentrated under vacuum to afford 2 g (90.7%) of methyl 5-methylpyrimidine-2-carboxylate as a yellow solid. LC-MS: m/z=153 [M+H]$^+$.

Step 3: (5-methylpyrimidin-2-yl)(d$_2$)methanol

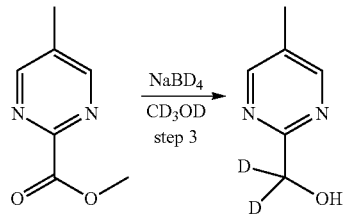

To a solution of methyl 5-methylpyrimidine-2-carboxylate [Example 9, Step 2] (2 g, 13.2 mmol, 1.00 equiv) in MeOD (30 mL) was added NaBD$_4$ (1.66 g, 39.2 mmol, 3.00 equiv) at 0° C. The resulting solution was stirred for 3 h at 25° C. The reaction was then quenched by the addition of D$_2$O (10 mL). The resulting mixture was concentrated under vacuum to remove MeOD. The resulting solution was extracted with ethyl acetate (3×20 mL). The organic layers were dried over anhydrous sodium sulfate and concentrated under vacuum to afford 1.5 g (90.2%) of (5-methylpyrimidin-2-yl)(d$_2$)methanol as a yellow solid. LC-MS: m/z=127 [M+H]$^+$.

Step 4: 2-[bromo(d$_2$)methyl]-5-methylpyrimidine

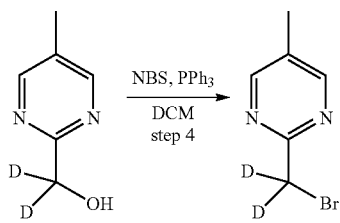

To a solution of (5-methylpyrimidin-2-yl)(d$_2$)methanol [Example 9, Step 3] (1.5 g, 11.9 mmol, 1.00 equiv) in DCM (20 mL) was added PPh$_3$ (3.12 g, 11.9 mmol, 1.00 equiv) and NBS (2.12 g, 11.9 mmol, 1.00 equiv) at 0° C. The resulting solution was stirred for 1 h at 0° C. The reaction was then quenched by the addition of H$_2$O (20 mL). The resulting solution was extracted with DCM (3×20 mL). The organic layers were dried over anhydrous sodium sulfate and concentrated under vacuum. The residue was applied onto a silica gel column with ethyl acetate/petroleum ether (1:2) to afford 700 mg (31.3%) of 2-[bromo(d$_2$)methyl]-5-methylpyrimidine as a yellow oil. LC-MS: m/z=189[M+H]$^+$.

Step 5: 2-(azido(d$_2$)methyl)-5-methylpyrimidine

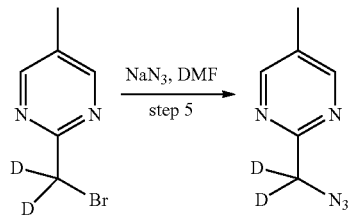

To a solution of 2-[bromo(d$_2$)methyl]-5-methylpyrimidine [Example 9, Step 4] (700 mg, 3.72 mmol, 1.00 equiv) in DMF (10 mL) was added NaN$_3$ (605.1 mg, 9.31 mmol, 2.50 equiv). The resulting solution was stirred for 1 h at 60° C. The reaction was then quenched by the addition of H$_2$O (20 mL). The resulting solution was extracted with ethyl acetate (3×20 mL). The organic layers were dried over anhydrous sodium sulfate and concentrated under vacuum to afford 600 mg (crude) of 2-(azido(d$_2$)methyl)-5-methylpyrimidine as a yellow oil. LC-MS: m/z=152[M+H]$^+$.

Step 6: tert-butyl N-[(5-methylpyrimidin-2-yl)($^2$H$_2$)methyl]carbamate

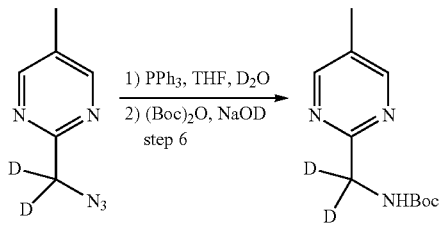 [SMILES: [2H]C([2H])(N=[N+]=[N-])c1ncc(C)cn1 ; [2H]C([2H])(NC(=O)OC(C)(C)C)c1ncc(C)cn1]

To a solution of 2-(azido(d$_2$)methyl)-5-methylpyrimidine [Example 9, Step 5] (600 mg, 3.97 mmol, 1.00 equiv) in tetrahydrofuran (10 mL) and D$_2$O (2.5 mL) was added PPh$_3$ (1.35 g, 5.17 mmol, 1.30 equiv). The resulting solution was stirred for 2.5 h at 70° C. The reaction was then quenched by the addition of D$_2$O (5 mL). This was followed by the addition of D$_2$O (2.5 mL), NaOD (3M in D$_2$O) (1.99 mL, 5.96 mmol, 1.50 equiv) and (Boc)$_2$O (1.30 g, 5.96 mmol, 1.50 equiv). The resulting solution was stirred overnight at 25° C. The resulting solution was extracted with ethyl acetate (3×30 mL). The organic layers were washed with water (3×15 mL) and brine (3×15 mL). The mixture was dried over anhydrous sodium sulfate and concentrated under vacuum. The residue was applied onto a silica gel column with ethyl acetate/petroleum ether (1:20) to afford 500 mg (56%) of tert-butyl N-[(5-methylpyrimidin-2-yl)(d₂)methyl]carbamate as yellow oil. LC-MS: m/z=226 [M+H]⁺.

Step 7: (5-methylpyrimidin-2-yl)(²H₂)methanamine hydrochloride

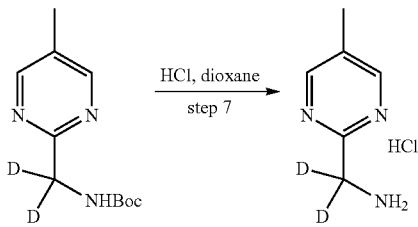 [SMILES: [2H]C([2H])(NC(=O)OC(C)(C)C)c1ncc(C)cn1 ; [2H]C([2H])(N)c1ncc(C)cn1 ; Cl]

To a solution of tert-butyl N-[(5-methylpyrimidin-2-yl)(d₂)methyl]carbamate [Example 9, Step 6] (500 mg, 2.22 mmol, 1.00 equiv) in dichloromethane (5 mL) was added hydrogen chloride (4M in dioxane) (5 mL). The resulting solution was stirred overnight at 25° C. The resulting mixture was concentrated under vacuum to afford 500 mg (crude) of (5-methylpyrimidin-2-yl)(d₂)methanamine hydrochloride as a yellow solid. LC-MS: m/z=126 [M+H]⁺.

Step 8: ([1-[(3-chloro-4-fluorophenyl)carbonyl]-4-fluoropiperidin-4-yl]methyl)[(5-methylpyrimidin-2-yl)(d₂)methyl]amine

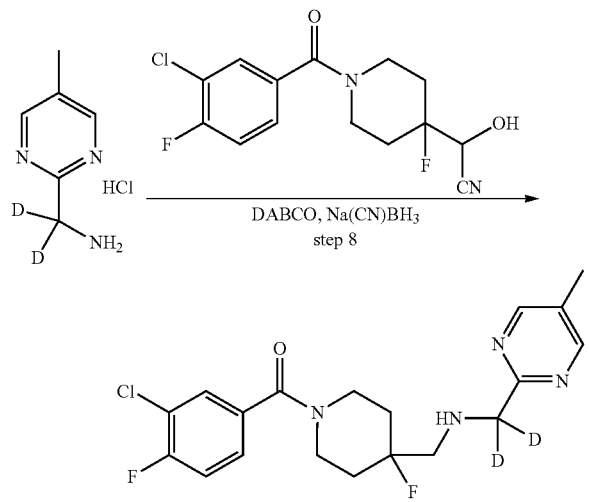

To a solution of 2-[1-[(3-chloro-4-fluorophenyl)carbonyl]-4-fluoropiperidin-4-yl]-2-hydroxyacetonitrile [Example 1, Step 4] (978 mg, 3.11 mmol, 1.00 equiv) in methanol (15 mL) was added (5-methylpyrimidin-2-yl)(d₂)methanamine hydrochloride [Example 9, Step 7] (500 mg, 3.11 mmol, 1.00 equiv), DABCO (1.22 g, 10.89 mmol, 3.50 equiv) and Na(CN)BH₃ (234.4 mg, 3.73 mmol, 1.20 equiv). The resulting solution was stirred overnight at 25° C. The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following: Column, XBridge Prep OBD C18 Column 5um, 30×150 mm; mobile phase, Water (10 mmol/L NH₄HCO₃) and ACN (34% ACN up to 34% in 7 min); Detector, UV 254/220 nm to afford 150 mg (12%) of ([1-[(3-chloro-4-fluorophenyl)carbonyl]-4-fluoropiperidin-4-yl]methyl) [(5-methylpyrimidin-2-yl)(d₂)methyl]amine as a white solid.

¹H NMR (400 MHz, DMSO-d₆) δ: 8.621-8.620 (m, 2H), 7.687-7.664 (m, 1H), 7.517-7.427 (m, 2H), 4.247 (m, 1H), 3.400-3.079 (m, 3H), 2.787-2.734 (m, 2H), 2.335-2.245 (m, 4H), 1.803-1.650 (m, 4H). LC-MS: m/z=397 [M+H]⁺.

Example 10: (3-chloro-4-fluorophenyl)(4-fluoro-4-((((5-(methyl-d₃)pyrimidin-2-yl)methyl)amino)methyl)piperidin-1-yl)methanone

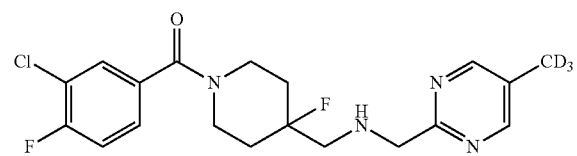 [SMILES: [2H]C([2H])([2H])c1cnc(CNCC2(F)CCN(C(=O)c3ccc(F)c(Cl)c3)CC2)nc1]

Step 1: 5-(bromomethyl)pyrimidine-2-carbonitrile

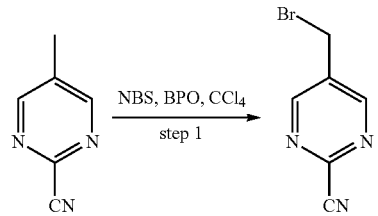

To a solution of 5-methylpyrimidine-2-carbonitrile [Example 8, Step 2] (8 g, 40.4 mmol, 1.00 equiv) in CCl₄ (100 mL) was added NBS (8.63 g, 48.5 mmol, 1.2 equiv) and BPO (488.8 mg, 2.02 mmol, 0.05 equiv). The resulting solution was stirred overnight at 80° C. The resulting solution was diluted with H₂O (100 mL). The resulting solution was extracted with DCM (3×100 mL). The organic layers were washed with water (3×70 mL) and brine (3×70 mL). The mixture was dried over anhydrous sodium sulfate and concentrated under vacuum. The residue was applied onto a silica gel column with ethyl acetate/petroleum ether (1:1) to afford 8 g (a mixture of 5-methylpyrimidine-2-carbonitrile and 5-(bromomethyl)pyrimidine-2-carbonitrile (1:1)) as a yellow solid. LC-MS: m/z=197[M+H]⁺.

Step 2: 5-(d₃)methylpyrimidine-2-carbonitrile

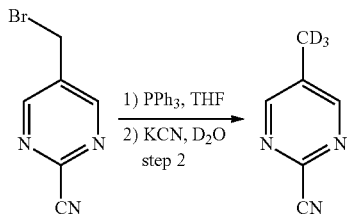 [SMILES: N#Cc1ncc(CBr)cn1 ; [2H]C([2H])([2H])c1cnc(C#N)nc1]

To a solution of the above mixture of 5-methylpyrimidine-2-carbonitrile and 5-(bromomethyl)pyrimidine-2-carbonitrile (1:1) [Example 10, Step 1] (8 g, 1.00 equiv) in tetrahydrofuran (100 mL) was added PPh₃ (15.9 g, 60.6 mmol, 1.50 equiv). The resulting solution was stirred overnight at 40° C. This was followed by the addition of D₂O (100 mL) and KCN (3.2 g, 36.84 mmol, 1.20 equiv). The resulting solution was stirred overnight at 55° C. The resulting solution was diluted with ethyl acetate (300 mL). The organic layers were washed with water (3×70 mL) and brine (3×70 mL). The mixture was dried over anhydrous sodium sulfate and concentrated under vacuum. The residue was applied onto a silica gel column with ethyl acetate/petroleum ether (2:1) to afford 700 mg of 5-(d)methylpyrimidine-2-carbonitrile as a yellow solid. LC-MS: m/z=123 [M+H]⁺.

¹H NMR (400 MHz, CDCl₃) δ: 8.69 (s, 2H).

Step 3: 5-(d₃)methylpyrimidine-2-carboxylic acid

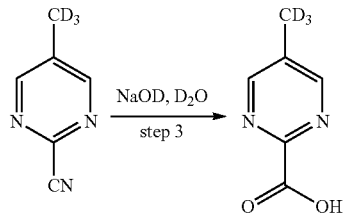 [SMILES: [2H]C([2H])([2H])c1cnc(C#N)nc1 ; [2H]C([2H])([2H])c1cnc(C(=O)O)nc1]

To a solution of 5-(d₃)methylpyrimidine-2-carbonitrile [Example 10, Step 2] (700 mg, 5.74 mmol, 1.00 equiv) in D₂O (10 mL) was added NaOD (3M in D₂O) (2.87 mL, 8.61 mmol, 1.50 equiv). The resulting solution was stirred for 3 h at 50° C. The pH value of the solution was adjusted to 4-5 with DCl (10% in D₂O). The resulting mixture was concentrated under vacuum to remove D₂O. The resulting solution was diluted with methanol (50 mL). The solids were collected by filtration. The filtrate was dried over anhydrous sodium sulfate and concentrated under vacuum to afford 700 mg (86.4%) of 5-(d₃)methylpyrimidine-2-carboxylic acid as a white solid. LC-MS: m/z=142[M+H]⁺.

Step 4: (d₃)methyl 5-(d₃)methylpyrimidine-2-carboxylate

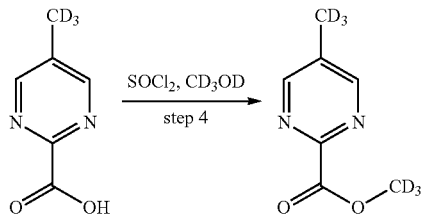 [SMILES: [2H]C([2H])([2H])c1cnc(C(=O)O)nc1 ; [2H]C([2H])([2H])OC(=O)c1ncc(C([2H])([2H])[2H])cn1]

To a solution of MeOD (15 mL) was added SOCl₂ (1.77 g, 14.89 mmol, 3.00 equiv) dropwise at 0° C. The resulting solution was stirred for 0.5 h at 25° C. This was followed by the addition of 5-(d₃)methylpyrimidine-2-carboxylic acid [Example 10, Step 3] (700 mg, 4.96 mmol, 1.00 equiv). The resulting solution was stirred for 1 h at 65° C. The resulting mixture was concentrated under vacuum to remove MeOD and SOCl₂. The resulting solution was diluted with H₂O (15 mL). The resulting solution was extracted with ethyl acetate (3×15 mL). The organic layers were dried over anhydrous sodium sulfate and concentrated under vacuum to afford 700 mg (89.3%) of (d₃)methyl 5-(d₃)methylpyrimidine-2-carboxylate as a yellow solid. LC-MS: m/z=159[M+H]⁺.

Step 5: [5-(d₃)methylpyrimidin-2-yl]methanol

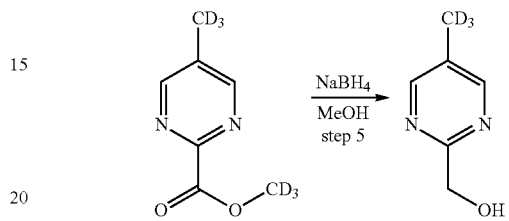

To a solution of (d₃)methyl 5-(d₃)methylpyrimidine-2-carboxylate [Example 10, Step 4] (700 mg, 4.43 mmol, 1.00 equiv) in methanol (25 mL) was added NaBH₄ (505.1 mg, 13.3 mmol, 3.00 equiv) at 0° C. The resulting solution was stirred for 3 h at 25° C. The reaction was then quenched by the addition of H₂O (10 mL). The resulting mixture was concentrated under vacuum to remove MeOH. The resulting solution was extracted with ethyl acetate (3×10 mL). The organic layers were dried over anhydrous sodium sulfate and concentrated under vacuum to afford 500 mg (88.9%) of [5-(d₃)methylpyrimidin-2-yl]methanol as a yellow solid. LC-MS: m/z=128 [M+H]⁺.

Step 6: 2-(bromomethyl)-5-(d₃)methylpyrimidine

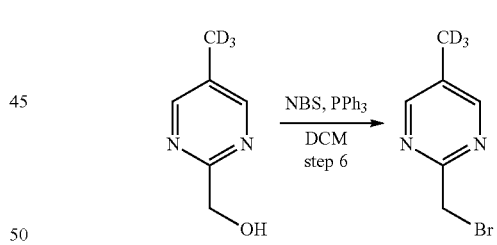

To a solution of [5-(d₃)methylpyrimidin-2-yl]methanol [Example 10, Step 5] (500 mg, 3.94 mmol, 1.00 equiv) in DCM (10 mL) was added PPh₃ (1.03 g, 3.94 mmol, 1.00 equiv) and NBS (701.3 mg, 2.02 mmol, 1.00 equiv) at 0° C. The resulting solution was stirred for 1 h at 0° C. The reaction was then quenched by the addition of H₂O (10 mL). The resulting solution was extracted with DCM (3×10 mL). The organic layers were dried over anhydrous sodium sulfate and concentrated under vacuum. The residue was applied onto a silica gel column with ethyl acetate/petroleum ether (1:2) to afford 300 mg (40.2%) of 2-(bromomethyl)-5-(d₃)methylpyrimidine as a yellow oil. LC-MS: m/z=190 [M+H]⁺.

Step 7: 2-(azidomethyl)-5-($^2$H$_3$)methylpyrimidine

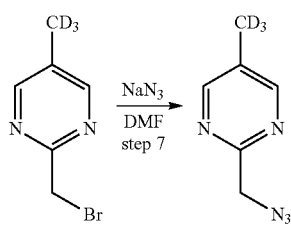 [SMILES: [2H]C([2H])([2H])c1cnc(CBr)nc1 ; [2H]C([2H])([2H])c1cnc(CN=[N+]=[N-])nc1 ; "NaN3"]

To a solution of 2-(bromomethyl)-5-(d$_3$)methylpyrimidine (300 mg, 1.59 mmol, 1.00 equiv) [Example 10, Step 6] in DMF (8 mL) was added NaN$_3$ (258.4 mg, 3.98 mmol, 2.50 equiv). The resulting solution was stirred for 1 h at 60° C. The reaction was then quenched by the addition of H$_2$O (20 mL). The resulting solution was extracted with ethyl acetate (3×20 mL). The organic layers were dried over anhydrous sodium sulfate and concentrated under vacuum to afford 250 mg (crude) of 2-(azidomethyl)-5-($^2$H$_3$)methylpyrimidine as a yellow oil. LC-MS: m/z=153[M+H]$^+$.

Step 8: tert-butyl N-[(5-(d$_3$)methylpyrimidin-2-yl)methyl]carbamate

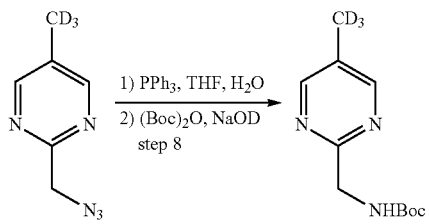 [SMILES: [2H]C([2H])([2H])c1cnc(CN=[N+]=[N-])nc1 ; [2H]C([2H])([2H])c1cnc(CNC(=O)OC(C)(C)C)nc1]

To a solution of 2-(azidomethyl)-5-($^2$H$_3$)methylpyrimidine [Example 10, Step 7] (250 mg, 1.64 mmol, 1.00 equiv) in tetrahydrofuran (8 mL) and D$_2$O (2 mL) was added PPh$_3$ (560.2 mg, 2.14 mmol, 1.30 equiv). The resulting solution was stirred for 2.5 h at 70° C. The reaction was then quenched by the addition of D$_2$O (4 mL). This was followed by the addition of D$_2$O (2 mL), NaOD (3M in D$_2$O) (0.82 mL, 2.46 mmol, 1.50 equiv), and (Boc)$_2$O (536.3 mg, 2.46 mmol, 1.50 equiv). The resulting solution was stirred overnight at 25° C. The resulting solution was extracted with ethyl acetate (3×20 mL). The organic layers were washed with water (3×10 mL) and brine (3×10 mL). The mixture was dried over anhydrous sodium sulfate and concentrated under vacuum. The residue was applied onto a silica gel column with ethyl acetate/petroleum ether (1:20) to afford 300 mg (80.5%) of tert-butyl N-[(5-($^2$H$_3$)methylpyrimidin-2-yl)methyl]carbamate as yellow oil. LC-MS: m/z=227 [M+H]$^+$.

Step 9: [5-(d$_3$)methylpyrimidin-2-yl]methanamine hydrochloride

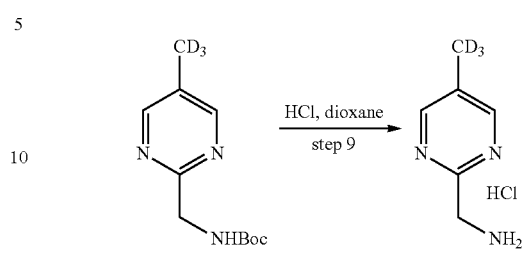

To a solution of tert-butyl N-[(5-(d$_3$)methylpyrimidin-2-yl)methyl]carbamate [Example 10, Step 8] (300 mg, 1.33 mmol, 1.00 equiv) in dichloromethane (5 mL) was added hydrogen chloride (4M in dioxane) (5 mL). The resulting solution was stirred overnight at 25° C. The resulting mixture was concentrated under vacuum to afford 240 mg (crude) of [5-(d$_3$)methylpyrimidin-2-yl]methanamine hydrochloride as a yellow solid.

Step 10: ([1-[(3-chloro-4-fluorophenyl)carbonyl]-4-fluoropiperidin-4-yl]methyl)[(5-(d$_3$)methylpyrimidin-2-yl)methyl]amine

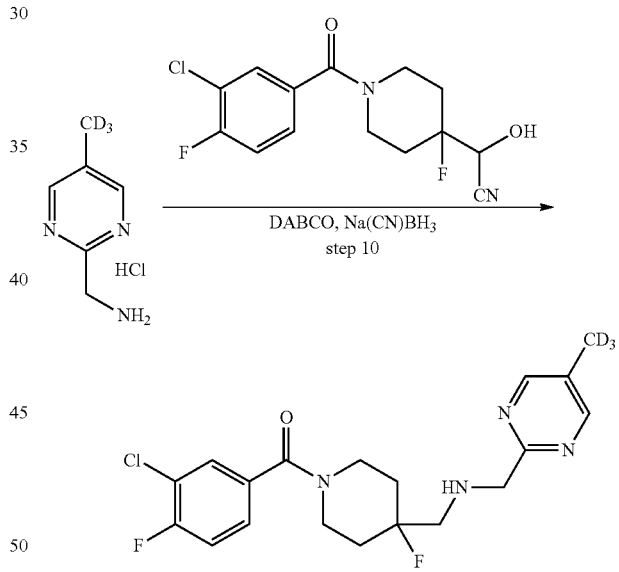

To a solution of 2-[1-[(3-chloro-4-fluorophenyl)carbonyl]-4-fluoropiperidin-4-yl]-2-hydroxyacetonitrile [Example 1, Step 4] (468 mg, 1.49 mmol, 1.00 equiv) in methanol (5 mL) was added [5-(d$_3$)methylpyrimidin-2-yl]methanamine hydrochloride [Example 10, Step 9] (240 mg, 1.49 mmol, 1.00 equiv), DABCO (584 mg, 5.22 mmol, 3.50 equiv) and Na(CN)BH$_3$ (112.3 mg, 1.79 mmol, 1.20 equiv). The resulting solution was stirred overnight at 25° C. The resulting mixture was concentrated under vacuum to remove methanol. The resulting solution was diluted with ethyl acetate (50 mL). The organic layers were washed with water (3×10 mL) and brine (3×10 mL). The mixture was dried over anhydrous sodium sulfate and concentrated under vacuum. The crude product was purified by Prep-HPLC with the following: Column, XBridge Prep OBD C18 Column Sum, 19×150 mm; mobile phase, Water (10 mmol/L NH$_4$HCO$_3$) and ACN (28% ACN up to 29% in 13 min); Detector, UV 254/220 nm to afford 51 mg (8.6%) of ([1-[(3-chloro-4-fluorophenyl)carbonyl]-4-fluoropiperidin-4-yl]methyl) [(5-(d$_3$)methylpyrimidin-2-yl)methyl]amine as a white solid.

$^1$H NMR (400 MHz, DMSO-d$_6$) δ: 8.616 (s, 2H), 7.684-7.661 (m, 1H), 7.514-7.423 (m, 2H), 4.242 (m, 1H), 3.889 (s, 2H), 3.393-3.069 (m, 3H), 2.788-2.736 (m, 2H), 2.330-2.257 (m, 1H), 1.798-1.645 (m, 4H). LC-MS: m/z=398 [M+H]$^+$.

Example 11: (3-chloro-4-fluorophenyl)(4-fluoro-4-(((((5-(methyl-d$_3$)pyrimidin-2-yl)methyl-d$_2$) amino)methyl)piperidin-1-yl)methanone

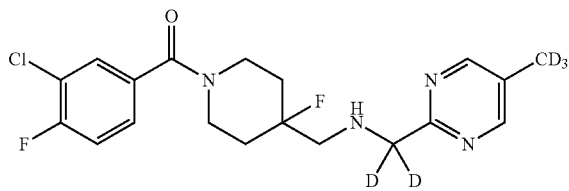 [SMILES: [2H]C([2H])([2H])c1cnc(C([2H])([2H])NCC2(F)CCN(C(=O)c3ccc(F)c(Cl)c3)CC2)nc1]

Step 1: [5-(d$_3$)methylpyrimidin-2-yl]($^2$H$_2$)methanol

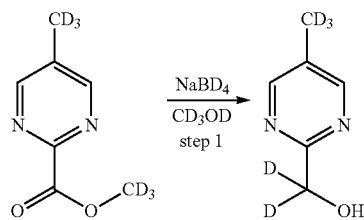 [SMILES: [2H]C([2H])([2H])OC(=O)c1ncc(C([2H])([2H])[2H])cn1 ; "NaBD4" ; [2H]C([2H])([2H])c1cnc(C([2H])([2H])O)nc1]

To a solution of (d$_3$)methyl 5-(d$_3$)methylpyrimidine-2-carboxylate [Example 10, Step 4] (1 g, 6.33 mmol, 1.00 equiv) in MeOD (15 mL) was added NaBD$_4$ (797.5 mg, 19.00 mmol, 3.00 equiv) at 0° C. The resulting solution was stirred for 3 h at 25° C. The reaction was then quenched by the addition of D$_2$O (5 mL). The resulting mixture was concentrated under vacuum to remove MeOD. The resulting solution was extracted with ethyl acetate (3×10 mL). The organic layers were dried over anhydrous sodium sulfate and concentrated under vacuum to afford 700 mg (85.7%) of [5-(d$_3$)methylpyrimidin-2-yl]($^2$H$_2$)methanol as a yellow solid. LC-MS: m/z=130 [M+H]$^+$.

Step 2: 2-[bromo(d$_2$)methyl]-5-($^2$H$_3$)methylpyrimidine

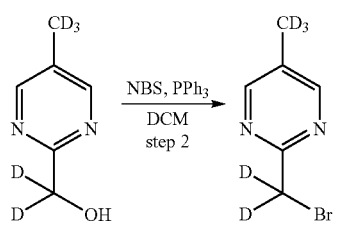

To a solution of [5-(d$_3$)methylpyrimidin-2-yl](d$_2$)methanol [Example 11, Step 1] (700 mg, 5.42 mmol, 1.00 equiv) in DCM (10 mL) was added PPh$_3$ (1.42 g, 5.42 mmol, 1.00 equiv) and NBS (964.8 mg, 5.42 mmol, 1.00 equiv) at 0° C. The resulting solution was stirred for 1 h at 0° C. The reaction was then quenched by the addition of H$_2$O (10 mL). The resulting solution was extracted with DCM (3×15 mL). The organic layers were dried over anhydrous sodium sulfate and concentrated under vacuum. The residue was applied onto a silica gel column with ethyl acetate/petroleum ether (1:2) to afford 180 mg (17.4%) of 2-[bromo(d$_2$)methyl]-5-(d$_3$)methylpyrimidine as a yellow oil. LC-MS: m/z=192[M+H]$^+$.

Step 3: 2-[azido(d$_2$)methyl]-5-(d$_3$)methylpyrimidine

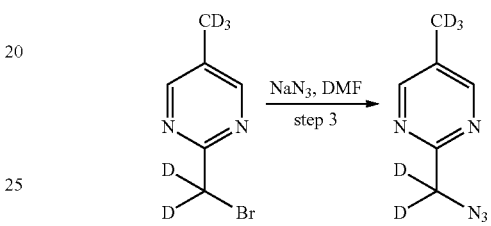

To a solution of 2-[bromo(d$_2$)methyl]-5-(d$_3$)methylpyrimidine [Example 11, Step 2] (180 mg, 0.94 mmol, 1.00 equiv) in DMF (5 mL) was added NaN$_3$ (153.1 mg, 2.36 mmol, 2.50 equiv). The resulting solution was stirred for 1 h at 60° C. The reaction was then quenched by the addition of H$_2$O (10 mL). The resulting solution was extracted with ethyl acetate (3×10 mL). The organic layers were dried over anhydrous sodium sulfate and concentrated under vacuum to afford 100 mg (crude) of 2-[azido($^2$H$_2$)methyl]-5-($^2$H$_3$)methylpyrimidine as a yellow oil. LC-MS: m/z=155[M+H]$^+$.

Step 4: tert-butyl N-[(5-(d$_3$)methylpyrimidin-2-yl)(d$_2$)methyl]carbamate

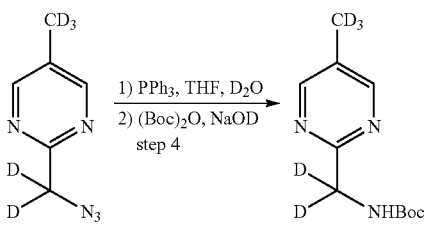

To a solution of 2-[azido(d$_2$)methyl]-5-(d$_3$)methylpyrimidine [Example 11, Step 3] (100 mg, 0.65 mmol, 1.00 equiv) in tetrahydrofuran (4 mL) and D$_2$O (1 mL) was added PPh$_3$ (221.2 mg, 0.84 mmol, 1.30 equiv). The resulting solution was stirred for 2.5 h at 70° C. The reaction was then quenched by the addition of D$_2$O (2 mL). This was followed by the addition of D$_2$O (1 mL), NaOD (3M in D$_2$O) (0.33 mL, 0.96 mmol, 1.50 equiv) and (Boc)$_2$O (212.56 mg, 0.96 mmol, 1.50 equiv). The resulting solution was stirred overnight at 25° C. The resulting solution was extracted with ethyl acetate (3×10 mL). The organic layers were washed with water (3×5 mL) and brine (3×5 mL). The mixture was dried over anhydrous sodium sulfate and concentrated under vacuum. The residue was applied onto a silica gel column with ethyl acetate/petroleum ether (1:20) to afford 120 mg (81%) of tert-butyl N-[(5-(d$_3$)methylpyrimidin-2-yl)(d$_2$) methyl]carbamate as yellow oil. LC-MS: m/z=229 [M+H]$^+$.

Step 5: [5-(d$_3$)methylpyrimidin-2-yl](d$_2$)methanamine hydrochloride

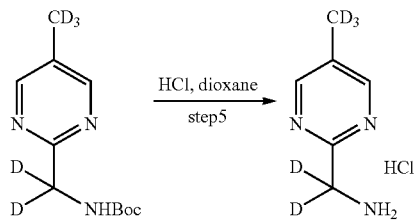 [SMILES: [2H]C([2H])([2H])c1cnc(C([2H])([2H])NC(=O)OC(C)(C)C)nc1 ; [2H]C([2H])([2H])c1cnc(C([2H])([2H])N)nc1 ; Cl]

To a solution of tert-butyl N-[(5-(d$_3$)methylpyrimidin-2-yl)(d$_2$)methyl]carbamate [Example 11, Step 4] (120 mg, 0.53 mmol, 1.00 equiv) in dichloromethane (5 mL) was added hydrogen chloride(4M in dioxane) (5 mL). The resulting solution was stirred overnight at 25° C. The resulting mixture was concentrated under vacuum to afford 100 mg (crude) of [5-(d$_3$)methylpyrimidin-2-yl](d$_2$)methanamine hydrochloride as a yellow solid.

Step 6: ([1-[(3-chloro-4-fluorophenyl)carbonyl]-4-fluoropiperidin-4-yl]methyl)[(5-(d$_3$)methylpyrimidin-2-yl)(d$_2$)methyl]amine

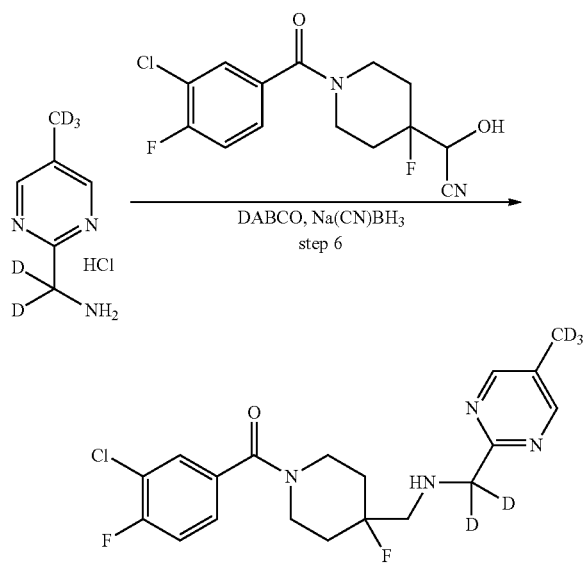

To a solution of 2-[1-[(3-chloro-4-fluorophenyl)carbonyl]-4-fluoropiperidin-4-yl]-2-hydroxyacetonitrile [Example 1, Step 4] (211.3 mg, 0.67 mmol, 1.10 equiv) in methanol (5 mL) was added [5-(d$_3$)methylpyrimidin-2-yl](d$_2$)methanamine hydrochloride [Example 11, Step 5] (100 mg, 0.61 mmol, 1.00 equiv), DABCO (239.1 mg, 2.14 mmol, 3.50 equiv), and Na(CN)BH$_3$ (46.0 mg, 0.73 mmol, 1.20 equiv). The resulting solution was stirred overnight at 25° C. The resulting mixture was concentrated under vacuum to remove methanol. The resulting solution was diluted with ethyl acetate (30 mL). The organic layers were washed with water (3×5 mL) and brine (3×5 mL). The mixture was dried over anhydrous sodium sulfate and concentrated under vacuum. The crude product was purified by Prep-HPLC with the following: Column, XBridge Prep OBD C18 Column Sum, 30×150 mm; mobile phase, Water (10 mmol/L NH$_4$HCO$_3$) and ACN (27% ACN up to 27% in 13.5 min); Detector, UV 254/220 nm to afford 46 mg (18.9%) of ([1-[(3-chloro-4-fluorophenyl)carbonyl]-4-fluoropiperidin-4-yl]methyl)[(5-(d$_3$)methylpyrimidin-2-yl)(d$_2$) methyl]amine as a white solid.

$^1$H NMR (400 MHz, DMSO-d$_6$) δ: 8.617 (s, 2H), 7.684-7.661 (m, 1H), 7.514-7.423 (m, 2H), 4.241 (m, 1H), 3.395-3.067 (m, 3H), 2.781-2.728 (m, 2H), 2.316-2.257 (m, 1H), 1.797-1.631 (m, 4H). LC-MS: m/z=400 [M+H]$^+$.

Example 12: (3-chloro-4-fluorophenyl)(4-fluoro-4-((((5-methylpyrimidin-2-yl)methyl)amino)methyl-d$_2$)piperidin-1-yl)methanone

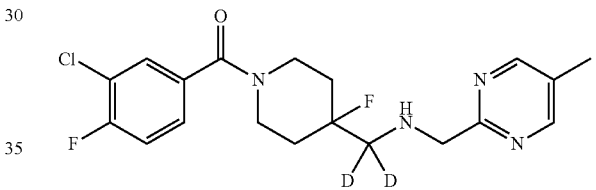

Step 1: (5-methylpyrimidin-2-yl)methanol

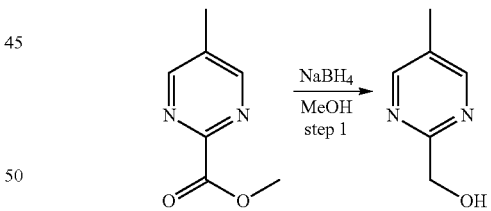

To a solution of methyl 5-methylpyrimidine-2-carboxylate [Example 9, Step 2] (2.5 g, 16.4 mmol, 1.00 equiv) in methanol (40 mL) was added NaBH$_4$ (1.87 g, 49.3 mmol, 3.00 equiv) at 0° C. The resulting solution was stirred for 3 h at 25° C. The reaction was then quenched by the addition of H$_2$O (40 mL). The resulting mixture was concentrated under vacuum to remove MeOH. The resulting solution was extracted with ethyl acetate (3×50 mL). The organic layers were dried over anhydrous sodium sulfate and concentrated under vacuum to afford 1.3 g (63.9%) of (5-methylpyrimidin-2-yl)methanol as a yellow solid. LC-MS: m/z=125 [M+H]$^+$.

Step 2: 2-(bromomethyl)-5-methylpyrimidine

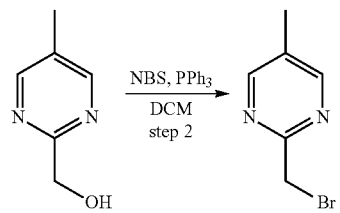

To a solution of (5-methylpyrimidin-2-yl)methanol [Example 12, Step 1] (1.3 g, 10.5 mmol, 1.00 equiv) in DCM (30 mL) was added PPh₃ (2.75 g, 10.5 mmol, 1.00 equiv) and NBS (1.87 mg, 10.5 mmol, 1.00 equiv) at 0° C. The resulting solution was stirred for 1 h at 0° C. The reaction was then quenched by the addition of H₂O (30 mL). The resulting solution was extracted with DCM (3×30 mL). The organic layers were dried over anhydrous sodium sulfate and concentrated under vacuum. The residue was applied onto a silica gel column with ethyl acetate/petroleum ether (1:2) to afford 700 mg (35.8%) of 2-(bromomethyl)-5-methylpyrimidine as a yellow oil. LC-MS: m/z=187[M+H]⁺.

Step 3: ([1-[(3-chloro-4-fluorophenyl)carbonyl]-4-fluoropiperidin-4-yl] (d₂)methyl) [(5-methylpyrimidin-2-yl)methyl]amine

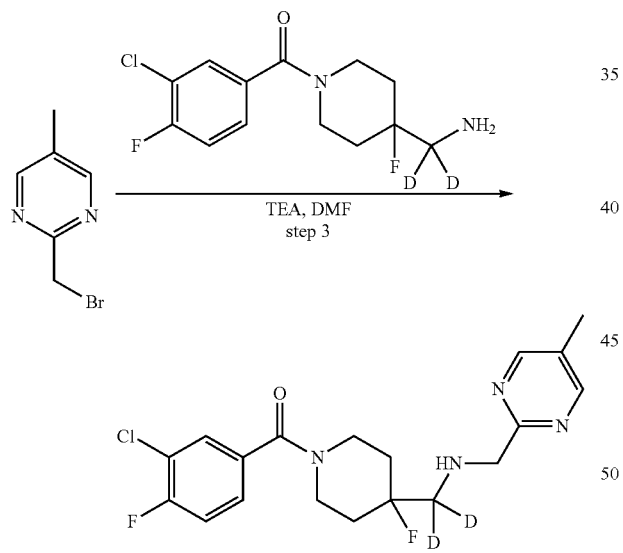

To a solution of [1-[(3-chloro-4-fluorophenyl)carbonyl]-4-fluoropiperidin-4-yl](d₂)methanamine [Example 2 Step 10] (1 g, 3.75 mmol, 1.00 equiv) in DMF (15 mL) was added 2-(bromomethyl)-5-methylpyrimidine [Example 12, Step 2] (700 mg, 3.76 mmol, 1.00 equiv) and TEA (569.64 mg, 5.64 mmol, 1.50 equiv). The resulting solution was stirred overnight at 25° C. The reaction was then quenched by the addition of H₂O (40 mL). The resulting solution was extracted with ethyl acetate (3×50 mL). The organic layers were washed with water (3×20 mL) and brine (3×20 mL). The mixture was dried over anhydrous sodium sulfate and concentrated under vacuum. The crude product was purified by Prep-HPLC with the following: Column,)(Bridge Prep OBD C18 Column Sum, 30×150 mm; mobile phase, Water (10 mmol/L NH₄HCO₃) and ACN (25% ACN up to 55% in 7 min); Detector, UV 254/220 nm to afford 130 mg (8.7%) of ([1-[(3-chloro-4-fluorophenyl)carbonyl]-4-fluoropiperidin-4-yl](d₂)methyl)[(5-methylpyrimidin-2-yl)methyl]amine as a white solid.

¹H NMR (400 MHz, DMSO-d₆) δ: 8.617-8.615 (m, 2H), 7.683-7.660 (m, 1H), 7.514-7.422 (m, 2H), 4.237 (m, 1H), 3.887 (s, 2H), 3.399-3.071 (m, 3H), 2.312 (s, 1H), 2.256 (s, 3H), 1.795-1.629 (m, 4H). LC-MS: m/z=397 [M+H]⁺.

Example 13: ([1-[(3-chloro-4-fluorophenyl)carbonyl]-4-fluoro(d₈)piperidin-4-yl](d)methyl)[(5-methylpyrimidin-2-yl)methyl]amine

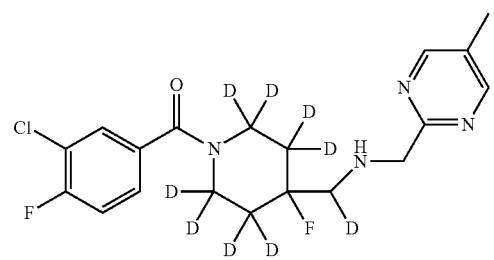 [SMILES: [2H]C(NCc1ncc(C)cn1)C1(F)C([2H])([2H])C([2H])([2H])N(C(=O)c2ccc(F)c(Cl)c2)C([2H])([2H])C1([2H])[2H]]

Step 1: ([1-[(3-chloro-4-fluorophenyl)carbonyl]-4-fluoro(d₈)piperidin-4-yl](d)methyl)[(5-methylpyrimidin-2-yl)methyl]amine

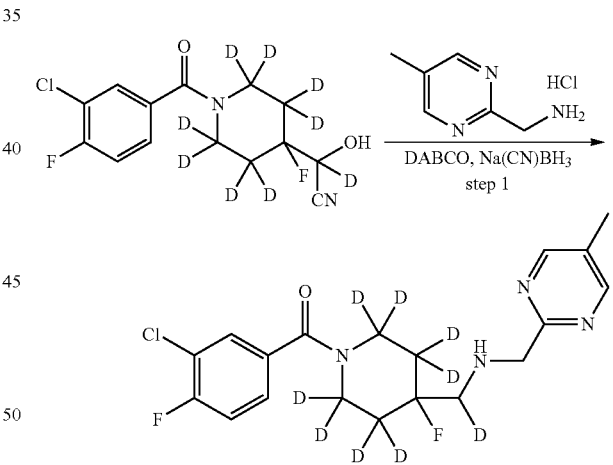

To a solution of 2-[1-[(3-chloro-4-fluorophenyl)carbonyl]-4-fluoro(d₈)piperidin-4-yl]-2-hydroxy(d)acetonitrile [Example 7, Step 9] (600 mg, 1.848 mmol, 1.00 equiv) in methanol (5 mL) was added (5-methylpyrimidin-2-yl)methanamine hydrochloride [Example 8, Step 2] (443.5 mg, 2.772 mmol, 1.50 equiv), DABCO (728.2 mg, 6.46 mmol, 3.50 equiv) and Na(CN)BH₃ (140.0 mg, 2.22 mmol, 1.20 equiv). The resulting solution was stirred overnight at 25° C. The resulting mixture was concentrated under vacuum to remove methanol. The resulting solution was diluted with EA (50 mL). The organic layers were washed with water (3×10 mL) and brine (3×10 mL). The mixture was dried over anhydrous sodium sulfate and concentrated under vacuum. The crude product was purified by Prep-HPLC with the following conditions: Column, XBridge Prep C18 OBD Column 19×150 mm; mobile phase, Water (10 mmol $NH_4HCO_3$) and ACN (32% ACN in 8 min); Detector, UV 254/220 nm to afford 66 mg (8.6%) of ([1-[(3-chloro-4-fluorophenyl)carbonyl]-4-fluoro($d_8$)piperidin-4-yl](d) methyl)[(5-methylpyrimidin-2-yl)methyl]amine as a white solid.

$^1$H NMR (400 MHz, DMSO-$d_6$) δ: 8.622 (m, 2H), 7.689-7.666 (m, 1H), 7.520-7.428 (m, 2H), 3.894 (s, 2H), 2.792-2.720 (m, 2H), 2.336-2.239 (s, 3H). LC-MS: m/z=404 [M+H]$^+$.

Example 14: (3-Chloro-4-Fluorophenyl)(4-Fluoro-4-(((((5-Methylpyrimidin-2-yl)methyl)amino) methyl) piperidin-1-yl-2,2,3,3,5,5,6,6-$d_8$)methanone

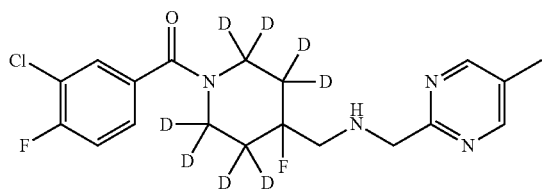 [SMILES: [2H]C1([2H])N(C(=O)c2ccc(F)c(Cl)c2)C([2H])([2H])C([2H])([2H])C(F)(CNCc2ncc(C)cn2)C1([2H])[2H]]

Step 1: 2-(1-(3-chloro-4-fluorobenzoyl)-4-fluoropiperidin-4-yl-2,2,3,3,5,5,6,6-$d_8$)-2-hydroxyacetonitrile

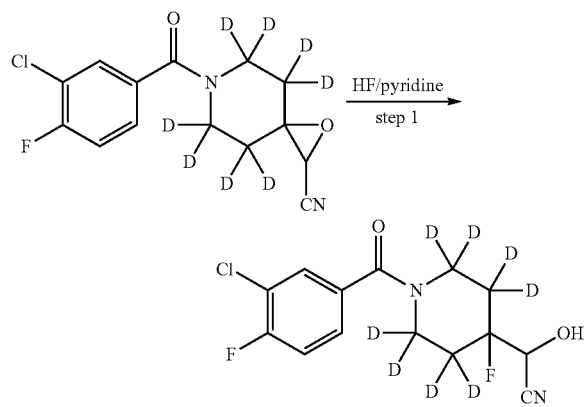

6-(3-chloro-4-fluorobenzoyl)-1-oxa-6-azaspiro[2.5]octane-2-carbonitrile-4,4,5,5,7,7,8,8-$d_8$ (Example 7, step 4) is treated with hydrogen fluoride and pyridine to provide 2-(1-(3-chloro-4-fluorobenzoyl)-4-fluoropiperidin-4-yl-2,2,3,3,5,5,6,6-$d_8$)-2-hydroxyacetonitrile.

Step 2: (3-chloro-4-fluorophenyl)(4-fluoro-4-(((((5-methylpyrimidin-2-yl)methyl) amino)methyl)piperidin-1-yl-2,2,3,3,5,5,6,6-$d_8$)methanone

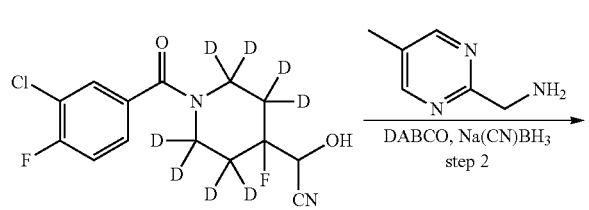

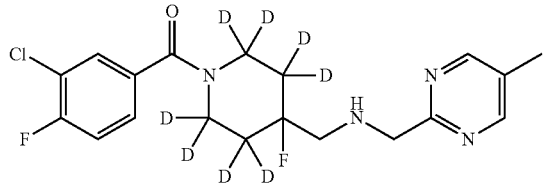

2-(1-(3-chloro-4-fluorobenzoyl)-4-fluoropiperidin-4-yl-2,2,3,3,5,5,6,6-$d_8$)-2-hydroxy acetonitrile (step 1) and (5-methylpyrimidin-2-yl)methanamine are treated with 1,4-diazabicyclo[2.2.2]octane and sodium cyanoborohydride to provide (3-chloro-4-fluorophenyl)(4-fluoro-4-(((5-methylpyrimidin-2-yl)methyl)amino)methyl)piperidin-1-yl-2,2,3,3,5,5,6,6-$d_8$) methanone.

The following compounds in Table 1 can generally be made using the methods described above:

TABLE 1

| No. | Structure |
|---|---|
| 15 | 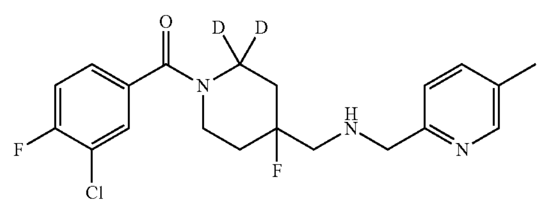 [SMILES: [2H]C1([2H])CC(F)(CNCc2ccc(C)cn2)CCN1C(=O)c1ccc(F)c(Cl)c1] |
| 16 | 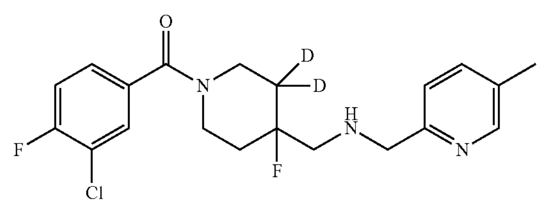 [SMILES: [2H]C1([2H])CN(C(=O)c2ccc(F)c(Cl)c2)CCC1(F)CNCc1ccc(C)cn1] |
| 17 | 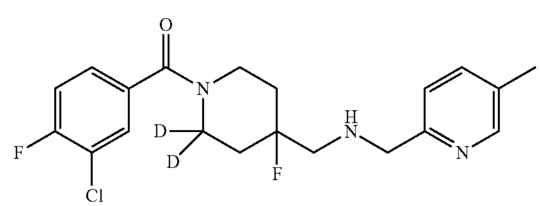 [SMILES: [2H]C1([2H])CC(F)(CNCc2ccc(C)cn2)CCN1C(=O)c1ccc(F)c(Cl)c1] |
| 18 | 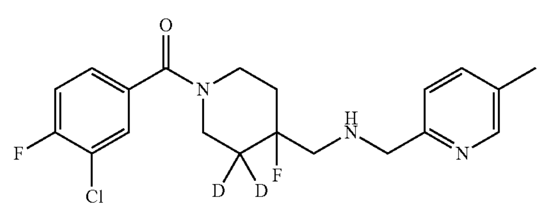 [SMILES: [2H]C1([2H])CN(C(=O)c2ccc(F)c(Cl)c2)CCC1(F)CNCc1ccc(C)cn1] |
| 19 | 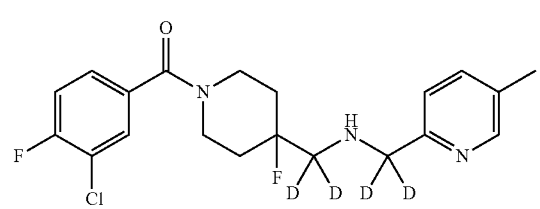 [SMILES: [2H]C([2H])(NC([2H])([2H])C1(F)CCN(C(=O)c2ccc(F)c(Cl)c2)CC1)c1ccc(C)cn1] |

TABLE 1-continued

| No. | Structure |
|---|---|
| 20 | 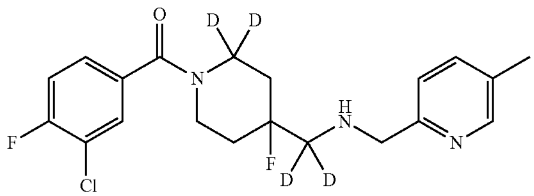 [SMILES: [2H]C1([2H])CC(F)(C([2H])([2H])NCc2ccc(C)cn2)CCN1C(=O)c1ccc(F)c(Cl)c1] |
| 21 | 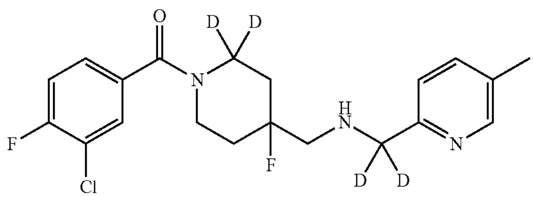 [SMILES: [2H]C([2H])(NCC1(F)CCN(C(=O)c2ccc(F)c(Cl)c2)C([2H])([2H])C1)c1ccc(C)cn1] |
| 22 | 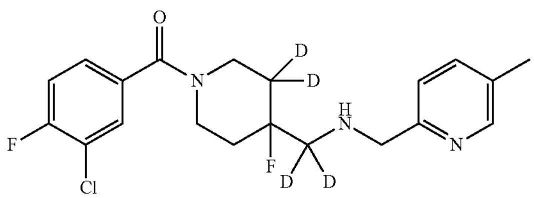 |
| 23 | 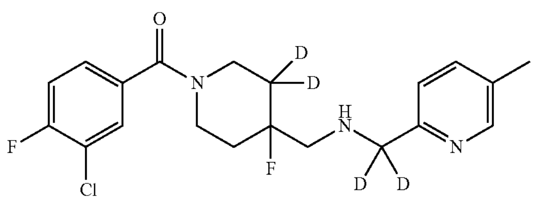 [SMILES: [2H]C([2H])(NCC1(F)CCN(C(=O)c2ccc(F)c(Cl)c2)CC1([2H])[2H])c1ccc(C)cn1] |
| 24 | 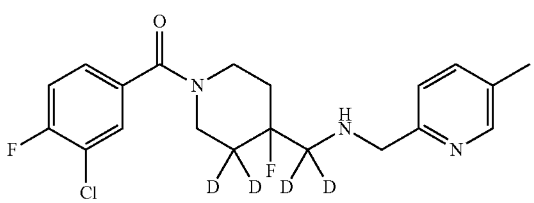 [SMILES: [2H]C1([2H])CN(C(=O)c2ccc(F)c(Cl)c2)CCC1(F)C([2H])([2H])NCc1ccc(C)cn1] |
| 25 | 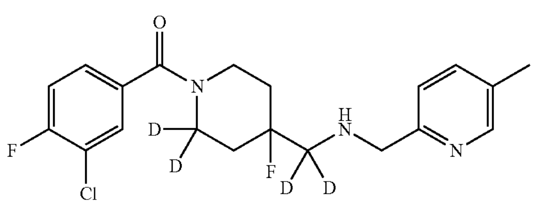 [SMILES: [2H]C1([2H])CC(F)(C([2H])([2H])NCc2ccc(C)cn2)CCN1C(=O)c1ccc(F)c(Cl)c1] |
| 26 | 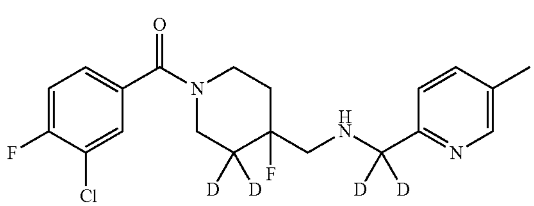 [SMILES: [2H]C([2H])(NCC1(F)CCN(C(=O)c2ccc(F)c(Cl)c2)CC1([2H])[2H])c1ccc(C)cn1] |
| 27 | |
| 28 | |
| 29 | |
| 30 | |
| 31 | |
| 32 | |
| 33 | |

TABLE 1-continued

| No. | Structure |
|-----|-----------|
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |

TABLE 1-continued

| No. | Structure |
|-----|-----------|
| 49  |           |
| 50  |           |
| 51  |           |
| 52  |           |
| 53  |           |
| 54  |           |
| 55  |           |
| 56  | 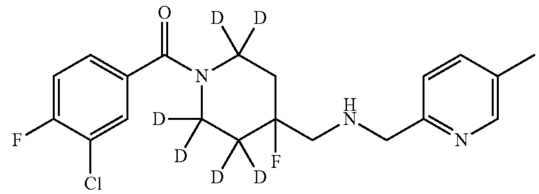 [SMILES: [2H]C1([2H])CC(F)(CNCc2ccc(C)cn2)C([2H])([2H])C([2H])([2H])N1C(=O)c1ccc(F)c(Cl)c1]          |
| 57  | 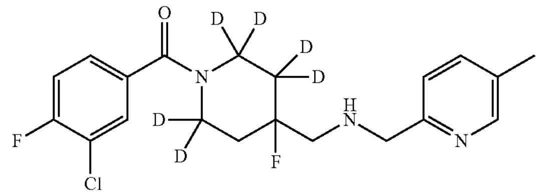 [SMILES: [2H]C1([2H])CC(F)(CNCc2ccc(C)cn2)C([2H])([2H])C([2H])([2H])N1C(=O)c1ccc(F)c(Cl)c1]          |
| 58  | 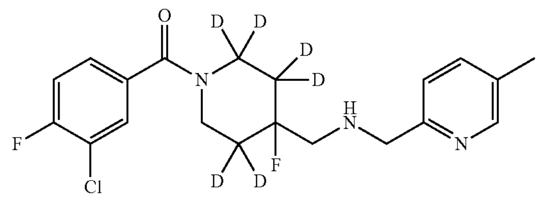 [SMILES: [2H]C1([2H])CN(C(=O)c2ccc(F)c(Cl)c2)C([2H])([2H])C([2H])([2H])C1(F)CNCc1ccc(C)cn1]          |
| 59  | 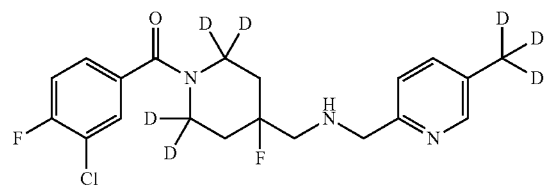 [SMILES: [2H]C([2H])([2H])c1ccc(CNCC2(F)CC([2H])([2H])N(C(=O)c3ccc(F)c(Cl)c3)C([2H])([2H])C2)nc1]          |
| 60  | 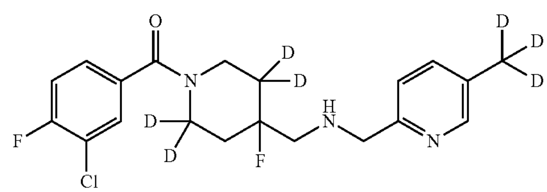 [SMILES: [2H]C([2H])([2H])c1ccc(CNCC2(F)CC([2H])([2H])N(C(=O)c3ccc(F)c(Cl)c3)CC2([2H])[2H])nc1]          |
| 61  | 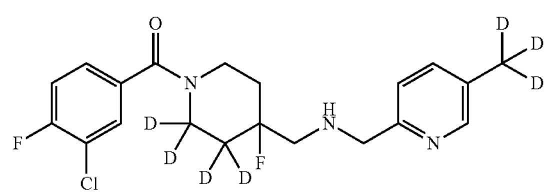 [SMILES: [2H]C([2H])([2H])c1ccc(CNCC2(F)CCN(C(=O)c3ccc(F)c(Cl)c3)C([2H])([2H])C2([2H])[2H])nc1]          |
| 62  | 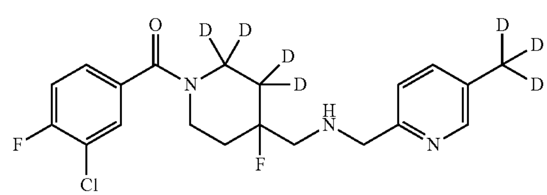 [SMILES: [2H]C([2H])([2H])c1ccc(CNCC2(F)CCN(C(=O)c3ccc(F)c(Cl)c3)C([2H])([2H])C2([2H])[2H])nc1]          |
| 63  | 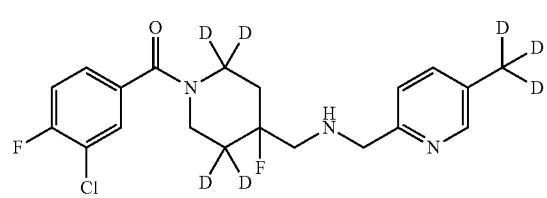 [SMILES: [2H]C([2H])([2H])c1ccc(CNCC2(F)CC([2H])([2H])N(C(=O)c3ccc(F)c(Cl)c3)CC2([2H])[2H])nc1]          |

TABLE 1-continued

| No. | Structure |
|-----|-----------|
| 64 | (structure) |
| 65 | (structure) |
| 66 | (structure) |
| 67 | (structure) |
| 68 | (structure) |
| 69 | (structure) |
| 70 | (structure) |
| 71 | (structure) |
| 72 | (structure) |
| 73 | (structure) |
| 74 | (structure) |
| 75 | (structure) |
| 76 | (structure) |
| 77 | (structure) |
| 78 | (structure) |
| 79 | (structure) |

TABLE 1-continued

| No. | Structure |
|---|---|
| 80 | *(structure)* |
| 81 | *(structure)* |
| 82 | *(structure)* |
| 83 | *(structure)* |
| 84 | *(structure)* |
| 85 | *(structure)* |
| 86 | *(structure)* |
| 87 | *(structure)* |
| 88 | *(structure)* |
| 89 | *(structure)* |
| 90 | *(structure)* |
| 91 | *(structure)* |
| 92 | *(structure)* |
| 93 | *(structure)* |
| 94 | *(structure)* |
| 95 | *(structure)* |

TABLE 1-continued
| No. | Structure |
|---|---|
| 96 | 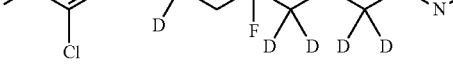 |
| 97 | 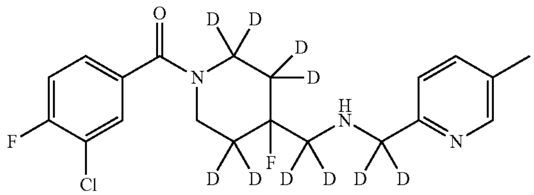 [SMILES: [2H]C([2H])(NC([2H])([2H])C1(F)C([2H])([2H])CN(C(=O)c2ccc(F)c(Cl)c2)C([2H])([2H])C1([2H])[2H])c1ccc(C)cn1] |
| 98 | 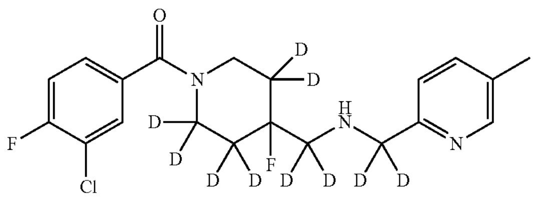 [SMILES: [2H]C([2H])(NC([2H])([2H])C1(F)C([2H])([2H])CN(C(=O)c2ccc(F)c(Cl)c2)C([2H])([2H])C1([2H])[2H])c1ccc(C)cn1] |
| 99 | 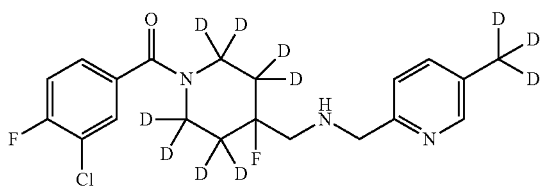 [SMILES: [2H]C([2H])([2H])c1ccc(CNCC2(F)C([2H])([2H])C([2H])([2H])N(C(=O)c3ccc(F)c(Cl)c3)C([2H])([2H])C2([2H])[2H])nc1] |
| 100 | 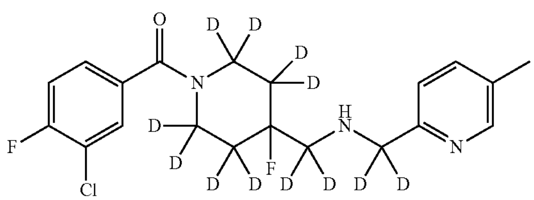 [SMILES: [2H]C([2H])(NC([2H])([2H])C1(F)C([2H])([2H])C([2H])([2H])N(C(=O)c2ccc(F)c(Cl)c2)C([2H])([2H])C1([2H])[2H])c1ccc(C)cn1] |
| 101 | 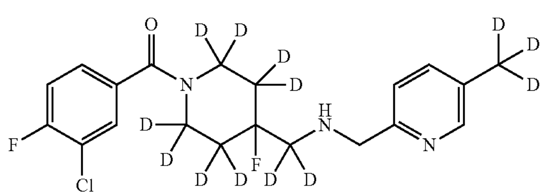 [SMILES: [2H]C([2H])([2H])c1ccc(CNC([2H])([2H])C2(F)C([2H])([2H])C([2H])([2H])N(C(=O)c3ccc(F)c(Cl)c3)C([2H])([2H])C2([2H])[2H])nc1] |
| 102 | 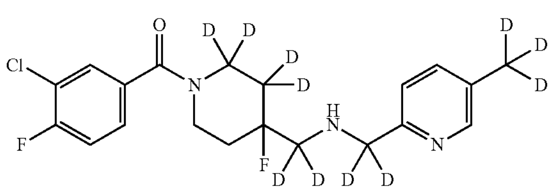 [SMILES: [2H]C([2H])([2H])c1ccc(C([2H])([2H])NC([2H])([2H])C2(F)CCN(C(=O)c3ccc(F)c(Cl)c3)C([2H])([2H])C2([2H])[2H])nc1] |
| 103 | 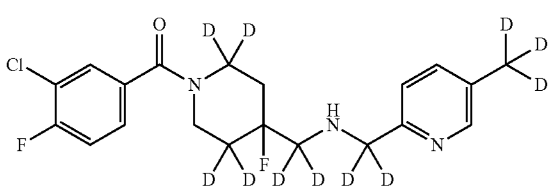 [SMILES: [2H]C([2H])([2H])c1ccc(C([2H])([2H])NC([2H])([2H])C2(F)CC([2H])([2H])N(C(=O)c3ccc(F)c(Cl)c3)CC2([2H])[2H])nc1] |
| 104 | 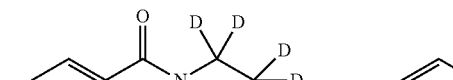 |
| 105 | |
| 106 | |
| 107 | |
| 108 | |
| 109 | |
| 110 | |
| 111 | |

TABLE 1-continued
| No. | Structure |
|---|---|
| 112 | 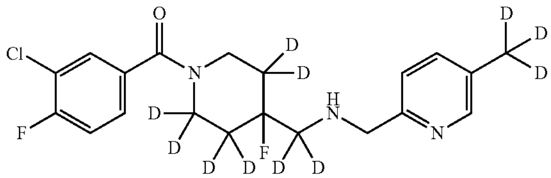 [SMILES: [2H]C([2H])([2H])c1ccc(CNC([2H])([2H])C2(F)C([2H])([2H])CN(C(=O)c3ccc(F)c(Cl)c3)C([2H])([2H])C2([2H])[2H])nc1] |
| 113 | 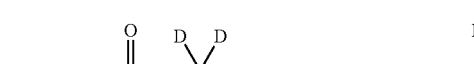 |
| 114 | 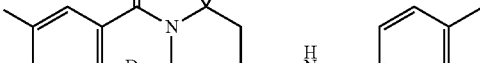 |
| 115 | 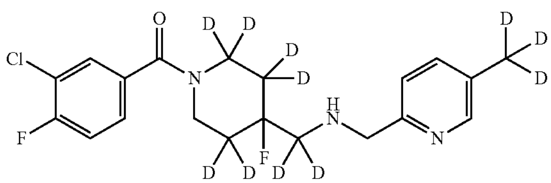 [SMILES: [2H]C([2H])([2H])c1ccc(CNC([2H])([2H])C2(F)C([2H])([2H])CN(C(=O)c3ccc(F)c(Cl)c3)C([2H])([2H])C2([2H])[2H])nc1] |
| 116 | 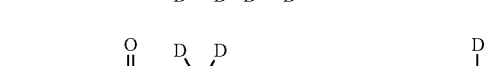 |
| 117 | 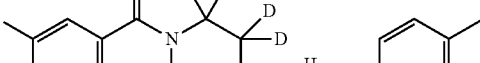 |
| 118 | 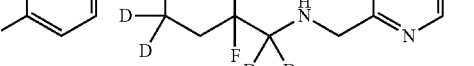 |
| 119 | 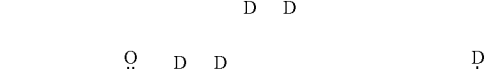 |
| 120 | 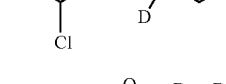 |
| 121 | 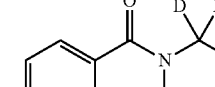 |
| 122 | 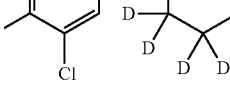 |
| 123 | 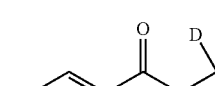 |
| 124 | 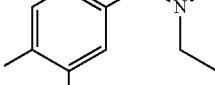 |
| 125 | 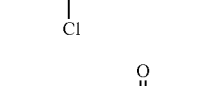 |
| 126 | 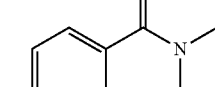 |
| 127 | 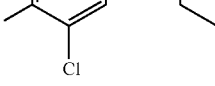 |

TABLE 1-continued

| No. | Structure |
|-----|-----------|
| 128 | (structure) |
| 129 | (structure) |
| 130 | (structure) |
| 131 | (structure) |
| 132 | (structure) |
| 133 | (structure) |
| 134 | (structure) |
| 135 | (structure) |
| 136 | (structure) |
| 137 | (structure) |
| 138 | (structure) |
| 139 | (structure) |
| 140 | (structure) |
| 141 | (structure) |
| 142 | (structure) |

TABLE 1-continued
| No. | Structure |
|---|---|
| 143 | 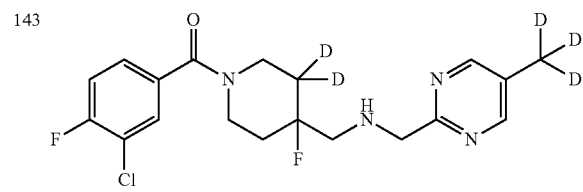 |
| 144 | 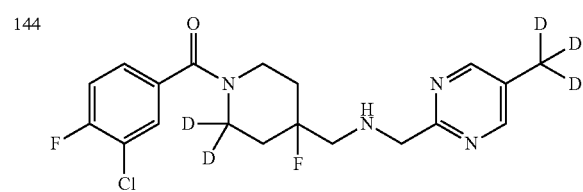 |
| 145 | 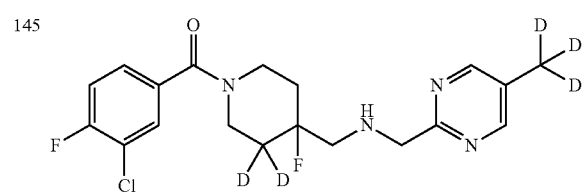 |
| 146 | 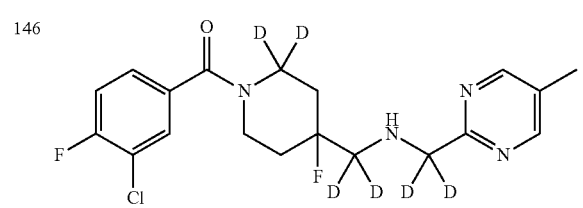 |
| 147 | 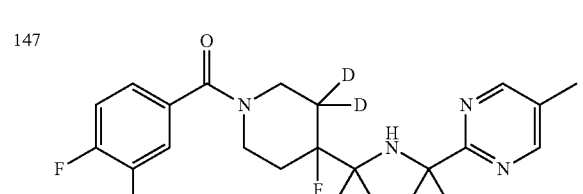 |
| 148 | 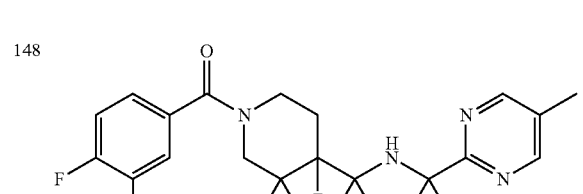 |
| 149 | 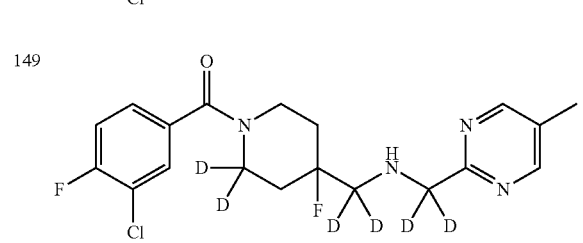 |
TABLE 1-continued
| No. | Structure |
|---|---|
| 150 | 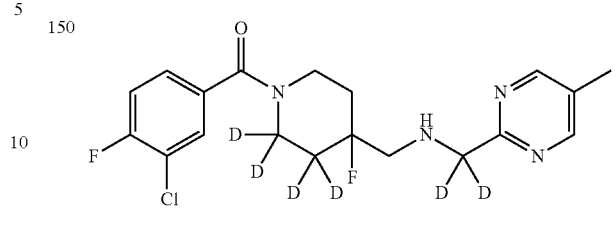 |
| 151 | 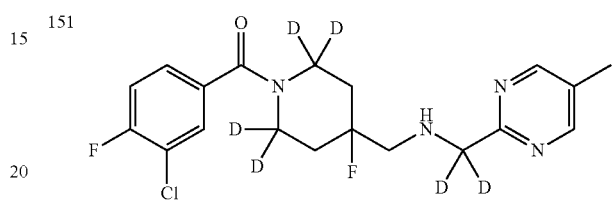 |
| 152 | 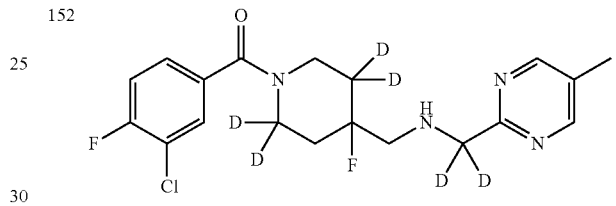 |
| 153 | 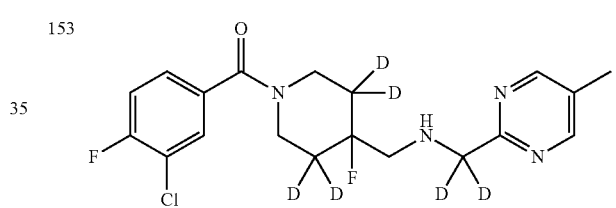 |
| 154 | 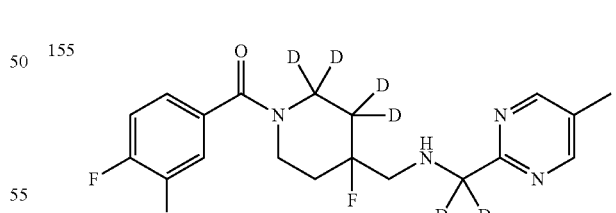 |
| 155 | 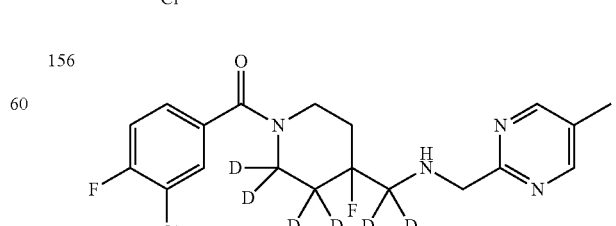 |
| 156 | 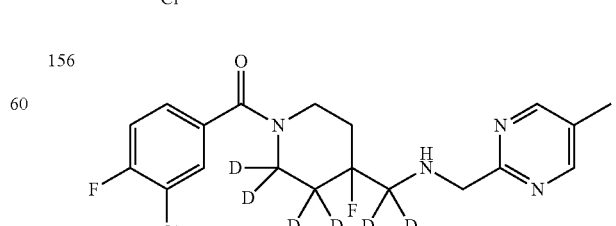 |

TABLE 1-continued

| No. | Structure |
|---|---|
| 157 | (structure) |
| 158 | (structure) |
| 159 | (structure) |
| 160 | (structure) |
| 161 | (structure) |
| 162 | (structure) |
| 163 | (structure) |
| 164 | (structure) |
| 165 | (structure) |
| 166 | (structure) |
| 167 | (structure) |
| 168 | (structure) |
| 169 | (structure) |
| 170 | (structure) |
| 171 | (structure) |

TABLE 1-continued
| No. | Structure |
|---|---|
| 172 | 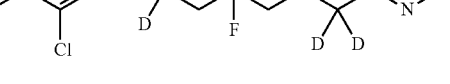 |
| 173 | 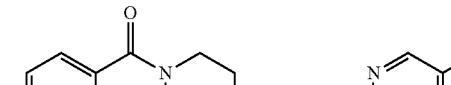 |
| 174 | 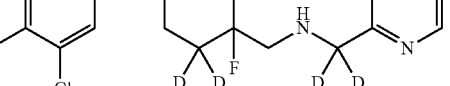 |
| 175 | 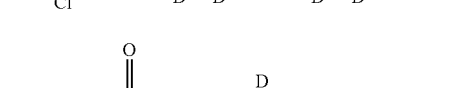 |
| 176 | 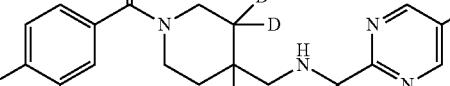 |
| 177 | 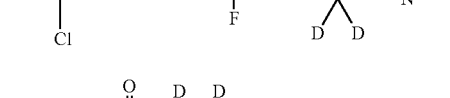 |
| 178 | 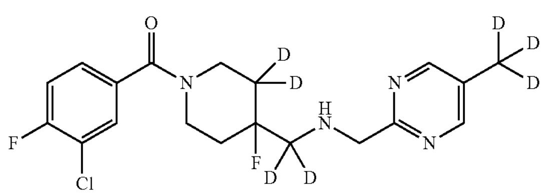 |
| 179 | 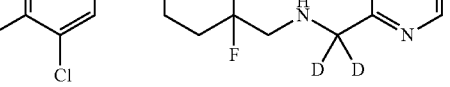 |
| 180 | 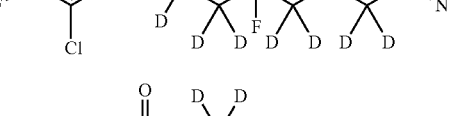 |
| 181 | 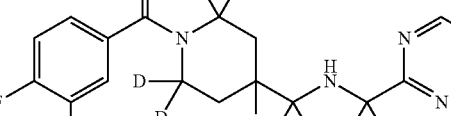 |
| 182 | 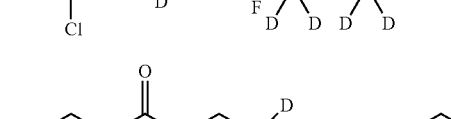 |
| 183 | 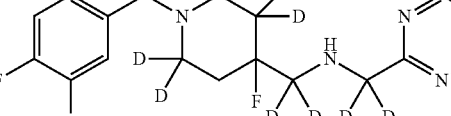 |
| 184 | 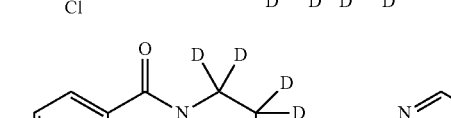 |
| 185 | 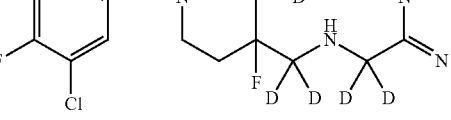 |
| 186 | 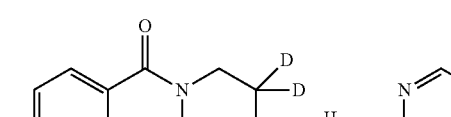 |
| 187 | 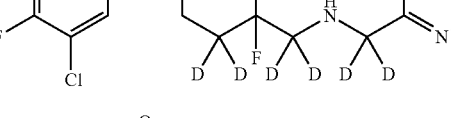 |

TABLE 1-continued

| No. | Structure |
|---|---|
| 188 | 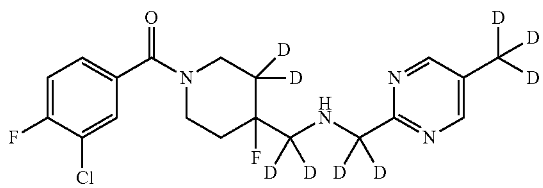 |
| 189 | 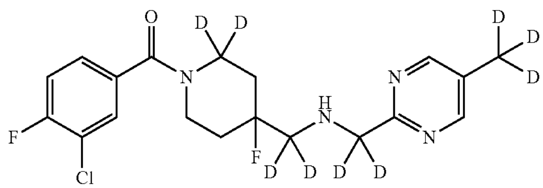 [SMILES: [2H]C([2H])([2H])c1cnc(C([2H])([2H])NC([2H])([2H])C2(F)CCN(C(=O)c3ccc(F)c(Cl)c3)C([2H])([2H])C2)nc1] |
| 190 | 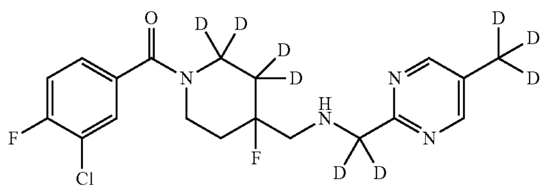 [SMILES: [2H]C([2H])([2H])c1cnc(C([2H])([2H])NCC2(F)CCN(C(=O)c3ccc(F)c(Cl)c3)C([2H])([2H])C2([2H])[2H])nc1] |
| 191 | 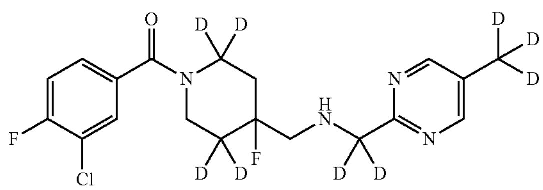 [SMILES: [2H]C([2H])([2H])c1cnc(C([2H])([2H])NCC2(F)CC([2H])([2H])N(C(=O)c3ccc(F)c(Cl)c3)CC2([2H])[2H])nc1] |
| 192 | 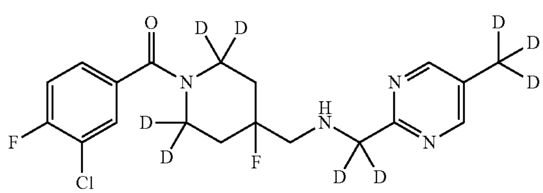 [SMILES: [2H]C([2H])([2H])c1cnc(C([2H])([2H])NCC2(F)CC([2H])([2H])N(C(=O)c3ccc(F)c(Cl)c3)C([2H])([2H])C2)nc1] |
| 193 | 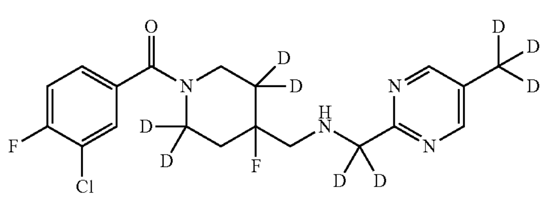 [SMILES: [2H]C([2H])([2H])c1cnc(C([2H])([2H])NCC2(F)CC([2H])([2H])N(C(=O)c3ccc(F)c(Cl)c3)CC2([2H])[2H])nc1] |
| 194 | 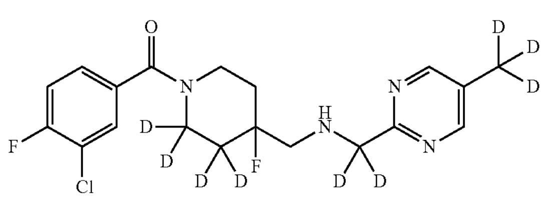 [SMILES: [2H]C([2H])([2H])c1cnc(C([2H])([2H])NCC2(F)CCN(C(=O)c3ccc(F)c(Cl)c3)C([2H])([2H])C2([2H])[2H])nc1] |
| 195 | 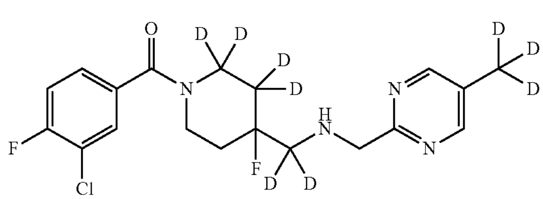 [SMILES: [2H]C([2H])([2H])c1cnc(CNC([2H])([2H])C2(F)CCN(C(=O)c3ccc(F)c(Cl)c3)C([2H])([2H])C2([2H])[2H])nc1] |
| 196 | 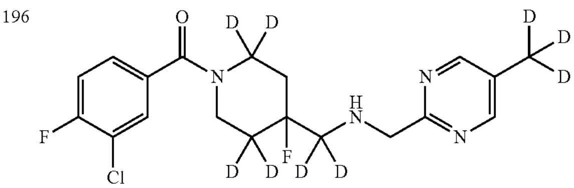 |
| 197 | 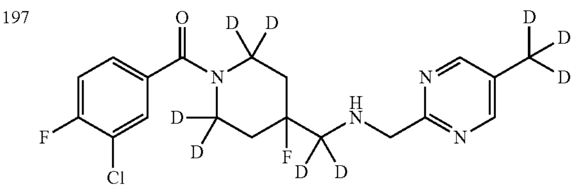 |
| 198 | 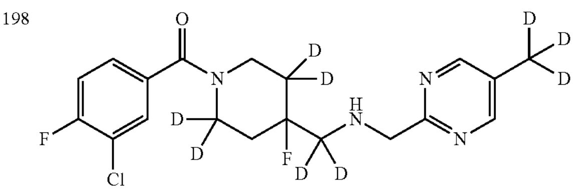 |
| 199 | 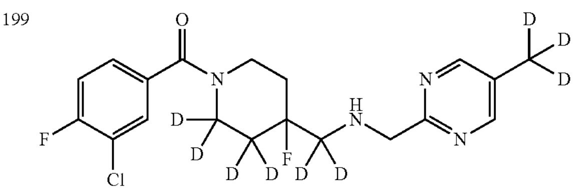 |
| 200 | 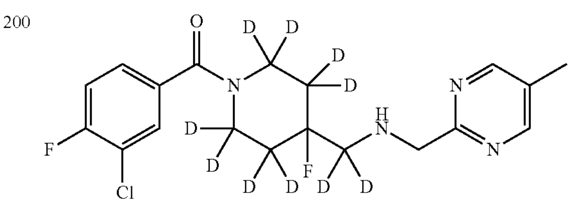 |
| 201 | 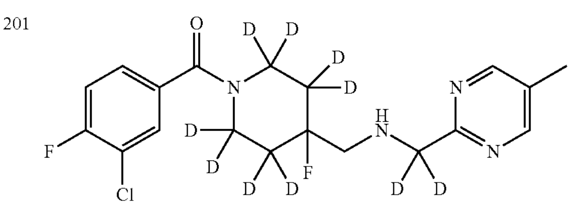 |
| 202 | 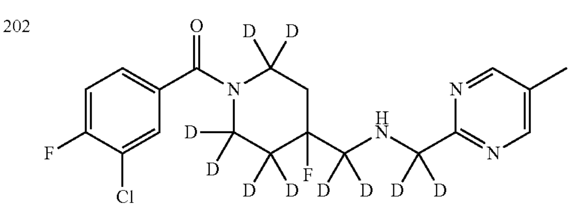 |
| 203 | 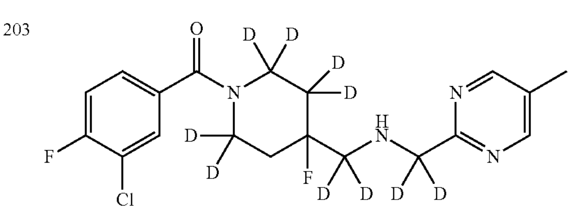 |

TABLE 1-continued

| No. | Structure |
|-----|-----------|
| 204 | 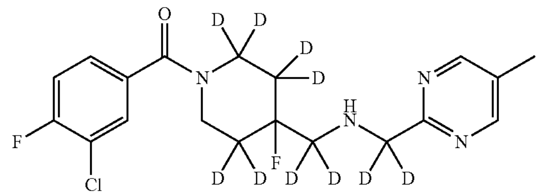 [SMILES: [2H]C([2H])(NC([2H])([2H])C1(F)C([2H])([2H])CN(C(=O)c2ccc(F)c(Cl)c2)C([2H])([2H])C1([2H])[2H])c1ncc(C)cn1] |
| 205 | 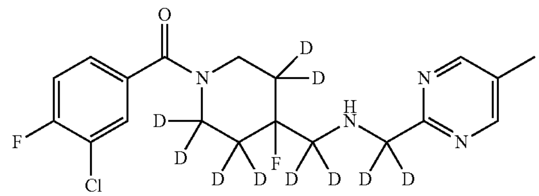 [SMILES: [2H]C([2H])(NC([2H])([2H])C1(F)C([2H])([2H])CN(C(=O)c2ccc(F)c(Cl)c2)C([2H])([2H])C1([2H])[2H])c1ncc(C)cn1] |
| 206 | 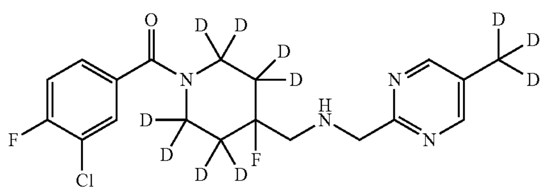 [SMILES: [2H]C([2H])([2H])c1cnc(CNCC2(F)C([2H])([2H])C([2H])([2H])N(C(=O)c3ccc(F)c(Cl)c3)C([2H])([2H])C2([2H])[2H])nc1] |
| 207 | 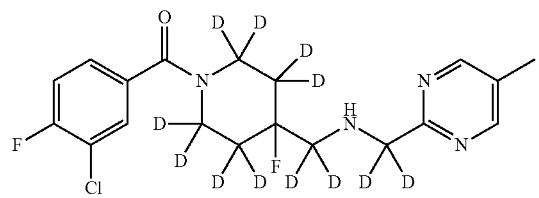 [SMILES: [2H]C([2H])(NC([2H])([2H])C1(F)C([2H])([2H])C([2H])([2H])N(C(=O)c2ccc(F)c(Cl)c2)C([2H])([2H])C1([2H])[2H])c1ncc(C)cn1] |
| 208 | 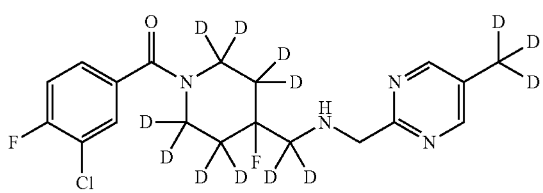 [SMILES: [2H]C([2H])([2H])c1cnc(CNC([2H])([2H])C2(F)C([2H])([2H])C([2H])([2H])N(C(=O)c3ccc(F)c(Cl)c3)C([2H])([2H])C2([2H])[2H])nc1] |
| 209 | 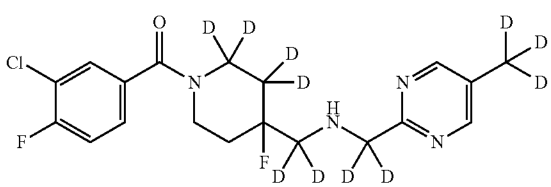 [SMILES: [2H]C([2H])([2H])c1cnc(C([2H])([2H])NC([2H])([2H])C2(F)CCN(C(=O)c3ccc(F)c(Cl)c3)C([2H])([2H])C2([2H])[2H])nc1] |
| 210 | 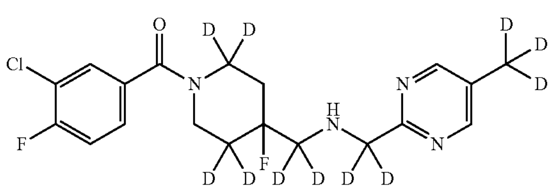 [SMILES: [2H]C([2H])([2H])c1cnc(C([2H])([2H])NC([2H])([2H])C2(F)CC([2H])([2H])N(C(=O)c3ccc(F)c(Cl)c3)CC2([2H])[2H])nc1] |
| 211 | 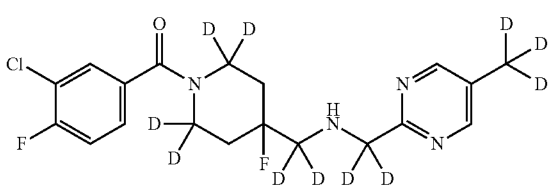 [SMILES: [2H]C([2H])([2H])c1cnc(C([2H])([2H])NC([2H])([2H])C2(F)CC([2H])([2H])N(C(=O)c3ccc(F)c(Cl)c3)C([2H])([2H])C2)nc1] |
| 212 | 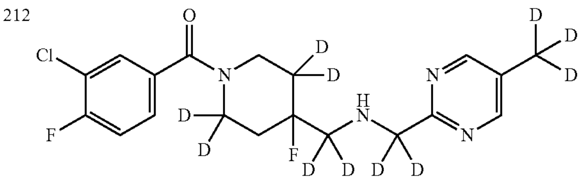 |
| 213 | 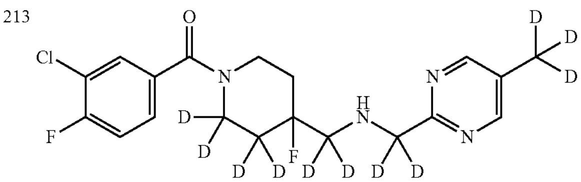 |
| 214 | 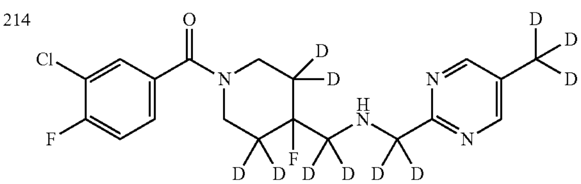 |
| 215 | 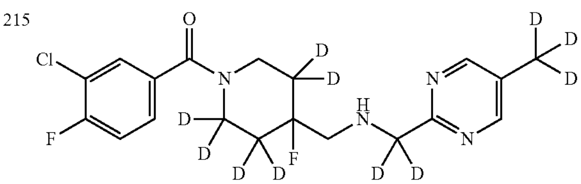 |
| 216 | 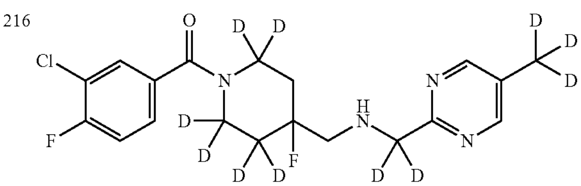 |
| 217 | 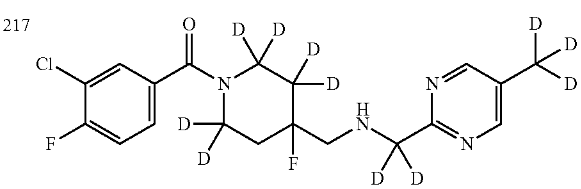 |
| 218 | 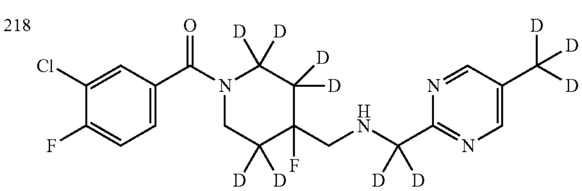 |
| 219 | 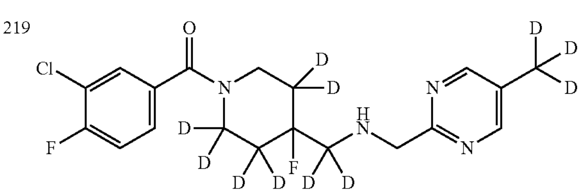 |

TABLE 1-continued

| No. | Structure |
|-----|-----------|
| 220 | 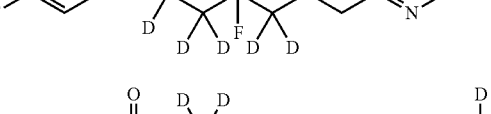 |
| 221 | 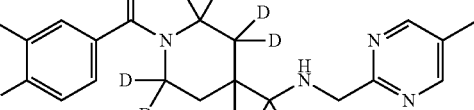 |
| 222 | 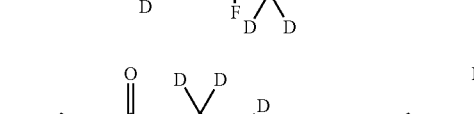 |
| 223 | 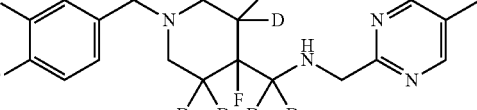 |
| 224 | 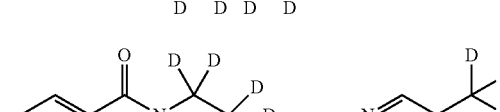 |
| 225 | 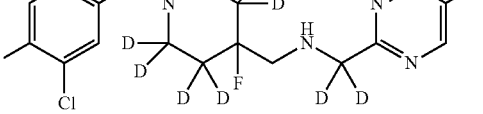 |
| 226 | 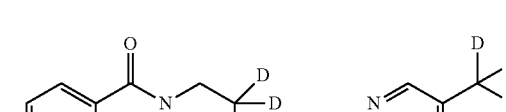 |
| 227 | 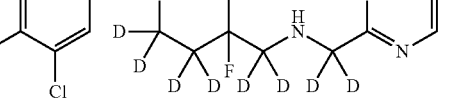 |

TABLE 1-continued

| No. | Structure |
|-----|-----------|
| 228 | 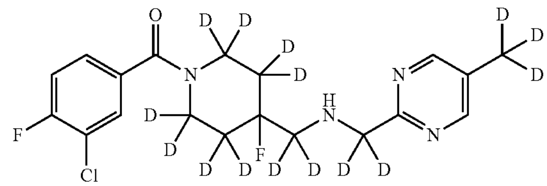 [SMILES: [2H]C([2H])([2H])c1cnc(C([2H])([2H])NC([2H])([2H])C2(F)C([2H])([2H])C([2H])([2H])N(C(=O)c3ccc(F)c(Cl)c3)C([2H])([2H])C2([2H])[2H])nc1] |

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In Vitro Liver Microsomal Stability Assay

Human liver microsomal stability assays were conducted at 0.5 mg per mL liver microsome protein with NADPH (2 mM, pH 7.4). Test compounds were prepared as solutions in DMSO and added to the assay mixture (1 µM, final concentration in incubation) to be incubated at 37±1° C. Reactions were initiated with the addition of cofactor and are stopped at 0, 5, 15, 30, and 45 min after cofactor addition with stop reagent (acetonitrile). After quenching, plates containing samples are vibrated for 10 min (600 rpm/min) and then centrifuged at 5594 g for 15 min. Supernatant fractions were analyzed by LC-MS/MS to determine the percent remaining and estimate the degradation half-life of the test compounds. The results are presented in Table 2 below.

TABLE 2

| Example # | Clearance % change over d0 | Half-life % change over d0 |
|-----------|---------------------------|---------------------------|
| 1 | 0 | 0 |
| 2 | −7.5 | 8.4 |
| 3 | −5. | 5.6 |
| 4 | −5.1 | 5.4 |
| 5 | −6.7 | 7.2 |
| 6 | −9.1 | 10.0 |
| 7 | −5.8 | 6.2 |
| 8 | 0 | 0 |
| 9 | 3.7 | −3.5 |
| 10 | 8.4 | −7.7 |
| 11 | 5.5 | −5.2 |
| 12 | 2.1 | −2.1 |
| 13 | −0.9 | 0.9 |

In Vitro Metabolism Using Human Cytochrome $P_{450}$ Enzymes

The cytochrome $P_{450}$ enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula I, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 min. The supernatant is analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Monoamine Oxidase A Inhibition and Oxidative Turnover

The procedure is carried out using the methods described by Weyler, *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM NaP$_i$ buffer, pH 7.2, containing 0.2% Triton X-100 (monoamine oxidase assay buffer), plus 1 mM kynuramine, and the desired amount of enzyme in 1 mL total volume.

Monooamine Oxidase B Inhibition and Oxidative Turnover

The procedure is carried out as described in Uebelhack, *Pharmacopsychiatry* 1998, 31(5), 187-192, which is hereby incorporated by reference in its entirety.

5-hydroxytryptamine (5-HT$_{1A}$) In Vitro Assay

The in vitro affinity of the compounds for the 5-HT$_{1A}$ receptors is determined according to the methods provided in U.S. Pat. No. 6,020,345, which is hereby incorporated by references in its entirety.

5-hydroxytryptamine (5-HT$_{1A}$) Binding Assay

The study of binding of the compounds to the 5-HT$_{1A}$ receptors is determined according to the methods provided in U.S. Pat. No. 6,020,345, which is hereby incorporated by reference in its entirety.

5-hydroxytryptamine (5-HT$_{1A}$) In Vivo Assay

In vivo evaluation of the agonist activity of the 5-HT$_{1A}$ receptors for the compounds is determined according to the methods provided in U.S. Pat. No. 6,020,345, which is hereby incorporated by references in its entirety.

D2 Dopaminergic Receptor Binding Assay

The study of binding of the compounds to the D2 dopaminergic receptors is determined according to the methods provided in U.S. Pat. No. 6,020,345, which is hereby incorporated by reference in its entirety.

From the foregoing description, one skilled in the art can ascertain the essential characteristics of this invention, and without departing from the spirit and scope thereof, can make various changes and modifications of the invention to adapt it to various usages and conditions.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound that is:

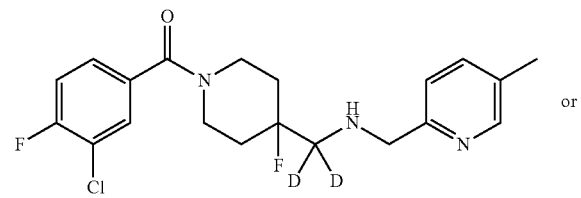

or

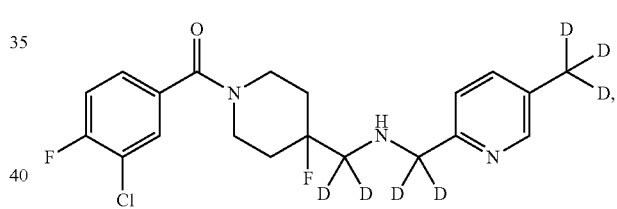

or a pharmaceutically acceptable salt or solvate thereof;
wherein each D has a deuterium enrichment of at least about 10%.

2. The compound of claim 1, wherein the compound is:

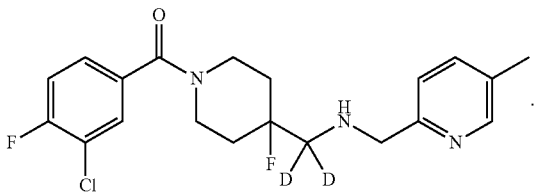 [SMILES: [2H]C([2H])(NCc1ccc(C)cn1)C1(F)CCN(C(=O)c2ccc(F)c(Cl)c2)CC1]

3. The compound of claim 1, wherein the compound is a pharmaceutically acceptable salt that is a hydrochloride, hydrobromide, sulfate, formate, acetate, trifluoroacetate, propionate, succinate, fumarate, citrate, tartrate, glutamate, benzoate, salicylate, stearate, lactate, mesylate, tosylate, besylate, phosphate, or maleate salt.

4. The compound of claim 1, wherein each D has deuterium enrichment of at least about 90%.

5. The compound of claim 1, that is:

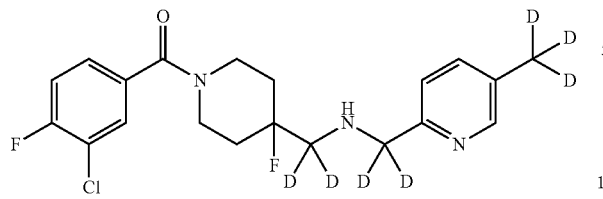

or a pharmaceutically acceptable salt or solvate thereof.

6. The compound of claim 1, that is:

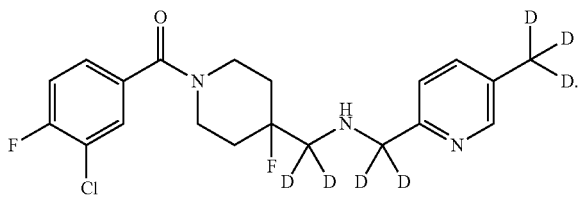

or a pharmaceutically acceptable salt or solvate thereof.

7. The compound of claim 1, that is:

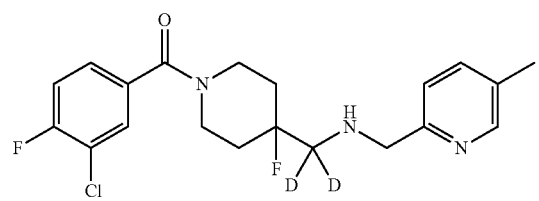 [SMILES: [2H]C([2H])(NCc1ccc(C)cn1)C1(F)CCN(C(=O)c2ccc(F)c(Cl)c2)CC1]

or a pharmaceutically acceptable salt or solvate thereof.

8. The compound of claim 1, wherein each D has deuterium enrichment of at least about 95%.

9. The compound of claim 1, wherein each D has deuterium enrichment of at least about 97%.

10. The compound of claim 1, wherein each D has deuterium enrichment of at least about 99%.

11. A pharmaceutical composition comprising the compound of claim 1, and a pharmaceutically acceptable carrier.

* * * * *